US011662561B2

(12) United States Patent
de Juan et al.

(10) Patent No.: US 11,662,561 B2
(45) Date of Patent: May 30, 2023

(54) SYSTEMS AND METHODS FOR TREATING HEARING LOSS

(71) Applicant: Spiral Therapeutics Inc., Brisbane, CA (US)

(72) Inventors: Eugene de Juan, Brisbane, CA (US); Signe Erickson, Brisbane, CA (US); Charles Limb, Brisbane, CA (US); Hugo Peris, Brisbane, CA (US); Andrew Ayoob, Brisbane, CA (US); Vrad Levering, Brisbane, CA (US)

(73) Assignee: Spiral Therapeutics Inc., South San Francisco, CA (US)

( * ) Notice: Subject to any disclaimer, the term of this patent is extended or adjusted under 35 U.S.C. 154(b) by 244 days.

(21) Appl. No.: 17/155,800

(22) Filed: Jan. 22, 2021

(65) Prior Publication Data

US 2021/0228237 A1    Jul. 29, 2021

Related U.S. Application Data

(60) Provisional application No. 63/082,996, filed on Sep. 24, 2020, provisional application No. 63/081,015, (Continued)

(51) Int. Cl.
 *G02B 21/00*    (2006.01)
 *G02B 21/22*    (2006.01)
 (Continued)

(52) U.S. Cl.
 CPC .......... *G02B 21/0012* (2013.01); *A61B 1/018* (2013.01); *A61B 1/227* (2013.01); (Continued)

(58) Field of Classification Search
 CPC ............ A61B 17/3423; A61B 17/3478; A61B 2017/00115; A61B 2017/00787
 See application file for complete search history.

(56) References Cited

U.S. PATENT DOCUMENTS 5,421,818 A    6/1995 Arenberg
6,024,726 A    2/2000 Hill
 (Continued)

FOREIGN PATENT DOCUMENTS

WO    WO 1994010596    5/1994
WO    WO 2008097317    8/2008
 (Continued)

OTHER PUBLICATIONS

PCT Invitation to Pay Fees in International Appln. No. PCT/US2021/014618, dated Apr. 1, 2021, 3 pages.
 (Continued)

*Primary Examiner* — Shaun L David
*Assistant Examiner* — Rachael L Geiger
(74) *Attorney, Agent, or Firm* — Fish & Richardson P.C.

(57) ABSTRACT

Systems and methods can be employed for trans-tympanic membrane access to the middle ear for delivery of a therapeutic agent, for example, to the round window niche adjacent to the cochlea under direct visualization. The systems and methods can also be used to improve accessibility and visualization for various otological surgical procedures, such as, but not limited to, cholesteatoma removal, tympanic membrane repair and ossicular chain repair.

13 Claims, 28 Drawing Sheets

Related U.S. Application Data filed on Sep. 21, 2020, provisional application No. 63/080,510, filed on Sep. 18, 2020, provisional application No. 63/078,141, filed on Sep. 14, 2020, provisional application No. 63/077,448, filed on Sep. 11, 2020, provisional application No. 63/051,568, filed on Jul. 14, 2020, provisional application No. 63/040,495, filed on Jun. 17, 2020, provisional application No. 63/024,183, filed on May 13, 2020, provisional application No. 62/965,481, filed on Jan. 24, 2020.

(51) Int. Cl.

| | | |
|---|---|---|
| *A61B 1/018* | (2006.01) | |
| *A61B 1/227* | (2006.01) | |
| *A61B 17/29* | (2006.01) | |
| *A61M 31/00* | (2006.01) | |
| *A61B 17/34* | (2006.01) | |
| *A61M 37/00* | (2006.01) | |
| *A61B 17/32* | (2006.01) | |
| *A61B 18/04* | (2006.01) | |
| *A61B 18/20* | (2006.01) | |
| *A61F 2/958* | (2013.01) | |
| *A61B 17/3205* | (2006.01) | |
| *A61B 18/14* | (2006.01) | |
| *A61F 11/20* | (2022.01) | |
| *A61B 17/00* | (2006.01) | |
| *A61B 18/00* | (2006.01) | |
| *A61F 2/18* | (2006.01) | |

(52) U.S. Cl.
CPC .......... *A61B 17/29* (2013.01); *A61B 17/3205* (2013.01); *A61B 17/320068* (2013.01); *A61B 17/3423* (2013.01); *A61B 17/3468* (2013.01); *A61B 17/3478* (2013.01); *A61B 18/04* (2013.01); *A61B 18/1485* (2013.01); *A61B 18/20* (2013.01); *A61F 2/958* (2013.01); *A61F 11/20* (2022.01); *A61F 11/202* (2022.01); *A61M 31/00* (2013.01); *A61M 31/002* (2013.01); *A61M 37/0015* (2013.01); *G02B 21/0032* (2013.01); *G02B 21/22* (2013.01); *A61B 2017/00115* (2013.01); *A61B 2017/00787* (2013.01); *A61B 2017/00867* (2013.01); *A61B 2017/32007* (2017.08); *A61B 2018/00327* (2013.01); *A61B 2217/005* (2013.01); *A61F 2002/183* (2013.01); *A61F 2250/0067* (2013.01); *A61M 2037/0023* (2013.01); *A61M 2037/0046* (2013.01); *A61M 2205/04* (2013.01); *A61M 2210/0662* (2013.01); *A61M 2210/0668* (2013.01)

(56) References Cited

U.S. PATENT DOCUMENTS

| | | |
|---|---|---|
| 6,045,528 A | 4/2000 | Arenberg et al. |
| 6,120,484 A | 9/2000 | Silverstein |
| 6,440,102 B1 | 8/2002 | Arenberg et al. |
| 6,648,873 B2 | 11/2003 | Arenberg et al. |
| 7,351,246 B2 | 4/2008 | Epley |
| 7,704,259 B2 | 4/2010 | Kaplan et al. |
| 8,197,461 B1 | 6/2012 | Arenberg et al. |
| 9,352,084 B2 | 5/2016 | Decker et al. |
| 9,616,207 B2 | 4/2017 | Verhoeven et al. |
| 10,130,514 B2 | 11/2018 | Imran et al. |
| 10,492,670 B1 | 12/2019 | Bendory et al. |
| 2003/0220536 A1 | 11/2003 | Hissong |
| 2004/0133099 A1 | 7/2004 | Dyer et al. |
| 2004/0172005 A1 | 9/2004 | Arenberg et al. |
| 2009/0076581 A1* | 3/2009 | Gibson ............ A61M 5/14244 607/137 |
| 2011/0224629 A1 | 9/2011 | Jolly et al. |
| 2012/0150119 A1* | 6/2012 | Schaeffer ............ A61M 27/002 604/164.11 |
| 2013/0060131 A1 | 3/2013 | Oghalai et al. |
| 2013/0085476 A1 | 4/2013 | Imran |
| 2013/0245569 A1 | 9/2013 | Jolly et al. |
| 2014/0277043 A1* | 9/2014 | Jenkins .................. A61B 34/30 134/6 |
| 2015/0209074 A1 | 7/2015 | Payne |
| 2015/0290040 A1 | 10/2015 | Vaughan et al. |
| 2016/0346511 A1 | 12/2016 | Cohen et al. |
| 2017/0172804 A1 | 6/2017 | Watanabe et al. |
| 2018/0085258 A1 | 3/2018 | Andreas et al. |
| 2019/0015254 A1 | 1/2019 | Bendory et al. |
| 2019/0321610 A1 | 10/2019 | Goldfarb et al. |
| 2019/0321611 A1 | 10/2019 | Sacherman et al. |
| 2020/0094030 A1 | 3/2020 | Kim et al. |
| 2021/0015674 A1* | 1/2021 | Frölich ................... A61F 11/20 |
| 2021/0228849 A1 | 7/2021 | de Juan et al. |

FOREIGN PATENT DOCUMENTS

| | | |
|---|---|---|
| WO | WO 2019116024 | 6/2019 |
| WO | WO 2019152866 | 8/2019 |
| WO | WO 2019200259 | 10/2019 |
| WO | WO 2020115674 | 6/2020 |

OTHER PUBLICATIONS

International Search Report and Written Opinion in International Appln. No. PCT/US2021/14618, dated Jul. 8, 2021, 12 pages.

\* cited by examiner

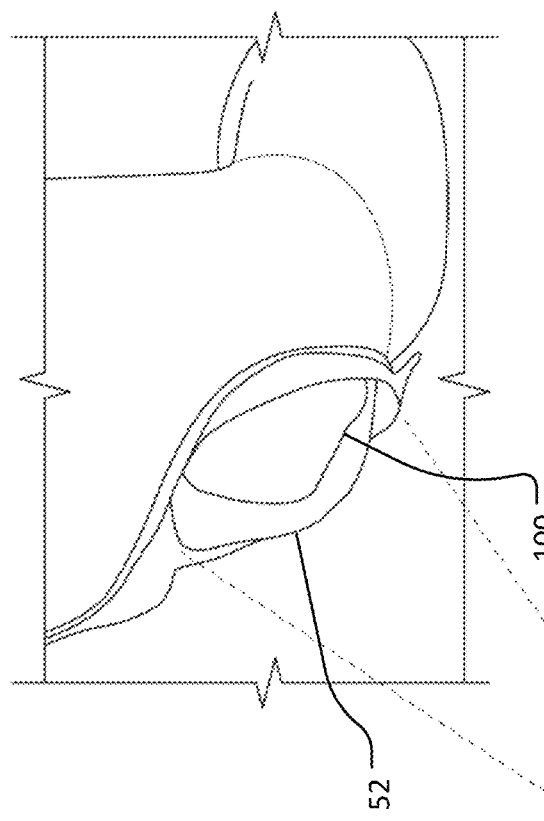
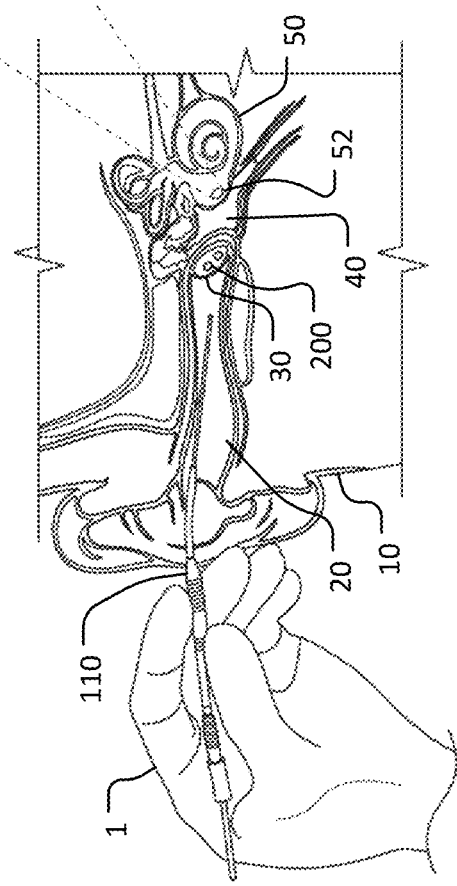
FIG. 1
FIG. 2

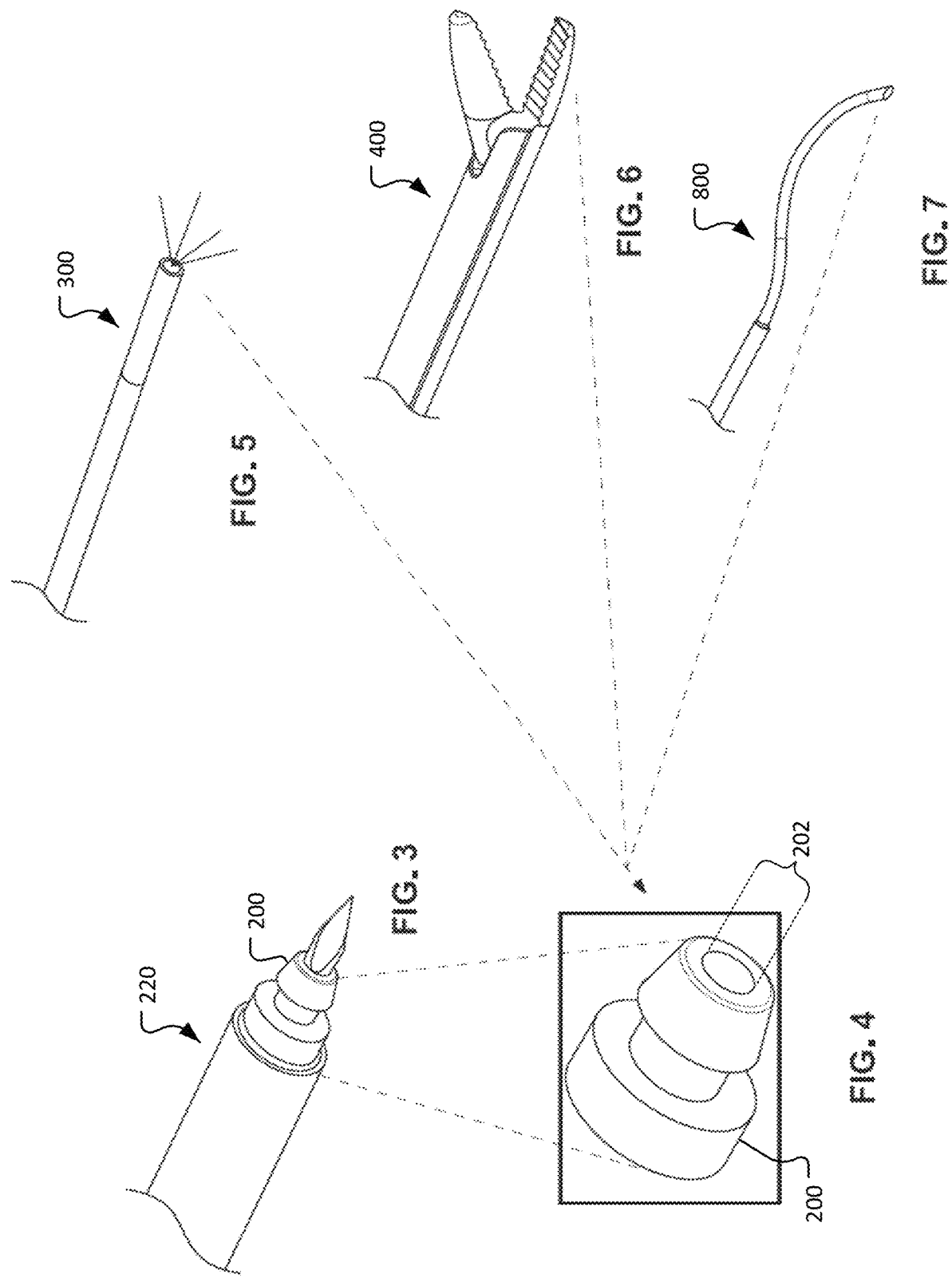

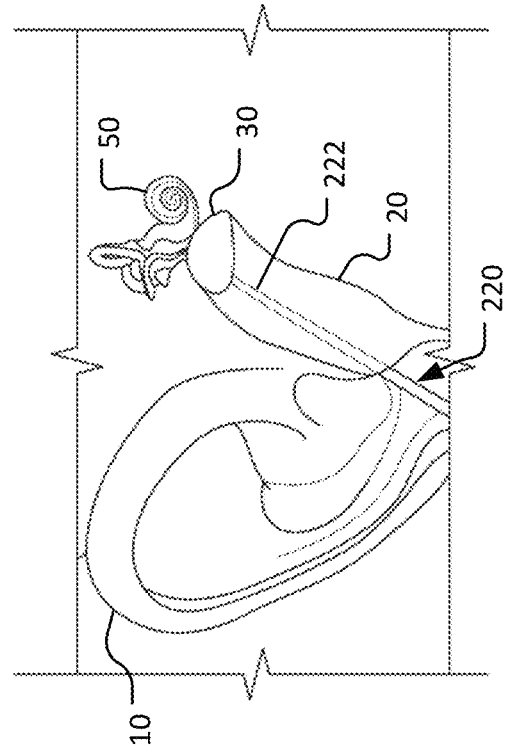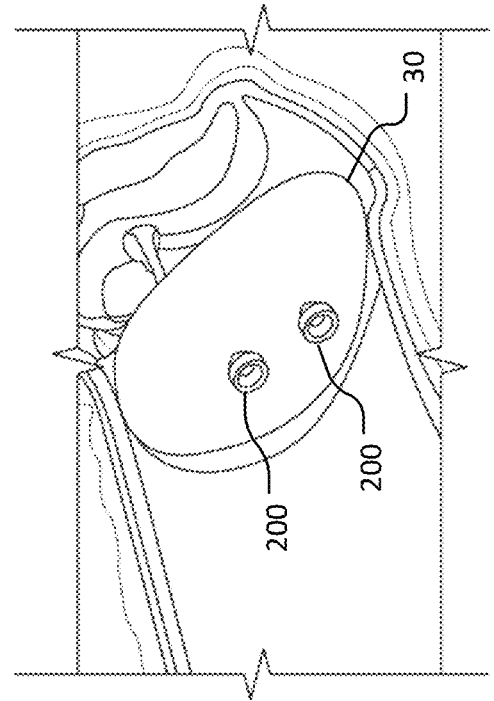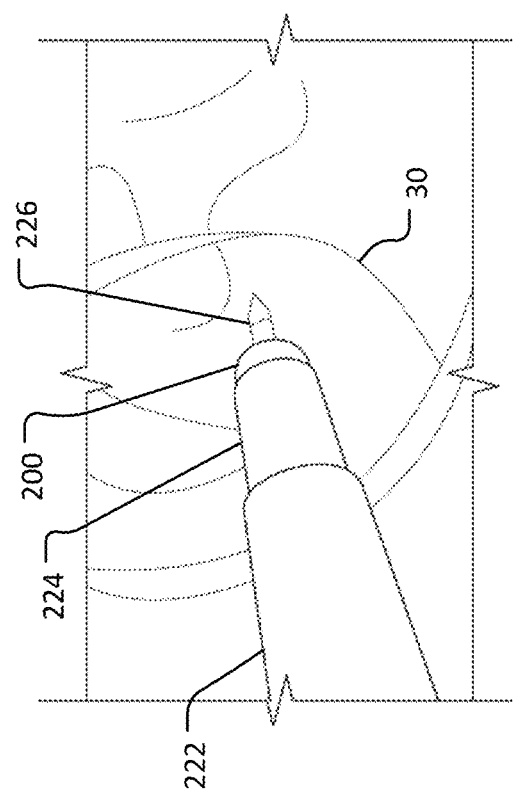

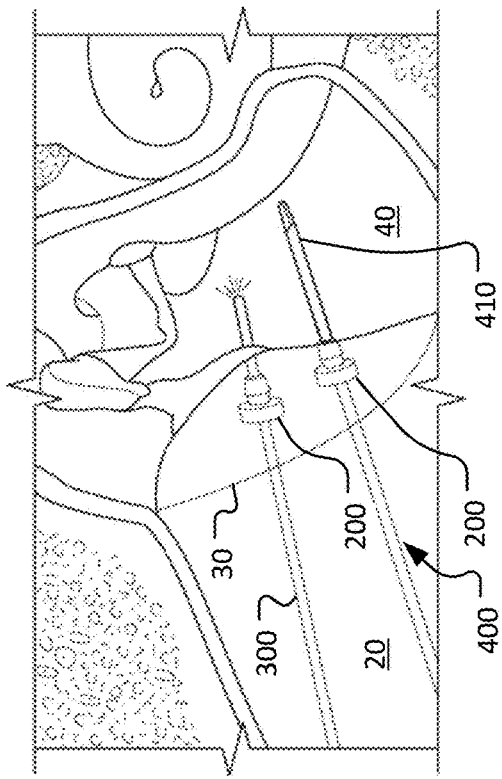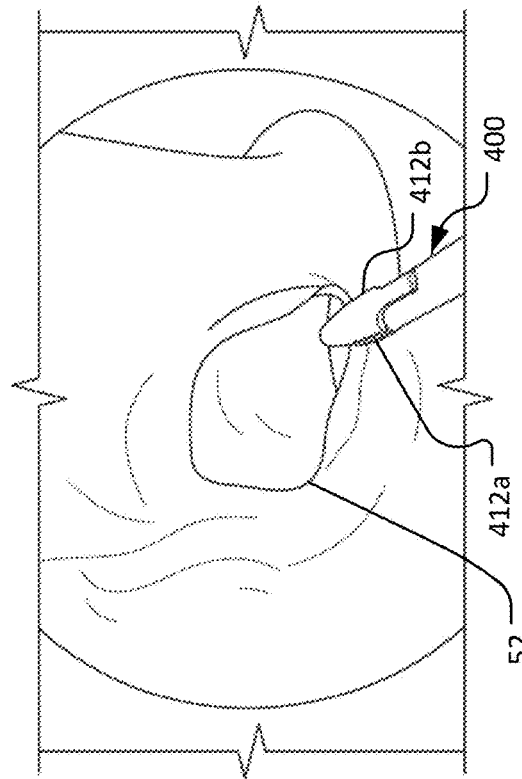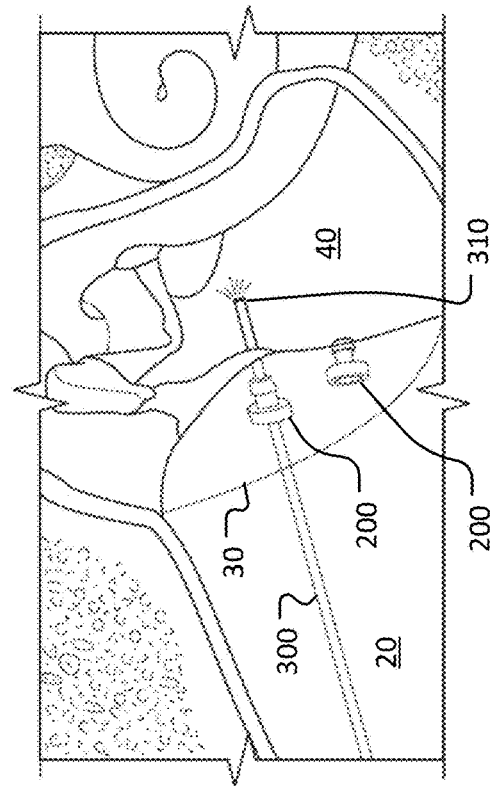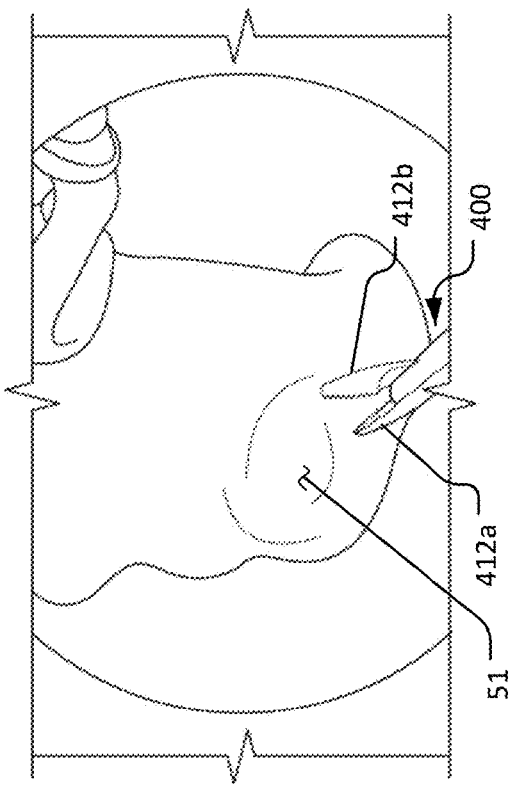

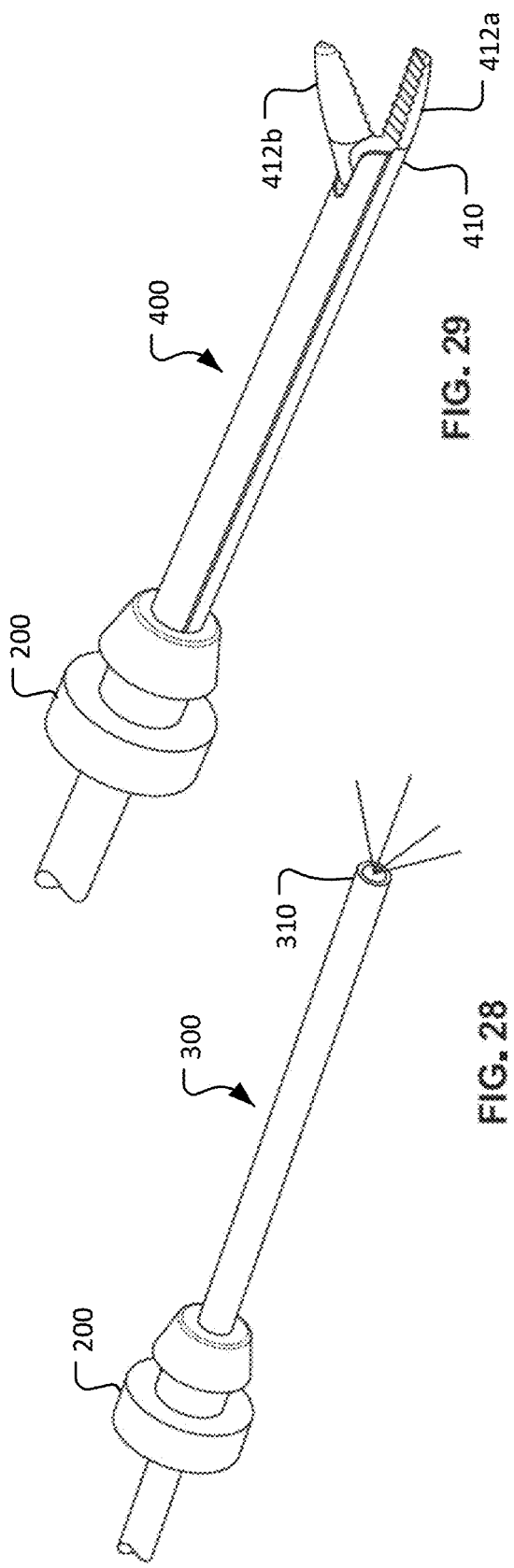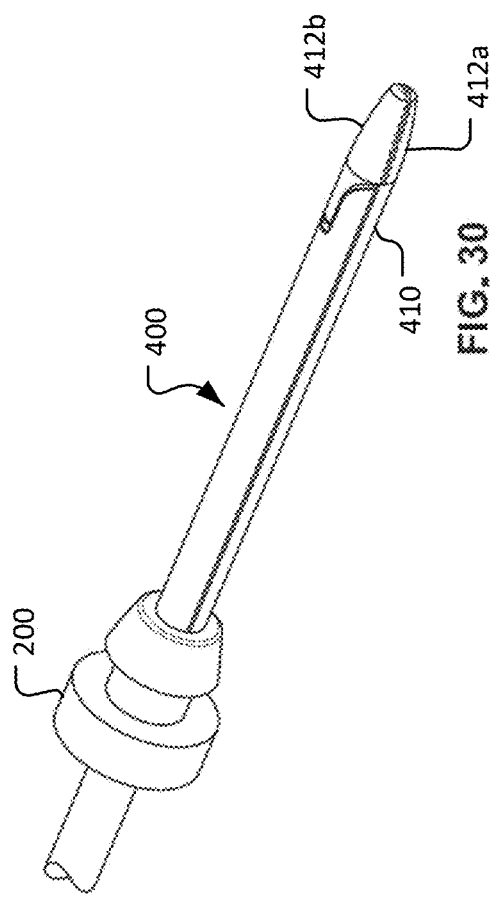

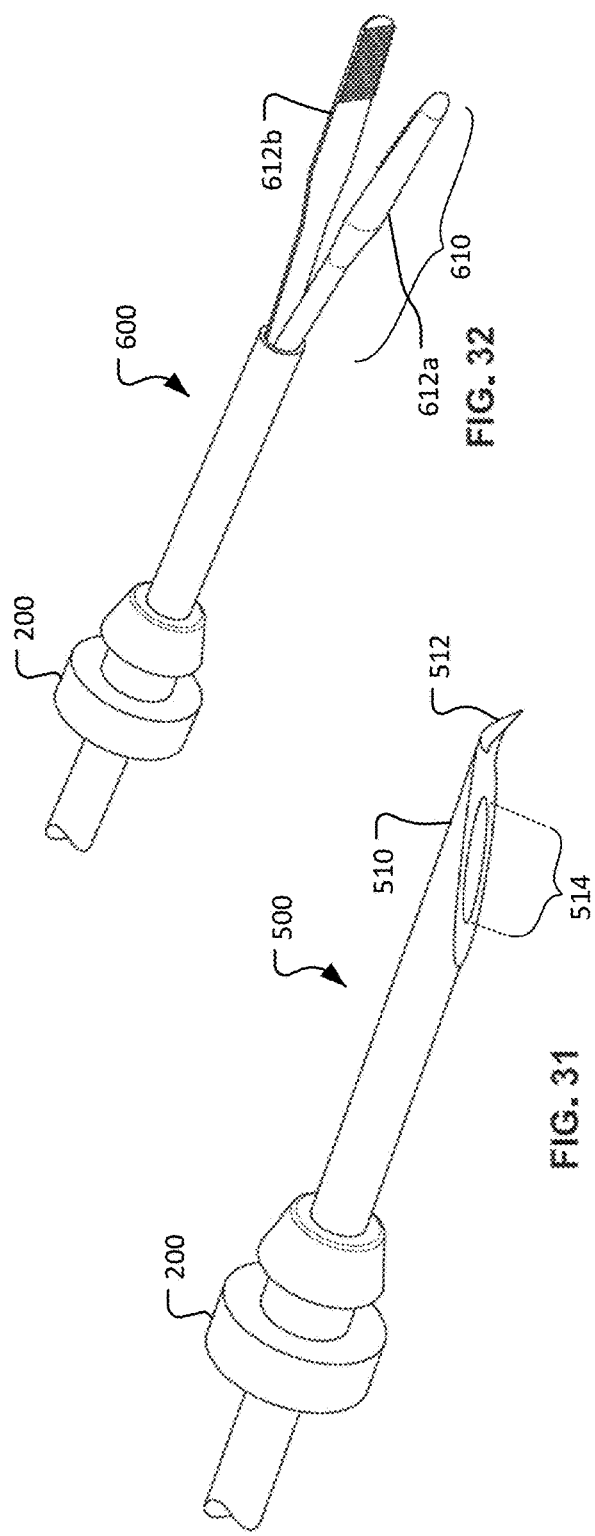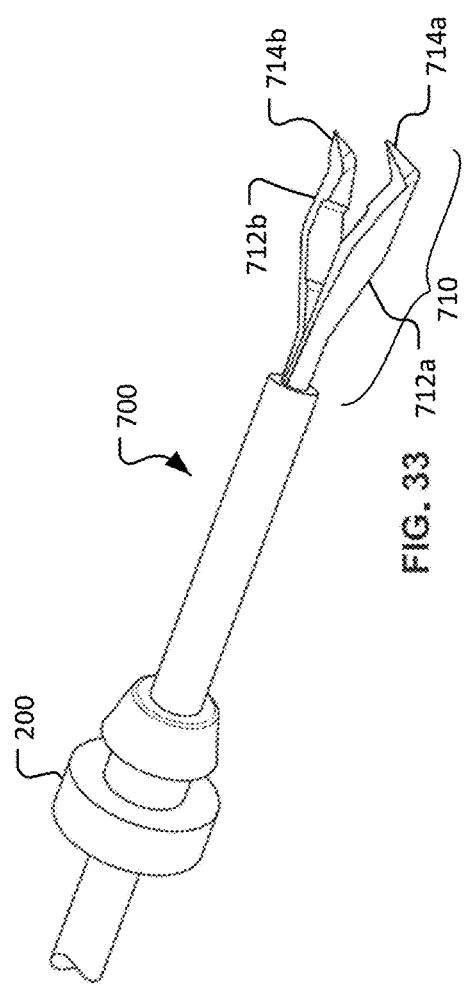

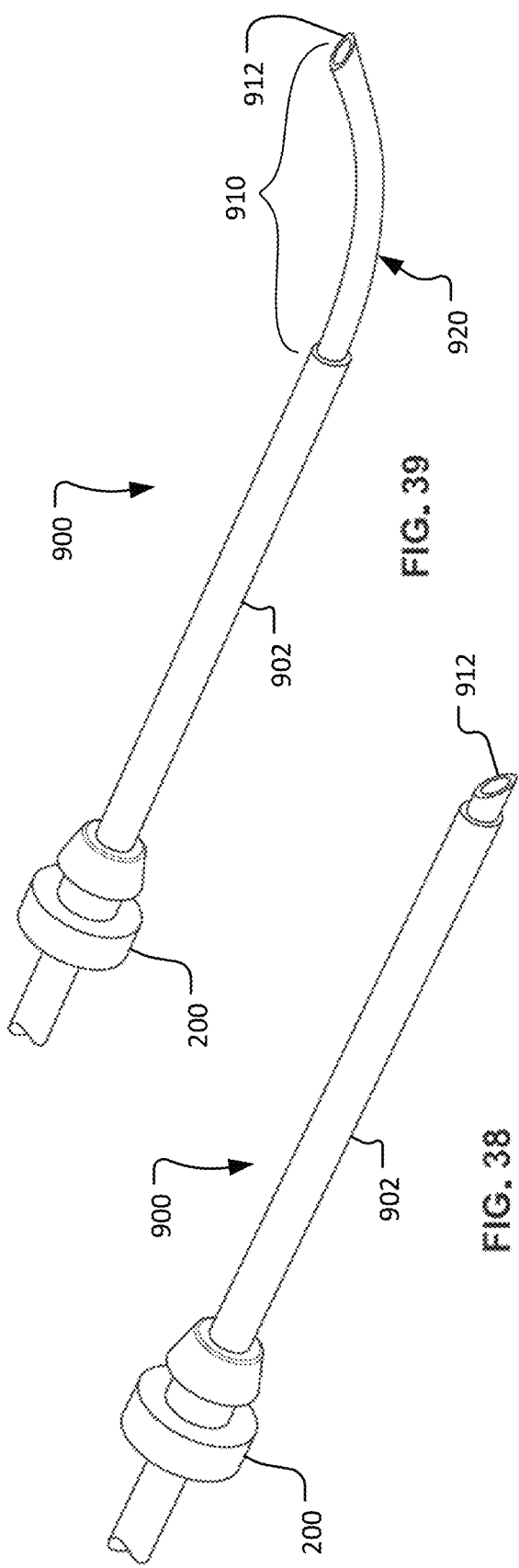
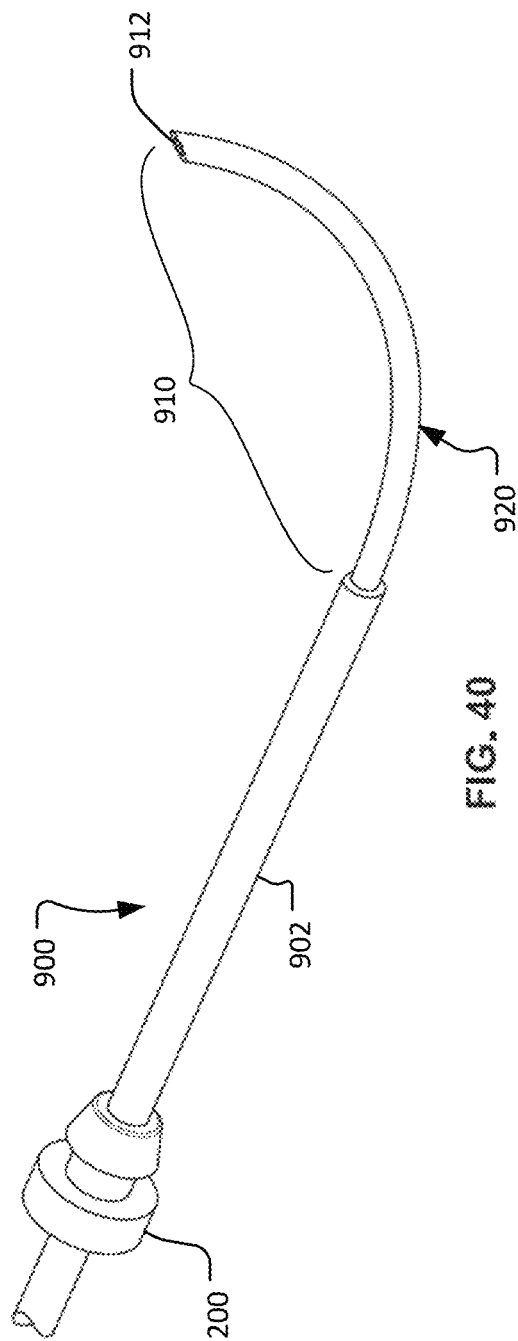

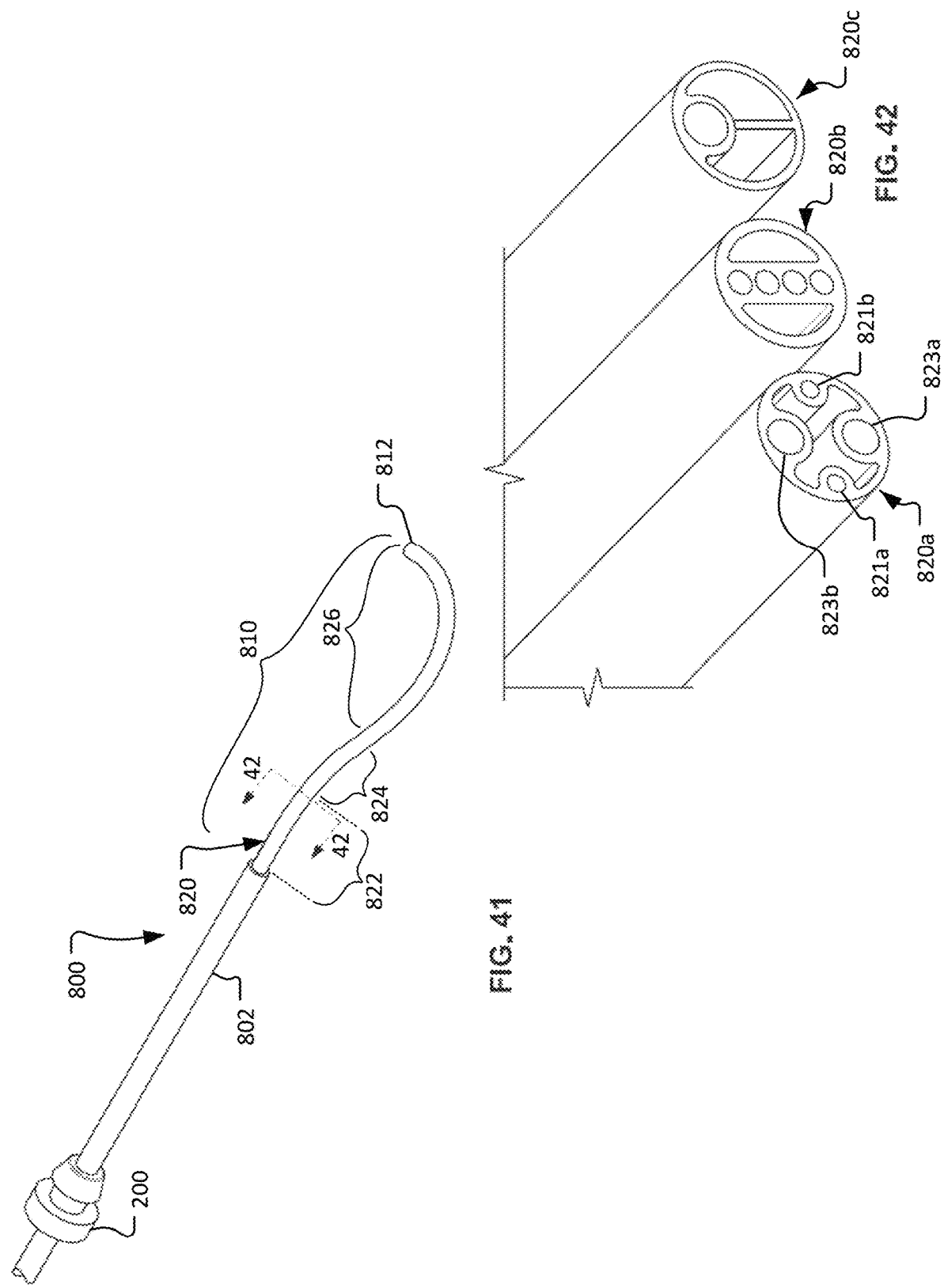

Detail B--B

Detail B--B

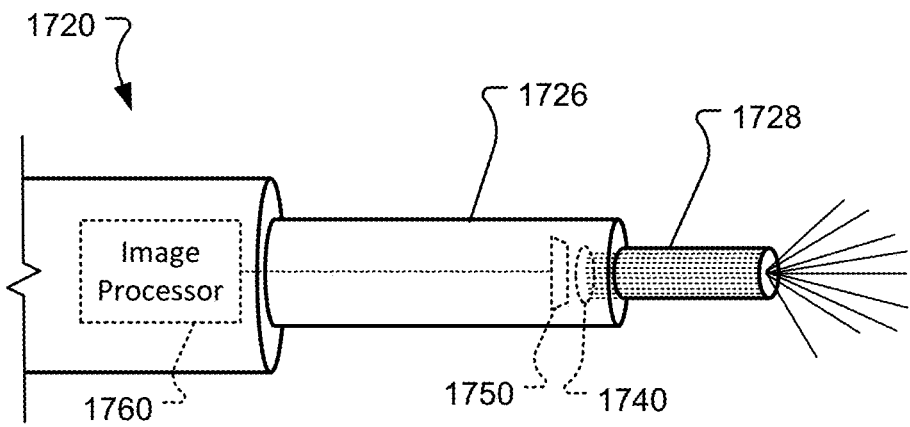
Detail B--B
FIG. 71
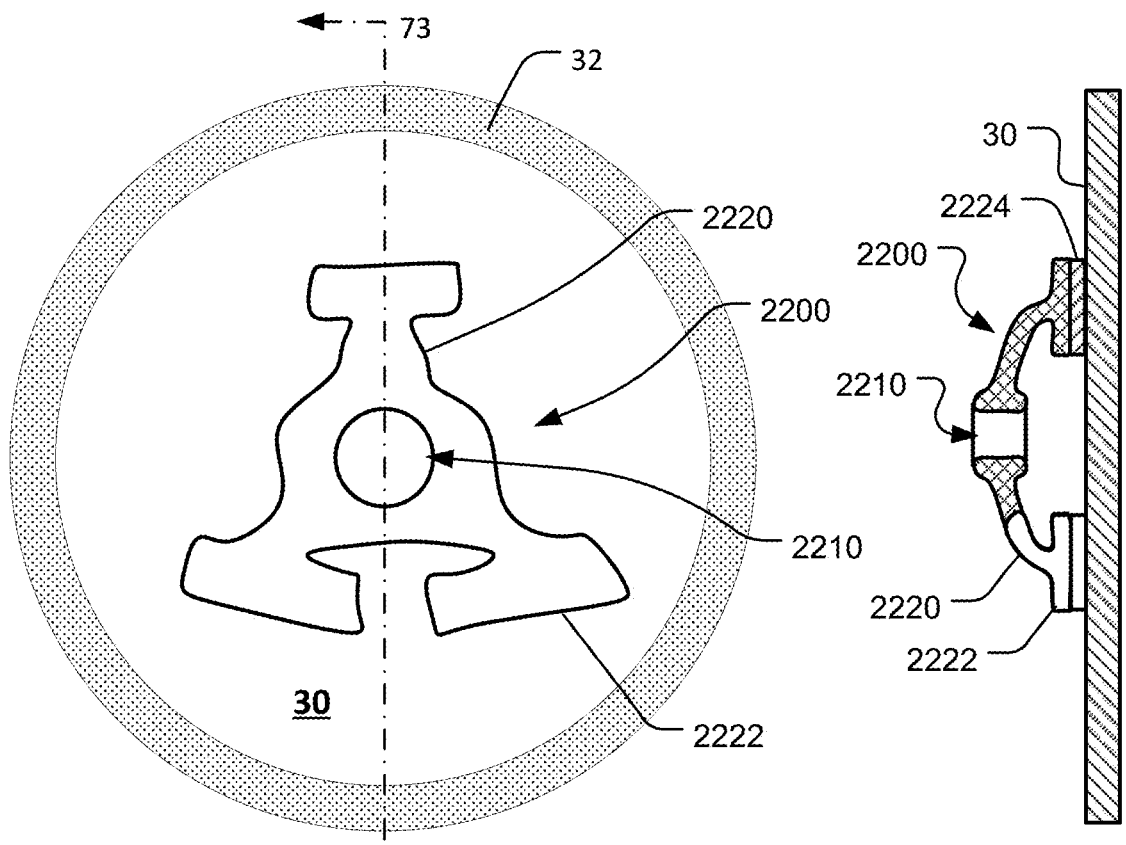
FIG. 72
Cross-section 73--73
FIG. 73

SYSTEMS AND METHODS FOR TREATING HEARING LOSS

CROSS-REFERENCE TO RELATED APPLICATIONS

This application claims the benefit of priority to U.S. Provisional Application No. 62/965,481 filed on Jan. 24, 2020, U.S. Provisional Application No. 63/024,183 filed on May 13, 2020 (which is fully incorporated herein by reference), U.S. Provisional Application No. 63/040,495 filed on Jun. 17, 2020 (which is fully incorporated herein by reference), U.S. Provisional Application No. 63/051,568 filed on Jul. 14, 2020 (which is fully incorporated herein by reference), U.S. Provisional Application No. 63/077,448 filed on Sep. 11, 2020 (which is fully incorporated herein by reference), U.S. Provisional Application No. 63/078,141 filed on Sep. 14, 2020 (which is fully incorporated herein by reference), U.S. Provisional Application No. 63/080,510 filed on Sep. 18, 2020 (which is fully incorporated herein by reference), U.S. Provisional Application No. 63/081,015 filed on Sep. 21, 2020 (which is fully incorporated herein by reference), and U.S. Provisional Application No. 63/082,996 filed on Sep. 24, 2020 (which is fully incorporated herein by reference).

TECHNICAL FIELD

This document relates to systems, methods, and materials for treating ear disorders including, but not limited to hearing loss. In some examples, the systems and methods include trans-tympanic membrane access to the middle ear for targeted delivery of a therapeutic formulation under direct visualization.

BACKGROUND

The human ear is subject to a variety of disorders including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, outer ear infections, middle ear infections, schwannoma, and tympanic membrane perforations, to provide a few examples.

In one example, Conductive Hearing Loss (CHL) involves the loss of normal mechanical pathways for sound to reach the hair cells in the cochlea, for example due to malformation, accumulation of fluid in the middle ear, disruption of the tympanic membrane, presence of tumors, and/or damage to ossicles. SensoriNeural Hearing Loss (SNHL) is due to the absence of, or damage to, hair cells in the cochlea, or to the acoustic nerve. SNHL is typically associated with exposure to loud noise, head trauma, aging, infection, Meniere's Disease, tumors, ototoxicity, genetic diseases like Usher's disease, and the like.

SUMMARY

This document describes systems and methods for minimally invasive access to the middle ear for purposes of delivering treatment for inner and middle ear disorders. For example, this document describes systems and methods for trans-tympanic membrane access instrument to achieve minimally invasive delivery of therapeutic formulations into the round window niche and adjacent to the round window membrane of the cochlea under direct visualization. In particular implementations, the active agent of the therapeutic formulation may then transfer passively by diffusion across the round window membrane(s), according to a concentration gradient, into the perilymph (within the cochlea). The devices, systems, materials, compounds, compositions, articles, and methods described herein may be used to treat a variety of disorders of the middle ear and/or inner ear including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, middle ear infections, and tympanic membrane perforations, to provide a few examples.

Some embodiments described herein include a system for precisely delivering a therapeutic agent to the cochlea of a patient. The system can include at least first and second tympanic membrane port devices, an endoscope, and an injector instrument. The first and second tympanic membrane port devices may be optionally configured to be removably implanted in laterally spaced apart positions in a tympanic membrane of the patient. The first tympanic membrane port device may define a first lumen and the second tympanic membrane port device may define a second lumen. Optionally, the endoscope may be slidable through the first lumen of the first tympanic membrane port device while the first tympanic membrane port is implanted in the tympanic membrane such that a distal end portion of the endoscope is positionable in a middle ear to visualize the round window region of a cochlea. The injector instrument, optionally, may be slidable through the second lumen of the second tympanic membrane port device while the second tympanic membrane port device is implanted in the tympanic membrane such that a curved distal tip portion of the injector instrument is advanceable to the round window region. The injector instrument may be configured to deposit the therapeutic agent at the round window niche, on the round window membrane, directly into the cochlea, or to other parts of the middle ear cavity; while the distal end portion of the endoscope is (optionally) in the middle ear laterally spaced apart from the injector instrument to provide visualization of the injector instrument.

Additional embodiments described herein include a system for injecting an otic treatment fluid into a round window niche adjacent to a cochlea of a patient. The system may include an inner ear injection device and an otic treatment fluid source. The inner ear injection device may include a proximal end and a flexible distal tip portion. Optionally, the flexible distal tip portion may be adjustable from a longitudinally straight shape during advancement through a tympanic membrane of the patient to a curved shape to orient a distal delivery port of the distal tip portion at a round window of the cochlea. Also, the otic treatment fluid source may be in fluid communication with the inner ear injection device so that the distal delivery port of the distal tip portion is configured to deposit the otic treatment fluid into the round window niche while the flexible distal tip portion is arranged in the curved shape.

In particular embodiments, a system may include a tympanic membrane port device having an access lumen. Additionally, the system may optionally include an inner ear tissue manipulator having a tissue engagement tip portion that is movable within a middle ear to modify a pseudomembrane at least partially covering a round window of an inner ear. In such implementations, the inner ear tissue manipulator may have a first shaft diameter configured to occupy a majority of the access lumen of the tympanic membrane port device and may be shaped to be advanced through the access lumen of the tympanic membrane port device in a tympanic membrane. The system may also optionally include an inner ear medicament injector having a steerable distal tip portion configured to access a region of the round window where the pseudomembrane was modified and to deposit a medicament into the round window niche adjacent to a round window membrane of a cochlea. In such implementations, the inner ear medicament injector may have a second shaft diameter configured to occupy a majority of the access lumen of the tympanic membrane port device and may be shaped to be advanced through the same tympanic membrane port device.

Other embodiments described herein include a method of treating hearing loss of a patient. The method may optionally include advancing a trocar needle carrying a first tympanic membrane port device into an outer ear of the patient, and creating a first puncture opening in a tympanic membrane of the patient using a distal tip portion of the trocar needle while the trocar needle is carrying the first tympanic membrane port device. Also, the method may include advancing the distal tip portion of the trocar needle through the puncture opening to implant the first tympanic membrane port device in the tympanic membrane, and the first tympanic membrane port device can define a first lumen therethrough. The method may optionally include advancing an injector instrument into the outer ear of the patient and the first lumen until a port defined by a distal tip of the injector instrument is near a round window niche of a cochlea of the patient. Further, the method may include injecting, via the injector instrument, a therapeutic fluid into the round window niche adjacent to a round window membrane of the cochlea. The therapeutic fluid may reside in the round window niche of the patient as a gel substance.

Additional embodiments described herein include a system comprising a middle ear visualization device deliverable through a tympanic membrane and having a distal end positionable in a middle ear to visualize a round window niche of the cochlea, and a treatment instrument deliverable through the tympanic membrane at a location spaced apart from the middle ear visualization device. The treatment instrument can be configured to treat at least one of: hearing loss, tinnitus, balance disorders, vertigo, Meniere's Disease, vestibular neuronitis, vestibular schwannoma, labyrinthitis, otosclerosis, ossicular chain dislocation, cholesteatoma, middle ear infections, and tympanic membrane perforations. In some embodiments, the system also includes at least one tympanic membrane port device insertable into the tympanic membrane to define a trans-tympanic membrane access lumen.

Some or all of the embodiments described herein may provide one or more of the following advantages. First, the systems and methods for treating hearing loss, and all other ear disorders as described herein, can include specialized techniques and instruments that can be used to access the round window niche of the cochlea and to precisely deliver a therapeutic formulation that is, or becomes, a gel. As compared to liquid therapeutic agents that tend to drain from the cochlea, the therapeutic formulation in gel form advantageously remains located adjacent to the round window membrane of the cochlea for an extended period of time during which the active ingredient of the therapeutic formulation can be gradually released into the perilymph (within the cochlea). As compared to liquid therapeutic agents, the therapeutic formulation in gel form in some cases requires precise placement in the round window niche to avoid affecting the mobility of middle ear structures like the ossicles, which could lead to temporary but severe conductive hearing loss. This type of extended release of the active ingredient thereby advantageously reduces the needed frequency of re-administrations of therapeutic agents. In addition, the overall efficacy of the treatment provided by the administration of therapeutic formulations in gel form tends to be greater than the administration of therapeutic formulations in liquid form due to longer middle ear residence and increased diffusion into the inner ear. The systems and methods for treating hearing loss, and all other ear disorders as described herein, can also include specialized techniques and instruments that can be used to access the round window niche of the cochlea and to precisely place a solid implant or sustained delivery system across on or across the round window membrane, or to directly deliver therapeutic treatments into the perilymph across the round window membrane. The systems and methods for treating hearing loss, and all other ear disorders as described herein, can also include specialized techniques and instruments that can be used to precisely deliver therapeutics to other parts of the middle ear cavity.

Second, the systems and methods for treating hearing loss described herein deliver into the cochlea a therapeutic formulation under direct visualization. The use of such direct visualization advantageously allows visual confirmation of the proper placement of the therapeutic formulation at the round window niche of the cochlea with a high level of accuracy. The direct visualization also provides additional benefits such as the ability to ascertain visually whether there are any obstructions of the round window that could inhibit the proper delivery of the therapeutic formulation. For example, in some cases the round window is covered by a pseudomembrane that can be altered or moved to allow improved access to the round window niche. By using the improved instrumentation described herein, the presence of the pseudomembrane can be visually verified, and thereafter physically altered or moved, so that improved and direct access to the round window niche can be visually verified. In addition, after the therapeutic formulation has been administered adjacent to the round window of the cochlea, direct visualization can be used to verify that the therapeutic formulation is retained in the desired position and manner.

Third, the systems and methods for treating hearing loss and other ear disorders as described herein allow direct access to the middle ear cavity through the tympanic membrane in a suture-less, low impact manner. In some implementations, such direct access through the tympanic membrane using tympanic membrane port devices can be safer, less invasive, and achieved with no sealing or patching of the tympanic membrane after removal of the tympanic membrane port devices. For example, due to the small size of the tympanic membrane port devices, the tympanic membrane can heal naturally after removal of the tympanic membrane port devices.

Fourth, the systems and methods for treating hearing loss and other ear disorders as described herein facilitate treatments in a minimally invasive fashion. Such minimally invasive techniques can tend to reduce recovery times, patient discomfort, and treatment costs. Moreover, the methods described herein can be performed using a local anesthetic rather than requiring general anesthesia. Accordingly, the treatment cost, patient risks, and recovery times are further advantageously reduced.

Fifth, the systems described herein can also be used for diagnostic purposes. Such uses can help in procedure planning, change site of care, and potentially improve patient outcomes.

Sixth, the systems and methods described here facilitate trans-tympanic or other visualization of the middle ear, which in turn can be used to diagnose disturbances to the structures of the middle ear, locate structures of the middle ear, locate structures at the junction with the inner ear, and guide access of instruments or therapeutics to desired structures in the middle or inner ear.

Seventh, some of the systems and methods described here facilitate trans-tympanic access of instruments or visualization tools to the middle or inner ear while locally reinforcing the tympanic membrane. This advantageous as a way to reduce tearing or damaging the tympanic membrane while manipulating visualization or access instruments during diagnosis or therapeutic intervention.

Eighth, some of the systems and methods described here facilitate access of instruments or visualization tools to the middle or inner ear while reducing pain or damage at the ear canal wall and tympanic membrane. Pain and discomfort associated with canal-based procedures often requires increasing levels of anesthesia or sedation, and which increases the need for specialized personnel, equipment and operating site. Damage to the ear canal wall is associated with a frequent high rate of bleeding due to its heavy vascularization, and such bleeding can slow or increase the difficulty of the procedure while also requiring additional instruments and therapeutic interventions.

Ninth, some of the systems and methods described here facilitate access of instruments or visualization tools to the middle or inner ear while providing stabilization or fixation against external ear structures or the tympanic membrane.

Tenth, some of the systems and methods described here facilitate healing, re-sealing, or hole-closure of the tympanic membrane after access or other perforation or damage to the tympanic membrane.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic illustration of a medical procedure for treating hearing loss, in accordance with some embodiments.

FIG. 2 shows a perspective view of a therapeutic gel substance residing within a cochlea and that was delivered via a round window of the cochlea in accordance with the procedure of FIG. 1.

FIG. 3 shows a perspective view of an example tympanic membrane port device mounted on a delivery trocar in accordance with some embodiments.

FIG. 4 shows a perspective view of the tympanic membrane port device of FIG. 3.

FIG. 5 shows a perspective view of an example endoscope instrument with a distal viewing tip that is configured to be advanced into the middle ear via the tympanic membrane port device of FIG. 3.

FIG. 6 shows a perspective view of an example membrane modification instrument that is configured to be advanced into the middle ear via the tympanic membrane port device of FIG. 3.

FIG. 7 shows a perspective view of an example therapeutic agent injector instrument that is configured to be advanced into the middle ear via the tympanic membrane port device of FIG. 3.

FIG. 8 shows a patient in position for the medical procedure for treating hearing loss and other ear disorders as described herein.

FIG. 9 shows the advancement of a sheath into the patient's outer ear toward the patient's tympanic membrane.

FIG. 10 shows the puncture of the patient's tympanic membrane and placement of a tympanic membrane port device in the patient's tympanic membrane.

FIG. 11 shows two tympanic membrane port devices implanted in the patient's tympanic membrane.

FIG. 16 shows the two tympanic membrane port devices in the patient's tympanic membrane (in accordance with FIG. 11) and an example endoscope device extending through a first one of the tympanic membrane port devices.

FIG. 17 shows the arrangement of FIG. 16 with an example forceps device extending through a second one of the tympanic membrane port devices.

FIG. 18 shows the forceps device of FIG. 17 extending toward a pseudomembrane covering a round window of the patient's cochlea.

FIG. 19 shows the forceps device of FIG. 17 grasping a portion of the pseudomembrane and pulling the pseudomembrane to create open access to the round window.

FIG. 28 shows an example endoscope device extending through an example tympanic membrane port device.

FIG. 29 shows an example forceps device extending through an example tympanic membrane port device. The forceps device is shown in an open configuration.

FIG. 30 shows an example forceps device extending through an example tympanic membrane port device. The forceps device is shown in a closed configuration.

FIG. 31 shows an example aspirating pick device extending through an example tympanic membrane port device.

FIG. 32 shows an example tissue spreader device extending through an example tympanic membrane port device.

FIG. 33 shows another example tissue spreader device extending through an example tympanic membrane port device.

FIG. 38 shows an example injection device extending through an example tympanic membrane port device and in a first configuration.

FIG. 39 shows the example injection device of FIG. 38 extending through an example tympanic membrane port device and in a second configuration.

FIG. 40 shows the example injection device of FIG. 38 extending through an example tympanic membrane port device and in a third configuration.

FIG. 41 shows another example injection device extending through an example tympanic membrane port device.

FIG. 42 show example cross-sections of an extendable injection tube of the injection device of claim 41.

FIG. 71 shows a distal end portion of another example endoscope.

FIGS. 72 and 73 show an example stabilization device.

Like reference symbols in the various drawings indicate like elements.

DETAILED DESCRIPTION OF ILLUSTRATIVE EMBODIMENTS

Figure 15:
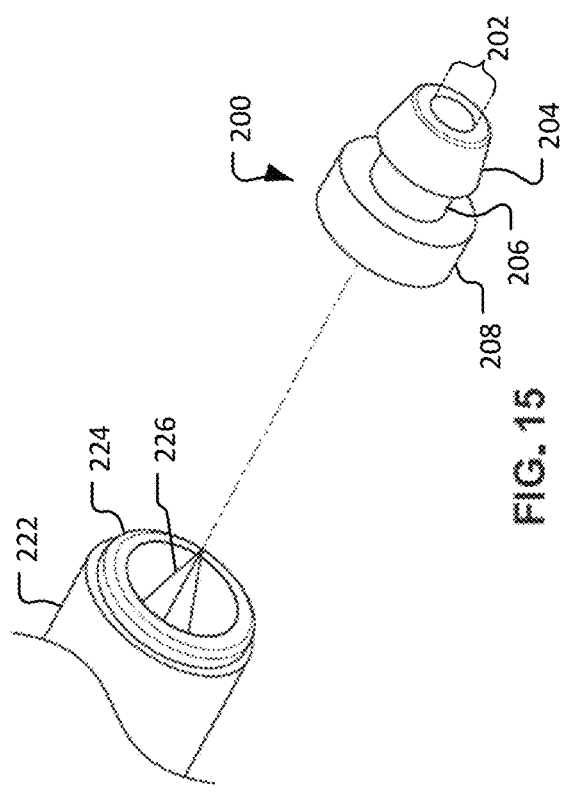
FIG. 15 shows a perspective view of the tympanic membrane port device of FIG. 13 separated from the sheath and delivery trocar.

Referring now to FIGS. 1-2, particular embodiments of systems and methods for treating a patient 10 can include an improved set of medical instruments for delivering a therapeutic formulation 100 to a targeted site at a cochlea 50 of the patient 10, for example, under direct endoscopic visualization. The devices, systems, and methods described herein can be used to treat and/or prevent a variety of conditions, including but not limited to hearing loss, including hidden hearing loss, noise-induced hearing loss, age-related hearing loss, drug-induced hearing loss (e.g., chemotherapy-induced hearing loss or aminoglycoside-induced hearing loss), sudden sensorineural hearing loss (SNHL), autoimmune inner ear disease, cholesteatoma, and the like.

While the devices, systems, materials, compounds, compositions, articles, and methods are described herein primarily in the context of treating hearing loss, it should be understood that devices, systems, materials, compounds, compositions, articles, and methods can also be used to treat any other disorder of the middle ear and/or inner ear including, but not limited to, tinnitus, balance disorders including vertigo, Meniere's Disease, vestibular neuronitis, vestibular schwannoma, labyrinthitis, otosclerosis, ossicular chain dislocation, cholesteatoma, middle ear infections, and tympanic membrane perforations, to provide a few examples.

This disclosure describes treatment methods and devices for treating the patient 10 using a minimally invasive approach. As depicted in FIG. 1, a clinician 1 approaches the cochlea 50 via the patient's 10 outer ear canal 20 using various instruments as described further below (collectively represented here by a generic instrument 110). The instruments 110 are advanced through the tympanic membrane (TM) 30, via one or more temporarily implanted tympanic membrane port devices 200. Distal end portions of the instruments 110 are thereby advanced into the middle ear 40 toward a round window 52 of the cochlea 50.

As described in more detail below, the instruments of the system can be configured to achieve a targeted delivery of the therapeutic formulation 100 into the round window niche 52 and adjacent to the round window membrane of the cochlea 50. The active ingredient of the therapeutic formulation 100 then moves passively by diffusion across the membrane of the round window 52, according to a concentration gradient, and into the perilymph (within the cochlea 50). In some embodiments, the therapeutic formulation 100 that is delivered adjacent to the round window membrane of the cochlea 50 can thereafter reside adjacent to or within the niche of the round window 52 as a semi-solid gel substance. As a gel substance, the delivery of the therapeutic formulation 100 will remain in the targeted site at the cochlea 50 so that the therapeutic formulation 100 can gradually release its active ingredient for an extended period of time such as days, weeks, or even months.

After the delivery of the therapeutic formulation 100, the instruments 110 and the one or more TM port device(s) 200 can be removed from the patient 10. The TM port device(s) 200 can be sized and shaped to that the openings of the TM 30 (in which the TM port device(s) 200 were positioned) can naturally heal (without suturing). The therapeutic formulation 100 (e.g., in gel form) will remain at the targeted site in the cochlea 50 to provide extended therapeutic effects by a controlled, sustained release of the active ingredient into the body of the patient 10.

Sustained release can encompass the release of effective amounts of an active ingredient of the therapeutic formulation 100 for an extended period of time. The sustained release may encompass first order release of the active ingredient, zero order release of the active ingredient, or other kinetics of release such as intermediate to zero order and first order, or combinations thereof. The sustained release may also encompass controlled release of the active ingredient of the therapeutic formulation 100 via passive molecular diffusion driven by a concentration gradient across a membrane or porous structure.

The procedure for delivering the therapeutic formulation 100 into the cochlea 50 of the patient 10 can be repeated periodically as needed for a particular patient's treatment. For example, in some cases deliveries of the therapeutic formulation 100 can be administered about every three to 24 months, each time using a new TM port device(s) 200 and delivery instruments as described herein. In particular cases, an assessment of the patient 10 can be performed to determine whether or when to administer more therapeutic formulation 100. In some cases, a procedure such as magnetic resonance imaging (MRI) (or other type of procedure) can be performed to help make such an assessment.

Referring also to FIGS. 3-7, an example system (or kit) of devices and instruments that can be used to perform the procedure to treat hearing loss and other ear disorders as described herein can include one or more of the following: (i) a TM port insertor 220, (ii) one or more TM port devices 200, (iii) an endoscope 300 (or other direct visualization instrument) sized to fit through the TM port device 200, (iv) a forceps 400 (or other type of tissue manipulator device as described further below) sized to fit through the TM port device 200, and (v) a injector instrument 800 that is sized to fit through the TM port device 200 and (optionally) includes a steerable distal tip. Other types of instruments may optionally be included such as, but not limited to, cannulas, curettes (single or double ended), elevators, forceps, hooks, luer lock connectors, needles, picks, knives, rasps, retractors, scissors, speculums, suction tubes, tissue nippers, side-biting scissors, and combinations thereof. Some of the instruments are deflectable or steerable. Some of the instruments can include suction, irrigation, and the like. In some embodiments, depth markers are included on the shaft of the instrument.

The endoscope 300, the forceps 400, and the injector instrument 800 are configured to access the middle ear 40 through the TM port devices 200 while each TM port device 200 is temporarily implanted in the TM 30 of the patient 10. That is, at least the distal end portions of each of the endoscope 300, the forceps 400, and the injector instrument 800 are configured to slidably pass through a lumen 202 defined by the TM port device 200 while the TM port device 200 is removably implanted in the TM 30. In cases that the endoscope 300, injector instrument 800, or any other instruments are of differing diameters or profiles, that the TM port devices 200 can be of different sizes or shapes to correspondingly accommodate. In some embodiments as described further below, the endoscope 300 (while its distal end portion is positioned in the middle ear 40) is used by the clinician 1 to obtain direct visualization as the clinician 1 manipulates another instrument, such as the forceps 400 or injector instrument 800, in the middle ear 40 to perform the treatment for hearing loss and other ear disorders as described herein.

During use, the proximal end portions of each of the depicted instruments remain external to the patient 10, and operable/controllable by the clinician 1. Each of the instruments, the TM port device 200, and the therapeutic formulation 100 are described further below.

Referring also to FIG. 8, the patient 10 is depicted in an example suitable position and orientation to receive the procedure(s) to treat hearing loss and other ear disorders as described herein. In some cases, the procedure can be performed with the patient 10 fully supine (as shown) or reclined in a chair.

The head of the patient 10 can be rotated to between about 30 to 45 degrees away from the clinician 1 (toward the opposite ear of the patient 10). The jaw of the patient 10 can be slightly elevated, and/or the external portion of the ear of the patient 10 may be pulled superiorly and backward to adjust the canal aperture and angularity. As such, the round window 52 of the patient will be oriented generally upward (e.g., away from the ground) so that, upon dispensation of the therapeutic formulation 100 from the delivery instrument, the therapeutic formulation 100 is able to pool at the round window 52 and not flow toward the eustascian tube or the ossicular chain.

In some implementations, the patient 10 remains awake during the procedure. That is, the procedure can be performed using a local anesthetic rather than a general anesthetic. For example, in some cases agents such as phenol or lidocaine can be applied to the TM 30 as a local anesthetic to facilitate the procedure. In some cases, the patient 10 can be given general anesthesia for the procedure.

Referring to FIG. 9, after prepping the patient 10 for the procedure, the TM port insertor 220 can be advanced into the outer ear canal 20 toward the TM 30 as part of the procedure of temporarily implanting a TM port device 200 in the TM 30. In some cases, an endoscope (not shown) is used in the outer ear canal 20 to provide direct visualization of the TM port insertor 220 as it is advanced and used to insert a TM port device 200 in the TM 30. In some cases, a microscope or other magnifying instrument is used to provide direct visualization of the TM port insertor 220 as it is advanced and used to implant the TM port device 200 in the TM 30.

Referring to also to FIGS. 12-15, the example TM port insertor 220 includes an elongate delivery sheath 222, a pusher catheter 224, and a trocar needle 226. The pusher catheter 224 is slidably disposed within a lumen defined by the delivery sheath 222. The trocar needle 226 is slidably disposed within a lumen defined by the pusher catheter 224. In particular embodiments, the pusher catheter 224 and the trocar needle 226 are a combined together as a single instrument.

When a TM port device 200 is operatively loaded onto the TM port insertor 220 (e.g., FIG. 13), the TM port device 200 is releasably coupled with the trocar needle 226, abutted against a distal end of the pusher catheter 224, and slidably disposable within the lumen of the delivery sheath 222. That is, at least a distal end portion of the trocar needle 226 is slidably disposed within the lumen 202 of the TM port device 200. In some embodiments, a clearance fit is used between the outer diameter of the distal end portion of the trocar needle 226 and the inner diameter of the lumen 202 of the TM port device 200. In particular embodiments, a slight interference fit is used between the outer diameter of the distal end portion of the trocar needle 226 and the inner diameter of the lumen 202 of the TM port device 200.

While the TM port device 200 is coupled with the trocar needle 226, the distal end face of the pusher catheter 224 is (or can be) abutted against the proximal end face of the TM port device 200. Accordingly, the pusher catheter 224 can apply a distally directed force against the TM port device 200 during the uncoupling, or to uncouple, the TM port device 200 from the trocar needle 226 (and from the TM port insertor 220 as a whole). Said simply, the pusher catheter 224 can be used to push distally the TM port device 200 off the trocar needle 226. Or, said another way, the pusher catheter 224 can counteract proximally directed force from the TM port device 200 as the trocar needle 226 is pulled proximally out of the lumen 202 of the TM port device 200.

The TM port device 200 is slidably disposable within the lumen of the delivery sheath 222. That is, the TM port device 200 can be removably contained within the lumen of the delivery sheath 222 (as in FIG. 12, in which the TM port device 200 is not visible because it is located inside of the delivery sheath 222). This arrangement can be used, for example, during advancement within the outer ear canal 20 of the TM port insertor 220 loaded with a TM port device 200 as depicted in FIG. 9.

The example TM port device 200 includes three conjoined, contiguous portions: (i) a distal end portion 204, (ii) a middle portion 206, and (iii) a proximal end portion 208. The lumen 202 runs centrally through each of the portions 204/206/208. In some embodiments, the lumen 202 has a diameter in a range of 0.4 mm to 0.6 mm, 0.5 mm to 0.75 mm, or 0.5 mm to 1.0 mm, without limitation.

The inner diameter or lumen of the proximal portion 208 can be tapered to have a larger diameter at the proximal end, creating a funnel shape to facilitate the alignment of instruments as they enter the port device.

The shape of the distal end portion 204 can be frustoconical. That is, the distal-most end of the distal end portion 204 has a smaller outer diameter than the proximal-most end of the distal end portion 204. The middle portion 206 and the proximal end portion 208 are each cylindrical. The outer diameter of the middle portion 206 is smaller than the outer diameters of each of: (i) the proximal-most end of the distal end portion 204 and (ii) the proximal end portion 208. Accordingly, the middle portion 206 can be considered a "waist region" of the TM port device 200 in this embodiment. The lumen 202 can be conical, cylindrical, oblong, pyramidal, or other shapes, as can the distal end portion 204.

As described further below, the middle portion 206 is where the tissue of the TM 30 will reside (at least primarily) while the TM port device 200 is implanted in the TM 30. The relatively smaller outer diameter of the middle portion 206 (as compared to the outer diameters of adjacent portions of the distal end portion 204 and the proximal end portion 208) will facilitate detainment of the TM port device 200 in the TM 30. In some embodiments, the outer diameter of the middle portion 206 is in a range of 0.25 mm to 0.75 mm, 0.25 mm to 1.0 mm, or 0.5 mm to 1.25 mm, without limitation. The longitudinal length of the middle portion 206 can be in a range of 0.1 mm to 0.3 mm, 0.1 mm to 0.5 mm, or 0.2 mm to 0.6 mm, without limitation. The outer diameter and length of the middle portion 206 is sufficient to receive the thickness of the TM 30 while preventing buckling, tearing, or other forces from being imparted inadvertently on the TM 30 upon insertion of the TM port device 200. In some embodiments, no waist region is included, and frictional fit between the distal section and TM is sufficient to hold the port device in the TM for the duration of a procedure while reducing forces TM is exposed to during port insertion or removal.

In some embodiments, the TM port device 200 can be implanted in the TM 30 without the use of a trocar needle. Instead, an incision in the TM 30 can be made first using a blade, needle, or laser. Then, the TM port device 200 can be implanted in the TM 30 by advancing the TM port device 200 into the incision.

While the TM port device 200 is implanted (or attached, coupled, engaged, etc.), to the TM 30, the TM port device 200 performs as a grommet, a stress relief member to prevent tearing of the TM 30, a middle ear access port, an instrument insertion tunnel, a working channel, and the like.

The TM port device 200 is configured and sized so that its removal from the TM 30 does not necessitate the use of sutures to seal the incision or fenestration formed in the TM 30 during insertion of the TM port device 200. Generally, a self-sealing fenestration through the TM 30 is no greater than about 2.5 mm in length, preferably between about 0.5 mm and 1.5 mm in length. Although the tools and methods described herein provide the advantage of suture-less access to the middle and/or inner ear, this does not preclude a surgeon from applying one or more closure techniques upon removal of the TM port device 200. That is, if the clinician 1 so desires, one or more techniques for closure of the fenestration(s) in the TM 30 can be performed.

The TM port device 200 can be formed of a material having a rigidity and strength to be inserted and removed from the TM 30 while also withstanding stresses that may arise during manipulation of surgical instruments inserted therethrough. In some embodiments, at least a portion of the TM port device 200 is formed of surgical metals such as stainless steel, titanium, platinum, Nitinol, and/or plastics such as polyimide, PEEK, fluoropolymers, silicone, and the like. In some embodiments, the inserted portion of the TM port device 200 can be formed of polyimide (or other rigid or semi-rigid polymers) and have a maximum outer diameter of no more than about 20 gauge (0.8 mm). One or more portions of the TM port device 200 can be coated with, or formed of, a resilient conformable material. For example, the retention feature 102 can be coated with or formed by over-molding with a material such as silicone or polyurethane.

Still referring to FIG. 9, in preparation for implanting the TM port device 200 in the TM 30, the TM port insertor 220 internally loaded with a TM port device 200 is advanced in the outer ear canal 20 toward the TM 30. During the advancement, the TM port insertor 220 can be configured as in FIG. 12, wherein the pusher catheter 224, the trocar needle 226, and the TM port device 200 are all within the lumen of the delivery sheath 222.

Figure 13:
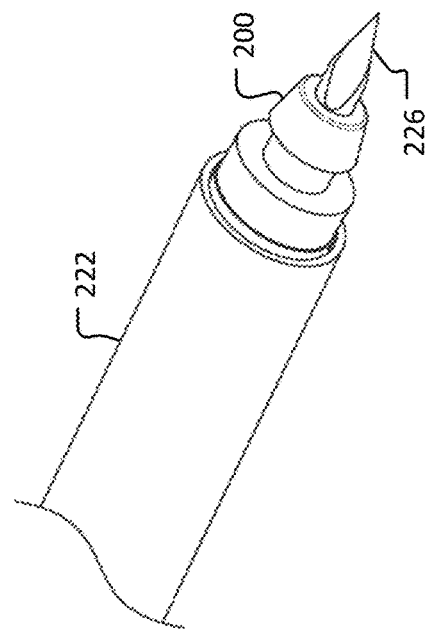
FIG. 13 shows a perspective view of the sheath of FIG. 12 with a tympanic membrane port device and a delivery trocar extending distally from the sheath.
Figure 14:
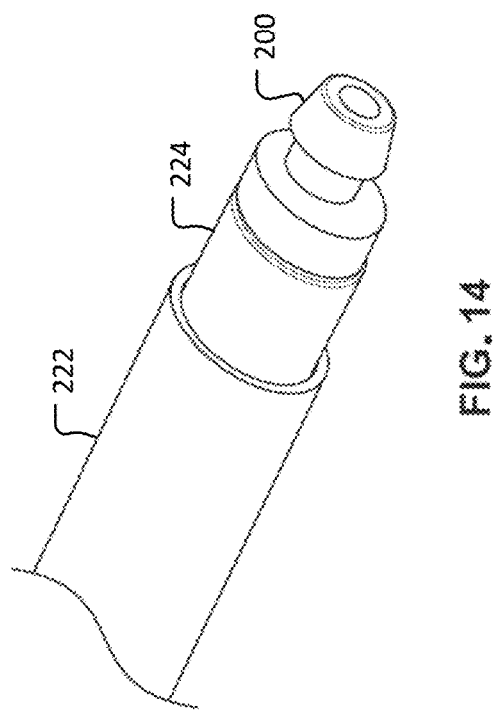
FIG. 14 shows a perspective view of the devices of FIG. 13 with the needle of the delivery trocar withdrawn proximally.
Figure 12:
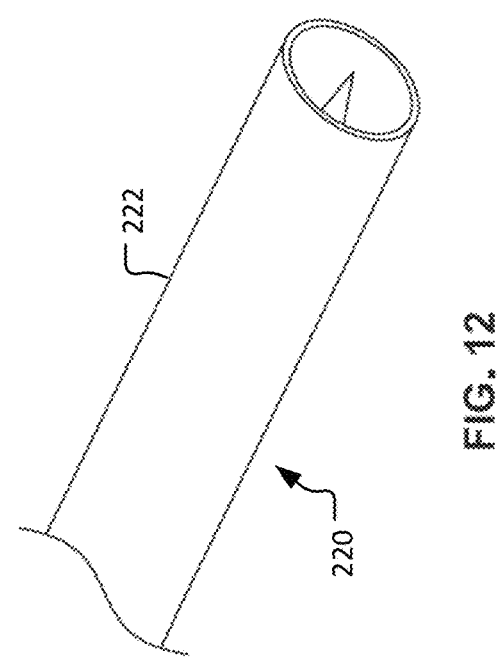
FIG. 12 shows a perspective view of a sheath that delivers a tympanic membrane port device.

Referring to FIG. 10, when the delivery sheath 222 has been advanced within the outer ear canal 20 to the extent that the distal end of the delivery sheath 222 is adjacent to the TM 30, the pusher catheter 224, the trocar needle 226, and the TM port device 200 can then be extended distally out from the interior of the delivery sheath 222 (as also depicted in FIG. 13). Since the distal tip portion of the trocar needle 226 is a beveled, sharp tip that is configured for puncturing the TM 30, the distal tip portion of the trocar needle 226 can be made to puncture the TM 30. As the pusher catheter 224 (and optionally the trocar needle 226) is extended farther distally, the distal end portion 204 (FIG. 15) of the TM port device 200 will enter and enlarge (dilate) the puncture of the TM 30 initially created by the trocar needle 226. Still farther advancement will position the middle portion 206 of the TM port device 200 in detained engagement with the TM 30. Then, as depicted in FIG. 15, the TM port insertor 220 can be withdrawn from the TM port device 200, leaving the TM port device 200 releasably coupled with the TM 30.

Referring to FIG. 11, one or more of the TM port devices 200 can be removably implanted in the TM 30. While implanted, the proximal end portions 208 of the TM port devices 200 are located in the outer ear canal 20, the distal end portions 204 of the TM port devices 200 are located in the middle ear 40, and the middle portions 206 of the TM port devices 200 receive the tissue of the TM 30. While implanted, the lumens 202 of the TM port devices 200 define open passageways between the outer ear canal 20 and the middle ear 40. In some embodiments, the passageways of the TM port devices 200 between the outer canal and middle ear can contain frictional elements, valves, or other elements to adjust the movement of instruments, gases, or liquids through passageways of the TM port devices 200.

As depicted, in some embodiments two of the TM port devices 200 are temporarily implanted in the TM 30. In such a case, the two TM port devices 200 can be laterally spaced apart from each other while implanted in the TM 30 (e.g., laterally with respect to the axes defined by the passageways of the TM port devices 200). In some embodiments, the two TM port devices 200 are laterally spaced apart from each other, while implanted in the TM 30, by a distance in a range of 0.5 mm to 8 mm.

Referring to FIG. 16, the TM port devices 200 are implanted in the TM 30 in order to provide access for instruments (such as the depicted endoscope 300) to extend therethrough and into the middle ear 40. The shaft of the endoscope 300 has an outer diameter that is smaller than the diameter of the lumen 202 (FIG. 15) of the TM port devices 200. Accordingly, the endoscope 300 can be slidably disposed through the lumen 202. While the endoscope 300 is extending through the TM port device 200 as shown, a distal end portion 310 of the endoscope 300 is positioned in the middle ear 40 where the distal end portion 310 can visualize the cochlea 50, including the niche of the round window 52. As shown, for example, in FIG. 28, the distal end portion 310 of the endoscope 300 can emit visual light and can receive images. In some embodiments, the endoscope 300 includes a fiber optic bundle that transmits light from a light source external to the patient 10 to the distal end portion 310 of the endoscope 300. In particular embodiments, one or more sources of light (e.g., one or more light emitting diodes) can be located in the distal end portion 310. The light emitted from distal end portion 310 illuminates the field of view within the middle ear 40 of the patient 10.

In some embodiments, as an alternative to the light source located adjacent the distal end of the endoscope 300, or in addition thereto, a light source can be positioned external to the TM 30 (in the outer ear canal 20) so as to increase the ability of a user to view instruments through translucent aspects of the TM 30 under illumination. Such a light source positioned external to the TM 30 can be used to illuminate the field of view within the middle ear 40 of the patient 10. In some such embodiments, an endoscope without a light source can then be utilized in the middle ear 40 (while the middle ear 40 is illuminated by the light source positioned in the ear canal external to the TM 30). In particular embodiments, the distal end of the endoscope may be located in the outer ear canal 20 near the TM 30 so that the camera of the endoscope 300 (or a camera of another type) can alternatively be positioned external to the TM 30. In such a case, the camera positioned external to the TM 30 (in the outer ear canal 20) can be used to provide enhanced viewability through the translucent aspects of TM 30 (when under illumination) and into the middle ear 40. Accordingly, in some cases just a single TM port device 200 would be implanted in the TM 30 to perform the procedures for treating ear disorders as described herein.

In some embodiments, as an alternative to the light source from the endoscope 300, or in addition thereto, a chandelier-type of light source (not shown) can be positioned in the middle ear 40 to illuminate the middle ear 40 in an ambient, overall manner. In some such embodiments, an endoscope without a light source can then be utilized in the middle ear 40 (while the middle ear 40 is illuminated by the chandelier-type of light source positioned in the middle ear 40).

Optionally, the TM port device 200 can be enhanced to include visualization features in some embodiments. For example, in some embodiments the TM port device 200 can be formed fully, or at least partially, from a light transmissive material so that the TM port device 200 can receive light at its proximal side and transmit light therethrough for emitting out the distal side and into the middle ear. In such a case, a source of light (e.g., a fiber optic, an LED, etc.) can be coupled to an outer wall of the TM port device 200 (e.g., at the proximal side). Light can be thereby transmitted into the middle ear 40 via the light-transmissive TM port device 200. In some cases, a light source can be positioned external to the TM 30 (in the outer ear canal 20) and the TM port device 200 can conduct light into the middle ear 40. Moreover, in some embodiments TM port device 200 can be enhanced to include a camera (or to be connectable to a camera) in a sidewall of the port device 200 so as to maintain availability of the central lumen for receiving other instruments. Accordingly, in some cases just a single TM port device 200 would be implanted in the TM 30 to perform the procedures for treating ear disorders as described herein.

Additionally, in some embodiments the endoscope 300 includes a second fiber optic bundle that transmits the images received at the distal end portion 310 to a viewing system external to the patient. The images are then displayed at viewing system for use by the clinician 1. In particular embodiments, a miniature camera (e.g., CCD-based) is located at the distal end portion 310. In some embodiments, a lens is included at the distal end portion 310. In particular embodiments, the endoscope 300 is a high-resolution widefield endoscope. In some embodiments, the endoscope 300 is steerable or deflectable in one or more planes. In any case, using the endoscope 300 slidably disposed through the lumen 202 of the TM port device 200, the clinician 1 can directly visualize at least the patient's cochlea 50 and region of the round window 52 during the performance of the procedure to treat hearing loss and other ear disorders as described herein. In some embodiments, the endoscope 300 defines one or more working channels through which instruments can be advanced and used.

Referring to FIG. 17, while the endoscope 300 is slidably disposed through a first one of the TM port devices 200, another instrument can be slidably disposed through a second one of the TM port devices 200. In the depicted arrangement, the forceps 400 is disposed through the second one of the TM port devices 200. A distal end portion 410 of the forceps 400 is thereby positionable within the middle ear 40.

Referring also to FIGS. 29 and 30, the distal end portion 410 of the forceps 400 can include a grasping mechanism. In the depicted embodiment, the distal end portion 410 includes a first jaw 412a and an opposed second jaw 412b. At least one of the jaws 412a-b is movable relative to the shaft of the forceps 400 so that materials such as tissues can be compressed or grasped between the jaws 412a-b and also released therefrom. That is, as shown in FIG. 29, the jaws 412a-b can be opened up such that there is space between the jaws 412a-b to receive materials. As shown in FIG. 30, the jaws 412a-b can be closed against each other to grasp materials. The movements of the jaws 412a-b can be actuated and controlled by the clinician 1 at the proximal end of the forceps 400 external to the patient.

While in the depicted embodiment only the second jaw 412b is movable relative to the shaft of the forceps 400, in some embodiments both the first jaw 412a and the opposed second jaw 412b are movable relative to the shaft of the forceps 400. In some embodiments, three movable jaws in a claw arrangement are included at the distal end portion 410. In some embodiments, the forceps 400 (and/or any of the other instruments described herein) includes one or more articulating portions by which the clinician 1 can controllably orient the distal end portion 410.

In the depicted arrangement, the endoscope 300 can be used to directly visualize at least the distal end portion 410 of the forceps 400. This functionality is useful to the clinician 1 because the clinician 1 may use the forceps 400 (and/or other instruments) for various purposes during the performance of the procedure to treat hearing loss and other ear disorders as described herein. The ability to visualize at least the distal end portion 410 of the forceps 400 (and/or other instruments) during use within the middle ear 40 helps facilitate precise positioning and functioning by the clinician 1 of the forceps 400 (and/or other instruments) during the procedure to treat hearing loss and other ear disorders as described herein.

While the instruments (e.g., the endoscope 300, the forceps 400, and any other instruments) are slidably positioned in the TM port devices 200, the clinician 1 can manipulate the positions and/or orientations of the instruments in relation to the patient 10 in various ways. For example, the longitudinal insertion depth of the instruments can be manipulated by the clinician 1. In some embodiments, one or more incremental depth markers (e.g., a distance indication scale) are included on the instruments. Such depth markings can be used to assist in preventing over-insertion or damage to ear structures. In addition, the instruments can be rolled by the clinician 1 around the longitudinal axes of the instruments. Still further, the pitch and/or yaw of instruments can be adjusted/tilted by the clinician 1. By so manipulating the positions and/or orientations instruments as desired, and while using direct visualization provided by the endoscope 300, the clinician 1 can perform the procedure to treat hearing loss with precision and care.

Referring also to FIGS. 18 and 19 (which are simulated images captured by the endoscope 300), in some cases (but not all cases) the patient 1 may have a pseudomembrane 51 covering all or a portion of the niche of the round window 52. In some cases, one or more other types of tissue may block access to the round window 52. When access to the round window 52 is partially or fully obstructed, the clinician can use the forceps 400 to open up access to the niche of the round window 52.

In the depicted example, the jaws 412a-b are opened up (FIG. 18) and the forceps 400 is advanced toward the pseudomembrane 51. When the jaws 412a-b are adjacent to, or in contact with, the pseudomembrane 51, the clinician can actuate the jaws 412a-b to close and capture a portion of the pseudomembrane 51 between the jaws 412a-b. Then, while the portion of the pseudomembrane 51 is held between the jaws 412a-b, the clinician can manipulate the forceps 400 (e.g., pull the forceps 400 proximally) to open up access to the round window 52 (FIG. 19). In some cases, the pseudomembrane 51 will be torn open (without removal of tissue) by such actions. In some cases, a portion of the pseudomembrane 51 may be removed (fully separated from surrounding tissues) by such actions.

The above descriptions and the corresponding figures explain how the forceps 400 can be used to gain access to the round window 52 (e.g., access to the round window niche and to the round window membrane) when one or more obstructions exist. In addition, there are other tissue manipulator instruments and/or techniques disclosed herein that can be used to gain access to the round window 52 when obstructions exist. These other tissue manipulator instruments and/or techniques also use the direct visualization provided by use of the endoscope 300. For example, FIGS. 20-23 illustrate how an aspirating device 500 can be used for such a purpose. In addition, FIGS. 24-27 illustrate how spreader device 600 or 700 can be used for such a purpose.

Figure 20:
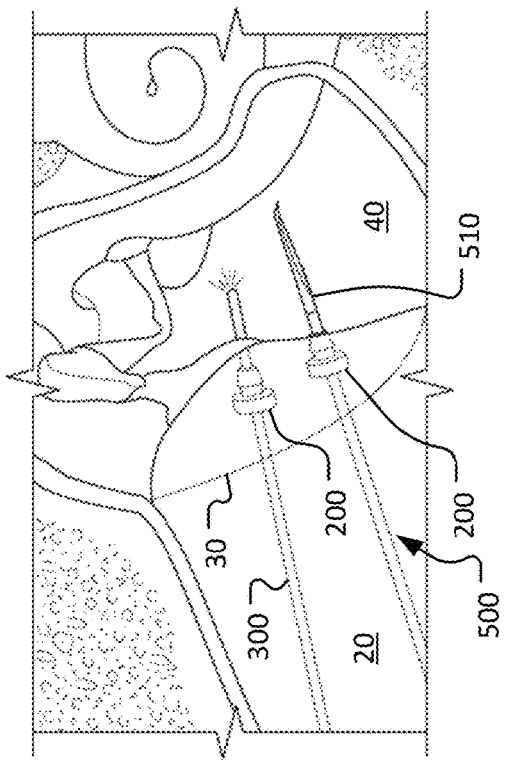
FIG. 20 shows the two tympanic membrane port devices in the patient's tympanic membrane (in accordance with FIG. 11) and an example endoscope device extending through a first one of the tympanic membrane port devices.
Figure 22:
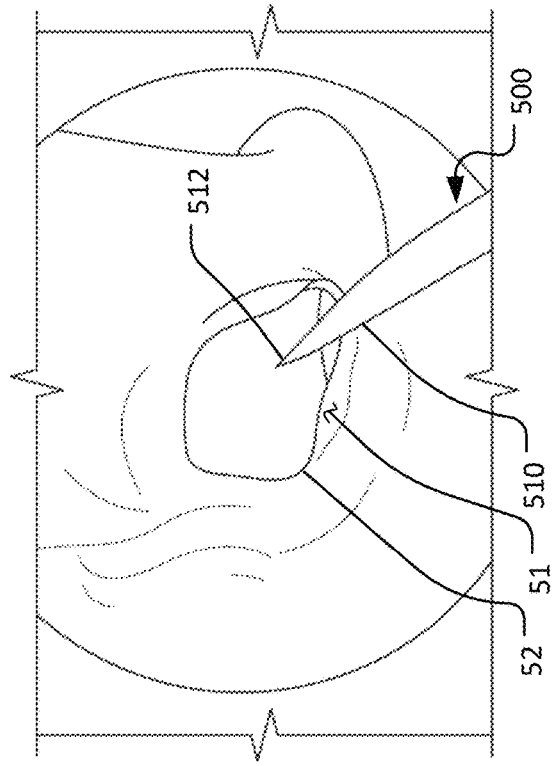
FIG. 22 shows the aspirating pick device of FIG. 21 extending toward a pseudomembrane covering a round window of the patient's cochlea.
Figure 21:
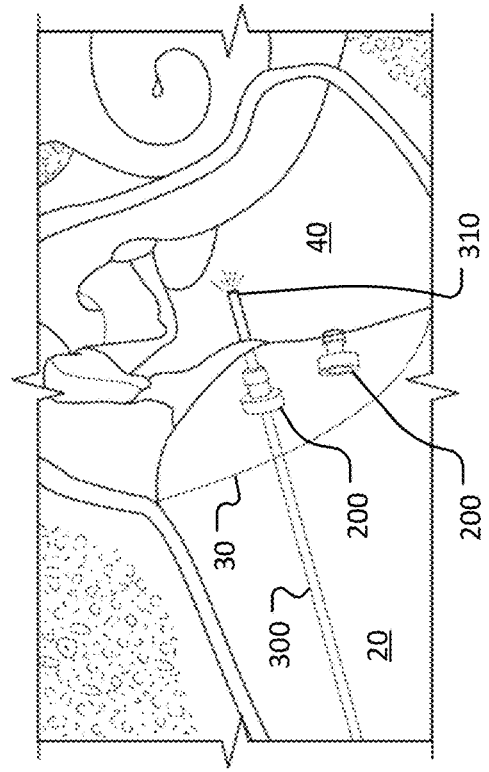
FIG. 21 shows the arrangement of FIG. 20 with an example aspirating pick device extending through a second one of the tympanic membrane port devices.
Figure 23:
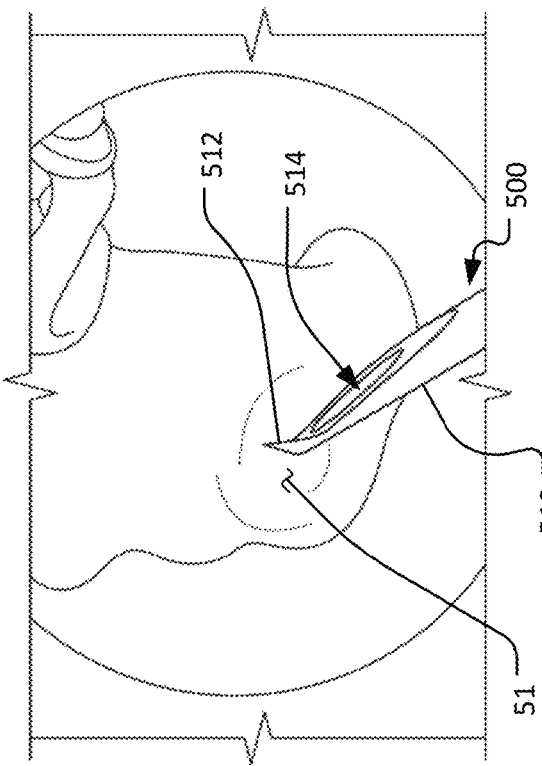
FIG. 23 shows the aspirating pick device of FIG. 21 pulling a portion of the pseudomembrane to create open access to the round window.

Referring to FIGS. 20-23, as described above in reference to FIG. 16 and shown here again in FIG. 20, at least the distal end portion 310 of the endoscope 300 can be slidably advanced into the middle ear 40 through the first one of the TM port devices 200. Another instrument can be slidably advanced through the second one of the TM port devices 200. As depicted in FIGS. 21-23, in this example the aspirating device 500 is disposed through the second one of the TM port devices 200. A distal end portion 510 of the aspirating device 500 is thereby positionable within the middle ear 40.

Referring also to FIG. 31, in some embodiments the distal end portion 510 of the aspirating device 500 can include a pointed tip member 512 and an aspiration port 514. The pointed tip member 512 can be used by the clinician 1 for various purposes such as, but not limited to, puncturing tissue, tearing tissue, dissecting tissues, retracting tissues, and the like. The aspiration port 514 can be used by the clinician 1 for applying suction to perform various tasks such as, but not limited to, removal of fluids, removal of particles, vacuum attachment to tissues for dissecting tissues, retracting tissues, stretching/tearing tissues, and the like.

FIG. 21 shows the distal end portion 510 of the aspirating device 500 being advanced within the middle ear 40 under the direct visualization of the endoscope 300.

FIG. 22 shows a simulated view from the endoscope 300 of the distal end portion 510 of the aspirating device 500 approaching the pseudomembrane 51.

FIG. 23 shows another simulated view from the endoscope 300 of the pointed tip member 512 and/or aspiration port 514 of the aspirating device 500 being used by the clinician 1 to tear open the pseudomembrane 51. With the pseudomembrane 51 torn open, access to the round window 52 is obtained (e.g., access to the round window niche and to the round window membrane).

Figure 24:
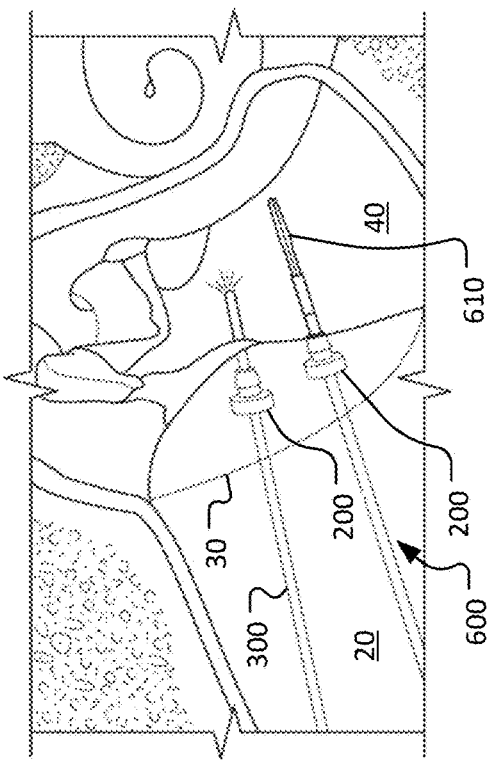
FIG. 24 shows the two tympanic membrane port devices in the patient's tympanic membrane (in accordance with FIG. 11) and an example endoscope device extending through a first one of the tympanic membrane port devices.
Figure 26:
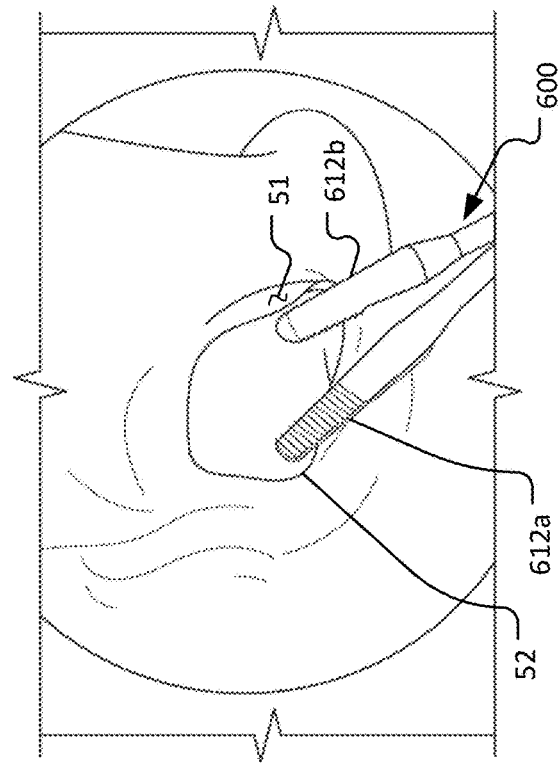
FIG. 26 shows the tissue spreader device of FIG. 25 extending toward a pseudomembrane covering a round window of the patient's cochlea.
Figure 25:
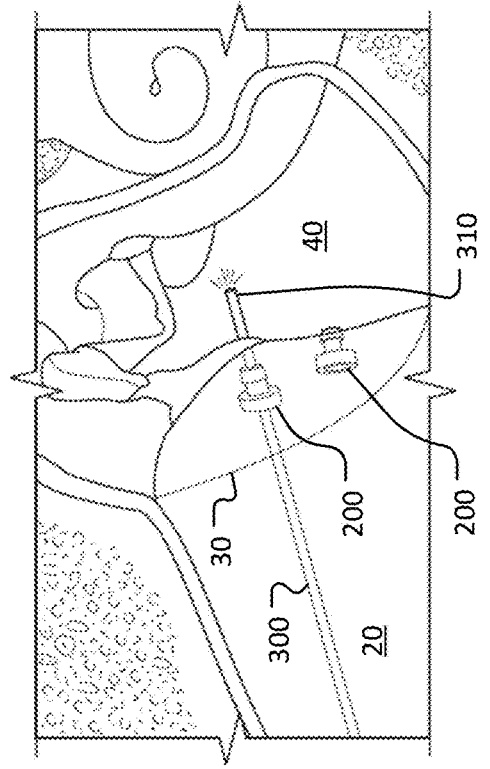
FIG. 25 shows the arrangement of FIG. 24 with an example tissue spreader device extending through a second one of the tympanic membrane port devices.
Figure 27:
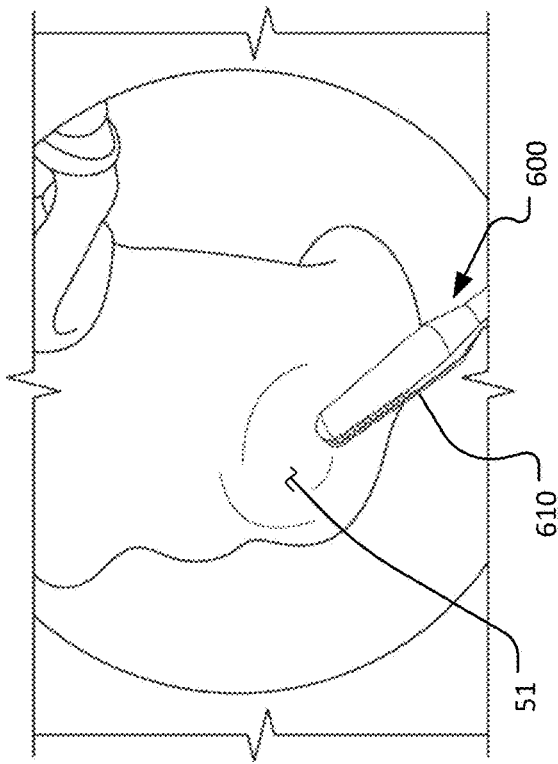
FIG. 27 shows the tissue spreader device of FIG. 25 separating a portion of the pseudomembrane to create open access to the round window.

Referring to FIGS. 24-27, as described above in reference to FIG. 16 and shown here again in FIG. 24, at least the distal end portion 310 of the endoscope 300 can be slidably advanced into the middle ear 40 through the first one of the TM port devices 200. Another instrument can be slidably advanced through the second one of the TM port devices 200. As depicted in FIGS. 25-27, in this example the spreader device 600 is disposed through the second one of the TM port devices 200. A distal end portion 610 of the spreader device 600 is thereby positionable within the middle ear 40.

Referring also to FIG. 32, in some embodiments the distal end portion 610 of the spreader device 600 includes a first splaying member 612a and an opposed second splaying member 612b. The splaying members 612a-b can be actuated by the clinician 1 to open/separate as shown in FIG. 32, and to close as shown in FIGS. 25 and 26. The splaying members 612a-b can thereby be used by the clinician 1 for various purposes such as, but not limited to, separating tissues, tearing tissue, dissecting tissues, pulling tissue, retracting tissues, and the like. In some embodiments, the distal tips of the splaying members 612a-b can be blunt, atraumatic tips as depicted.

FIG. 25 shows the distal end portion 610 of the spreader device 600 being advanced within the middle ear 40 under the direct visualization of the endoscope 300.

FIG. 26 shows a simulated view from the endoscope 300 of the distal end portion 610 of the spreader device 600 approaching the pseudomembrane 51.

FIG. 27 shows another simulated view from the endoscope 300 of the splaying members 612a-b of the spreader device 600 being used by the clinician 1 to spread and tear open the pseudomembrane 51. With the pseudomembrane 51 torn open, access to the round window 52 is obtained (e.g., access to the round window niche and to the round window membrane).

Referring to FIG. 33, another example embodiment of a spreader device 700 can be used to spread and tear open the pseudomembrane 51 in a manner that is very similar to that of the spreader device 600 described above. However, in contrast to the blunt, atraumatic tips of the splaying members 612a-b, the splaying members 712a and 712b of the spreader device 700 include pointed tip members 714a and 714b, respectively. The pointed tip members 714a-b, which can extend laterally at an angle from the axis of the spreader device 700 as shown, can be used to puncture tissues, such as the pseudomembrane 51. Thereafter, the splaying members 712a and 712b can be distally advanced and then actuated opened (as shown in FIG. 33) by the clinician 1 to spread apart the pseudomembrane 51 so that access to the round window 52 is obtained (e.g., access to the round window niche and to the round window membrane).

While the spreader device 700 includes splaying members 712a and 712b with the pointed tip members 714a and 714b extending angularly laterally, in some embodiments a side-biting scissors can be additional or alternatively used for the procedures described herein. Such a side-biting scissors can include two blades that are pivotable in relation to each other to shear tissue therebetween. In some embodiments, the pair of blades (or end portions thereof) can extend laterally at an angle (e.g., between 30° to 60°, or 20° to 80°, without limitation) from the axis of the scissors.

While a number of different instruments and techniques for removing obstructions to create access to the niche of the round window 52 are described above, in the case of some patients there are no such obstructions that need to be removed. Because of such patient-to-patient variations, the clinician 1 can first advance the endoscope 300 into the middle ear 40 via one of the TM port devices 200 and then visually inspect the middle ear 40 and cochlea 50 (including the region of the round window 52) to determine whether there are any obstructions that need to be removed to gain sufficient access to the niche of the round window 52. If there are obstructions (based on a visual inspection using the endoscope 300), one or more of the instruments and techniques for removing obstructions to create access to the niche of the round window 52 described above can be utilized. If there are no obstructions (based on the visual inspection using the endoscope 300), then the instruments and techniques for removing obstructions to create access to the niche of the round window 52 described above need not be performed. Accordingly, the use of the instruments and techniques for removing obstructions to create access to the cochlea 50 via the round window 52 can be used on an as-needed basis. As a point of reference, some estimates put the number of patients that have a pseudomembrane 51 covering the round window 52 at about 40% of all people.

Figure 34:
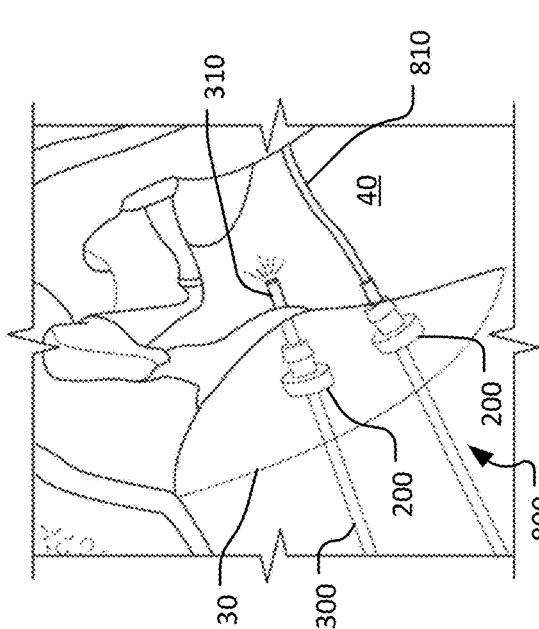
FIG. 34 shows the two tympanic membrane port devices in the patient's tympanic membrane (in accordance with FIG. 11), an example endoscope device extending through a first one of the tympanic membrane port devices, and an example injection device extending through a second one of the tympanic membrane port devices.

Referring to FIG. 34, when open access to the niche of the round window 52 has been verified and while the endoscope 300 is slidably disposed through a first one of the TM port devices 200, then the injector instrument 800 can be slidably advanced by the clinician 1 through the second one of the TM port devices 200. A distal end portion 810 of the injector instrument 800 is thereby selectively positionable within the middle ear 40 while being directly visualized using the endoscope 300. The injector instrument 800 will be used, as described below, to deliver the therapeutic formulation 100 in proximity to the round window 52 (e.g., into the round window niche adjacent to the round window membrane of the cochlea 50 from where the active ingredient of the therapeutic formulation 100 can move passively by diffusion across the membrane of the round window 52) or other target locations on or in the cochlea 50 of the patient 10.

Referring also to FIG. 41, the example injector instrument 800 is shown here in more detail. In the depicted embodiment, the injector instrument 800 includes a sheath 802 and an injection tube 820. The injection tube 820 is slidable within a lumen defined by the sheath 802. That is, the injection tube 820 can be selectively extended distally, by the clinician 1, from the distal end of the sheath 802 as depicted here. In addition, the injection tube 820 can be selectively withdrawn proximally, by the clinician 1, into the sheath 802 so that the injection tube 820 does not extend beyond the distal end of the sheath 802. When the injection tube 820 is extended (as shown), the exposed portion of the injection tube 820 makes up the distal end portion 810 of the injector instrument 800. The distal end portion 810 terminates at a distal tip 812 that defines a port through which the therapeutic agent, or medicament, is ejected.

The portion of the injection tube 820 that makes up the distal end portion 810 of the injector instrument 800 can have various shapes and form factors. For example, in the depicted example, the exposed injection tube 820 includes a linear portion 822, a first curved portion 824, and a second curved portion 826. The curved portions 824 and 826 become linear, however, when the injection tube 820 is constrained within the sheath 802. Alternatively, the curved portions 824 and 826 take on the shape of the lumen of the injection tube 820 if the lumen is not linear.

It can be said that the curved portions 824 and 826 have shape memory. That is, when the clinician 1 extends the curved portions 824 and 826 from the confines of the sheath 802, the curved portions 824 and 826 will revert to exhibiting curved shapes as shown.

In particular embodiments, the combination of the first and second curved portions 824 and 826 define an "S-shape" for the distal end portion 810 of the injector instrument 800. The S-shape is formed because the first curved portion 824 curves in an opposite direction in comparison to the curve of the second curved portion 826. Said another way, the center point of the radius of curvature of the first curved portion 824 is on an opposite side of the injection tube 820 as compared to the center point of the radius of curvature of the second curved portion 826. It should be understood that this shape of the injection tube 820 with the linear portion 822, the first curved portion 824, and the second curved portion 826 is just one example of a type of shape that the injection tube 820 can have. Other shapes are also envisioned and within the scope of this disclosure (such as, but not limited to, the shape shown in FIGS. 38-40 as described below).

It can be envisioned that as the clinician 1 begins to extend the injection tube 820 distally out from the distal end of the sheath 802, the second curved portion 826 will emerge first. Accordingly, the distal end portion 810 will initially have a single curve (as exhibited by the second curved portion 826). If the clinician 1 continues extending the injection tube 820 distally out from the distal end of the sheath 802, eventually the first curved portion 824 will begin to emerge. As the first curved portion 824 emerges, it can be envisioned that the entire distal end portion 810 will be correspondingly deflected in the opposite direction of the second curved portion 826.

As the injection tube 820 is extended out from the distal end of the sheath 802 to various extents, the distal tip 812 will be moved into various positions because of the shape memories of the first and second curved portions 824 and 826. Accordingly, the distal tip 812 is controllably positionable by the clinician 1 by controlling the extent to which injection tube 820 is extended out from the distal end of the sheath 802 and using the axial rotation of the instrument 800. Said another way, the clinician 1 can steer the distal end portion 810, and the distal tip 812 in particular, by controlling the extent to which injection tube 820 is extended out from the distal end of the sheath 802. This functionality can be used by the clinician 1 to position accurately the distal tip 812 in the round window 52 in preparation for injecting the therapeutic agent therefrom.

While the distal end portion 810 includes the first and second curved portions 824 and 826 that are curved in the same plane but in opposite directions, in some embodiments the distal end portion 810 can include two or more curved portions that are in differing planes.

In some embodiments, the shape of the distal end portion 810 can be selectively controlled by the clinician 1 using control members that are located within lumens defined within the wall of the injection tube 820. For example, FIG. 42 shows some example cross-sections (as taken along break line 42-42 in FIG. 41) of various types of tube configurations that the injection tube 820 can be made from. It can be seen, for example, that the tube 820a includes a first pair of lumens 821a and 821b that are 180° opposed to each other. In some embodiments, such lumens 821a-b can house control wires that are anchored, for example, near the distal tip 812. Accordingly, when the clinician 1 pulls proximally on one of the wires and relaxes the tension on the other opposed one of the wires, the distal end portion 810 will deflect in the direction of the tensioned wire. In this manner, the clinician 1 can steer the distal end portion 810 as desired.

Further, the example tube 820a also includes a second pair of lumens 823a and 823b. These lumens 823a-b define a plane that is perpendicular to the plane defined by the first pair of lumens 821a-b. Again, the second pair of lumens 823a-b can house control wires that are anchored, for example, near the distal tip 812. Accordingly, when the clinician 1 pulls proximally on one of the wires and relaxes the tension on the other opposed one of the wires, the distal end portion 810 will deflect in the direction of the tensioned wire.

If all four of the lumens 821a-b and 823a-b house such control wires, it can be envisioned that the clinician 1 can control the orientation, or steer, the distal end portion 810 to extend in any direction and to have any orientation as desired. Moreover, this can be true in either case of when the distal end portion 810 has shape memory that includes one or more curves (e.g., as depicted in FIG. 41) or when the distal end portion 810 is naturally linear.

While the example tube 820a has a particular arrangement of lumens 821a-b and 823a-b, the other example tubes 820b and 820c have other arrangements of lumens. Accordingly, tubes 820b and 820c, or tubes with any other arrangements of lumens, can also be used in accordance with the concepts described in the example context of the tube 820a.

In some embodiments, the lumens in the wall of the injection tube, such as the lumens 821a-b and 823a-b of the injection tube 820a, can house control members that are stiffening elements. Such stiffening elements can also be used to controllably deflect or steer the distal end portion 810. For example, in some embodiments the injection tube 820 naturally has one or more curves (e.g., the first curved portion 824 and the second curved portion 826). When stiffening elements (e.g., strong, bend-resistant linear shafts) are moved distally through the lumens in the wall of the injection tube 820 and into the regions of the curves, the curves will tend to straighten out. Conversely, when such stiffening elements are pulled proximally out from the regions of the curves, the curves will again reform. In such a manner using stiffening elements in the wall of the injection tube 820, the clinician 1 can control the orientation, or steer, the distal end portion 810 to extend in any direction and to have any orientation as desired. Conversely, in some embodiments the stiffening elements can have pre-formed curves (e.g., biased laser cut wires or hypotubes, shape memory elements or wires, or hypotubes made of materials such as nitinol) while the injection tube 820 is generally straight. Such stiffening members could be pushed distally relative to the relatively inflexible access shaft such that the stiffening member's curve imparts a curve to the injection tube's distal tip. It can be envisioned that stiffening elements with differing degrees of preset curves could be switched out to adjust curvature while allowing the injection tube 820 to remain in place and thereby limit potential disturbance of the TM 30. In another embodiment, the stiffening member can be a shape memory element (such as nitinol) that will take on its curve once exposed to elevated temperatures, such as those within the patient. In other embodiments, the elevated temperature could be greater than the patient's internal temperature. In such a case, the elevated temperature can be reached by applying voltage to the nitinol element, by exposure to heat generated by the light source, or by another technique for heating the nitinol element.

FIGS. 38-40 show another example injector instrument 900. In the depicted embodiment, the injector instrument 900 includes a sheath 902 and an injection tube 920. The injection tube 920 is slidable within a lumen defined by the sheath 902. That is, the injection tube 920 can be selectively extended distally, by the clinician 1, from the distal end of the sheath 902 as depicted here in FIGS. 39 and 40. In addition, the injection tube 920 can be selectively withdrawn proximally, by the clinician 1, into the sheath 902 so that the injection tube 920 does not extend beyond the distal end of the sheath 902 as depicted here in FIG. 38. When the injection tube 890 is extended (as shown in FIGS. 39 and 40), the exposed portion of the injection tube 920 makes up the distal end portion 910 of the injector instrument 900. The distal end portion 910 terminates at a beveled distal tip 912 that defines a port through which the therapeutic agent, or medicament, is ejected.

The injector instrument 900 can have any of the features that are described above in reference to the injector instrument 800 (including control members), except that the injection tube 920 of the injector instrument 900 has only a single naturally curved portion. Still, the extension direction and orientation of the distal end portion 910 (and of the distal tip 912) is substantially controllable by the clinician 1 by controlling factors such as the length of the distal end portion 910 and the roll, pitch, and yaw of the injector instrument 900 relative to the patient 1.

Figure 35:
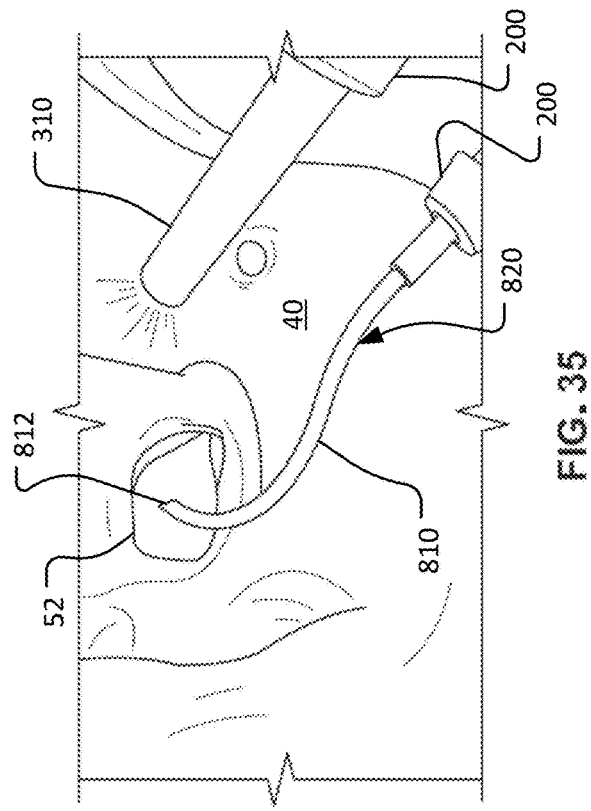
FIG. 35 shows the injection device of FIG. 34 extended and oriented in preparation for injecting a therapeutic agent into the round window of the patient's cochlea.

Referring now to FIG. 35, under the direct visualization of the endoscope 300 (of which the distal end portion 310 is visible here), the clinician 1 can controllably maneuver and orient the distal end portion 810 of the injection tube 820 so that the distal tip 812 is within, or adjacent to, the niche of the round window 52. To do so, the clinician 1 can use any of the techniques described above for deflecting, steering, articulating, extending, and otherwise orientating the distal end portion 810.

Figure 36:
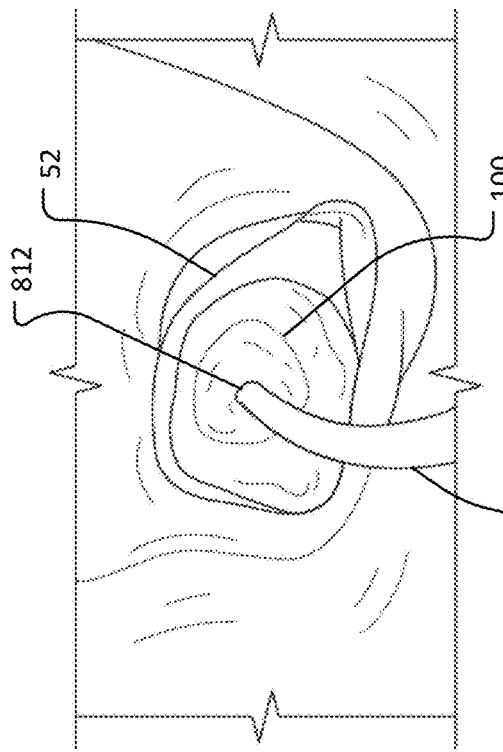
FIG. 36 shows the injection device of FIG. 34 delivering a dose of the therapeutic agent into the round window of the patient's cochlea.

Referring also to FIG. 36, when the distal tip 812 is properly positioned in relation to the round window 52 (this being confirmable by the clinician 1 using direct visualization of the endoscope 300), the clinician 1 can then deliver a desired amount the therapeutic formulation 100 into the round window niche adjacent the round window membrane of the cochlea 50. This delivery can also be performed under direct visualization using the endoscope 300. That is, the clinician 1 can use the endoscope 300 to confirm that the therapeutic formulation 100 has been delivered to a desired amount and in a desired position. Moreover, the clinician 1 can use the endoscope 300 to monitor, for a period of time, and that the therapeutic formulation 100 remains in the desired position rather than migrating away from the desired position.

The delivered therapeutic formulation 100 will tend to remain in the desired position because the therapeutic formulation 100 is delivered as, or will become in situ, a gel substance.

Figure 37:
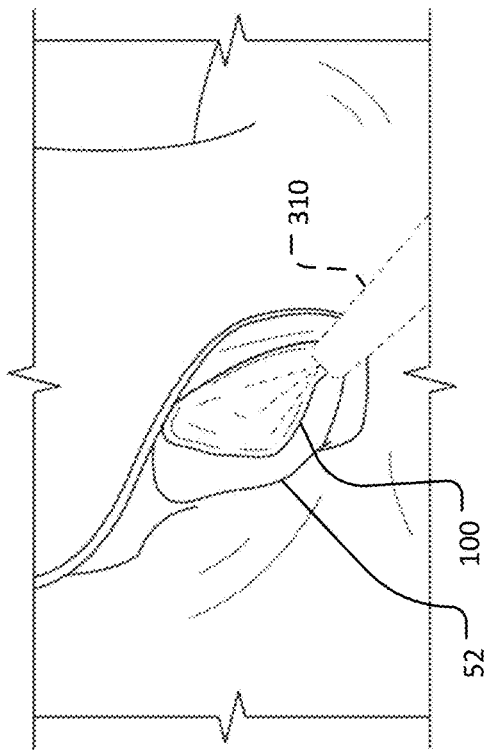
FIG. 37 shows an example light energy delivery device that is projecting light energy onto the therapeutic agent to photo-cure the therapeutic agent as a gel.

Referring to FIG. 37, in some embodiments the therapeutic formulation 100 can be cured or partially cured (to become a gel substance) in situ just after the therapeutic formulation 100 is delivered into the cochlea 50. In some such embodiments, light energy (e.g., UV light) to accelerate the curing of the therapeutic formulation 100 can be applied by the endoscope 300 as depicted, or by another instrument. In other embodiments, the therapeutic formulation 100 is a thermo-responsive hydrogel that is liquid at room temperature and forms a gel at body temperature.

Figure 43:
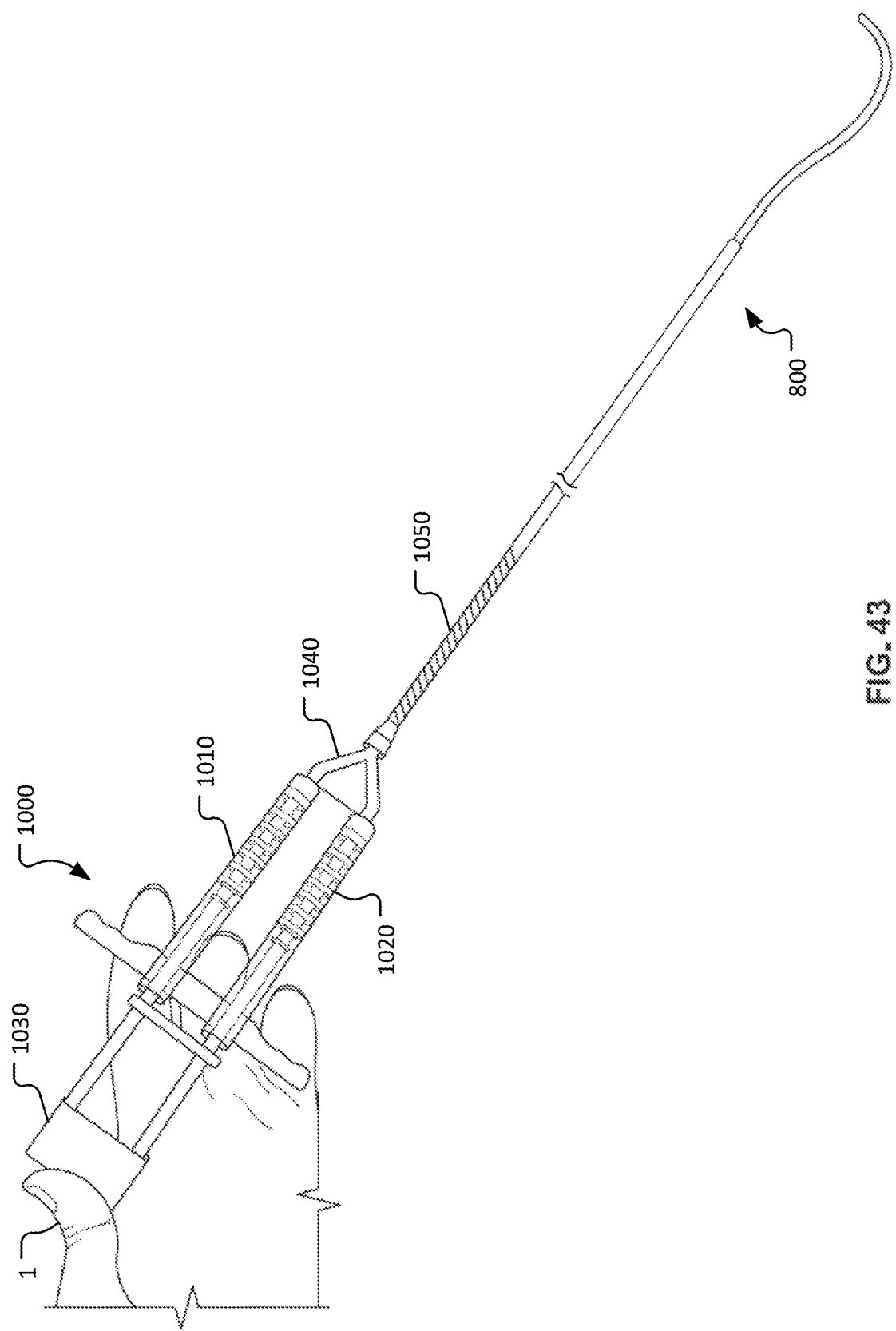
FIG. 43 shows an example therapeutic agent supply device coupled to the injection device of claim 41.

Referring to FIG. 43, in some embodiments, the therapeutic formulation 100 starts to become a gel substance when two liquid components are mixed together, such as by an example dual syringe 1000. The dual syringe 1000 mixes the two liquid components during the injection so that the two liquid components mix just prior to the delivery. The gelation reaction time between the two liquid components causes the homogeneous mixture of two liquid components to become a gel consistency rapidly, in keeping with the design of the dual syringe 1000.

The dual syringe 1000 includes a first barrel 1010, a second barrel 1020, a dual plunger 1030, a Y-connector 1040, and a static mixer 1050. The outlet of the static mixer 1050 is releasably coupled to an injector instrument, such as the injector instrument 800.

The first and second barrels 1010 and 1020 contain the first and second liquid components, respectively, and keep the first and second liquid components separate from each other while the first and second liquid components are in the first and second barrels 1010 and 1020. The dual plunger 1030 includes two plungers (one plunger in each of the first and second barrels 1010 and 1020) that are coupled together so that the displacement of the two plungers by the clinician 1 are synchronized during the injection. The Y-connector 1040 receives the first and second liquid components output from the first and second barrels 1010 and 1020 and directs the first and second liquid components to flow into contact with each other at the outlet of the Y-connector 1040. The static mixer 1050 receives the first and second liquid components from the Y-connector 1040 and causes the first and second liquid components to mix together to create a homogeneous mixture of the first and second liquid components. The homogeneous mixture of the first and second liquid components output from the static mixer 1050 is input into the injector instrument 800 from the homogeneous mixture of the first and second liquid components can be delivered adjacent to the cochlea 50 of the patient 10.

In another embodiment, a single syringe can be used to deliver the therapeutic formulation 100. In such a case, the gelation time of the formulation components of the therapeutic formulation 100 are tuned such that the formulation components can be mixed at patient bedside and immediately (before the crosslinking reaction of the formulation components or a majority of the crosslinking reaction takes place) delivered into the cochlea 50 using a standard single syringe attached to the injector instrument. Moreover, in some embodiments photo-crosslinking is used (e.g., FIG. 37). Accordingly, in some embodiments the delivery of the mixed formulation components into the niche of the round window 52 is promptly followed by application of light into the middle ear 40 toward the round window 52 to initiate and/or accelerate the crosslinking, and create the gel consistency of the therapeutic formulation 100. In some embodiments the gel consistency is generated upon exposure to heat produced by the patient's own body, or by another instrument.

The gel consistency of the therapeutic formulation 100 causes the therapeutic formulation 100 to remain adjacent to the round window membrane of the cochlea 50 and to facilitate either short term or sustained release of the active ingredient of the therapeutic formulation 100. Sustained release can encompass release of effective amounts of the active ingredient of the therapeutic formulation 100 for an extended period of time. The sustained release may encompass first order release of the active ingredient, zero order release of the active ingredient, or other kinetics of release such as intermediate to zero order and first order, or combinations thereof. The sustained release may encompass controlled release of the therapeutic formulation 100 via passive molecular diffusion driven by a concentration gradient across a porous structure.

A composition of the therapeutic formulation 100 can be a mixture. It can be a solution, a suspension, an emulsion, liquid, powder, a paste, aqueous, non-aqueous or any combination of such ingredients. A fluid is any composition that can flow. Fluids thus encompass compositions that are in the form of semi-solids, pastes, solutions, aqueous mixtures, gels, lotions, creams and other such compositions.

In some embodiments, an otic composition (e.g., an extended release otic composition) can be delivered to a subject from or with the help of the treatment devices described herein. In some embodiments, an extended release otic composition can include a polymer composition that can form a gel. For example, a polymer composition can include a functional polymer, wherein the functional polymer includes a first functional group, and a crosslinker, wherein the crosslinker includes a second functional group, and water, wherein a crosslinking reaction can occur between the first functional group and the second functional group to form a gel. In some embodiments, the functional polymer can be present in an amount of about 5% to about 15% by weight of the polymer composition. In some embodiments, the crosslinker can be present in an amount of about 0.2% to about 0.6% by weight of the polymer composition.

It will be appreciated that a first functional group (e.g., on a functional polymer) and a second functional group (e.g., on a crosslinker) should be such that a crosslinking reaction can occur. Therefore, the choice of functional polymer can be based on the choice of crosslinker, or vice versa. In some embodiments, a first functional group can be an N-hydroxysuccinimide (NHS) group and a second functional group can be an amine (e.g., a primary amine), or vice versa. In some cases, the functional polymer contains only electrophilic or nucleophilic functional groups, and the crosslinker contains only nucleophilic or electrophilic functional groups, respectively.

In some embodiments, the functional polymer is a multi-arm (e.g., 3-arm, 4-arm, 6-arm, or 8-arm) polyethylene glycol (PEG) including two more succinimidyl ester (e.g., a succinimidyl succinate or a succinimidyl glutarate) or sulfo-succinimidyl ester functional groups and the crosslinker contains a plurality of amine (e.g., primary amine) functional groups. In some embodiments, the multi-arm PEG can have two or more arms terminate in a succinimidyl ester functional group. In some embodiments, one or monomers of the multi-arm PEG can include a succinimidyl ester functional group. In some embodiments, the crosslinker can be a polylysine (e.g., an epsilon-polylysine) (e.g., trilysine, tetralysine, or pentalysine). For example, in some embodiments, the functional polymer can be pentaerythritol poly(ethylene glycol) ether tetrasuccinimidyl glutarate, and the crosslinker can be trilysine.

In some embodiments, the functional polymer is a multi-arm (e.g., 3-arm 4-arm, 6-arm, or 8-arm) polyethylene glycol including two or more amine (e.g., primary amine) functional groups and the crosslinker includes a plurality of succinimidyl ester (e.g., a succinimidyl succinate or succinimidyl glutarate) or sulfo-succinimidyl ester functional groups. In some embodiments, the multi-arm PEG can have two or more arms terminate in an amine (e.g., primary amine) functional group. In some embodiments, one or more monomers of the multi-arm PEG can include an amine (e.g., primary amine) functional group. In some embodiments, the crosslinker can be disuccinimidyl glutarate, disuccinimidyl suberate, bis(sulfosuccinimidyl)suberate, or disuccinimidyl succinate.

In some embodiments, an extended release otic composition can include an active agent (e.g., a therapeutic agent, a prophylactic agent, a diagnostic or visualization agent, or a combination thereof). An active agent can include, for example, a protein (e.g., an enzyme, a growth factor, an antibody or an antigen-binding fragment thereof), a carbohydrate (e.g., a glycosaminoglycan), a nucleic acid (e.g., an antisense oligonucleotide, an aptamer, a micro RNA, a short interfering RNA, or a ribozyme), small molecules, or combinations thereof. In some embodiments, a small molecule can include an antibiotic, an antineoplastic agent (e.g., doxorubicin), a local anesthetic, a steroid, a hormone, an apoptotic inhibitor (for example, an inhibitor of Apaf-1; see, e.g., U.S. Pat. No. 9,040,701, incorporated by reference herein in its entirety), an angiogenic agent, an anti-angiogenic agent (e.g., a VEGF inhibitor), a neurotransmitter, a psychoactive drug, an anti-inflammatory, and combinations thereof.

In some embodiments, an active agent can include an anti-angiogenic agent. In some embodiments, an anti-angiogenic agent can be a VEGF inhibitor. In some cases, a VEGF inhibitor can be an antibody or an antigen-binding fragment thereof, a decoy receptor, a VEGFR kinase inhibitor, an allosteric modulator of a VEGFR, or a combination thereof. In some cases, a VEGF inhibitor can be an antibody or an antigen-binding fragment thereof. For example, in some embodiments, a VEGF inhibitor can be alacizumab, bevacizumab (AVASTIN®), icrucumab (IMC-18F1), ramucirumab (LY3009806, IMC-1121B, CYRAMZA®), or ranibizumab (LUCENTIS®). In some embodiments, a VEGF inhibitor can be a decoy receptor (e.g., aflibercept). In some embodiments, a VEGF inhibitor can be a VEGFR kinase inhibitor, such as agerafenib, altiratinib, apatinib, axitinib, cabozantinib, cediranib, lapatinib, lenvatinib, motesanib, nintedanib, pazopanib, pegaptanib, rebastinib, regorafenib, semaxanib, sorafenib, sunitinib, toceranib, tivozanib, or vandetanib. Other examples of VEGF inhibitors may be known in the art. In some embodiments, a VEGFR inhibitor can be an allosteric modulator of a VEGFR (e.g, cyclotraxin B).

An extended release otic composition can, in some cases, be useful to treat an otic disease or disorder, such as Ménière's Disease (MD), Autoimmune Inner Ear Disease (AIED), sudden sensorineural hearing loss (SSNHL), noise-induced hearing loss (NIHL), age-related hearing loss, sensorineural hearing loss associated with diabetes, tinnitus, damaged cilia from an autoimmune disorder, damaged cilia from an infection, damaged cilia from excess fluid or pressure, hearing loss due to chemotherapy, or a combination thereof.

Therapeutics that can be delivered from or with the help of the treatment devices described herein can also include but are not limited to antioxidants, anti-inflammatories, steroids, antimicrobials, NMDA receptor antagonists, nootropics, anti-apoptotic agents, neurotrophins, neuroprotective agents, neural protective proteins such as CNTF, BDNF, PEDF, NGF, and the like, cannabinoids, monoclonal antibodies, other proteins, gene therapy, iRNA, tyrosine kinase inhibitors (TKIs), dual leucine zipper kinase (DLK) inhibitors, and protein therapies like anti-VEGF.

As an example, the therapeutic agent can include, but is not limited to antimicrobials such as antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluoromethalone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors; antioxidants, NMDA receptor antagonists, nootropics, anti-apoptotic agents, neurotrophins, neuroprotective agents, tyrosine kinase inhibitors (TKIs), dual leucine zipper kinase (DLK) inhibitors, cannabinoids, monoclonal antibodies, antibody fragments, other proteins, and gene therapy. Other therapeutic agents known to those skilled in the art which are capable of controlled, sustained release into the ear in the manner described herein are also suitable for use in accordance with embodiments of the devices described herein.

The therapeutic agent can include, but is not limited to sodium thiosulfate to protect against cisplatin-induced hearing loss; NMDA receptor antagonists for the treatment of tinnitus (AM-101; Auris Medical); AM-111 containing the synthetic peptide D-JNKI-1 (D-stereoisomer of c-Jun N-terminal Kinase Inhibitor 1; Auris Medical) for otoprotection in acute inner ear hearing loss; dexamethasone for the treatment of Meniere's Disease; D-methionine (Southern Illinois University) to protect against Noise-induced hearing loss; LY411575 (a selective gamma secretase inhibitor that blocks Notch activation); and NT-3 neurotrophic factor.

The therapeutic agent can include, but is not limited to local anesthetics for delivery into the ear canal including benzocaine, antipyrine, butamben, dibucaine, lidocaine, prilocaine, oxybuprocaine, pramoxine, proparacaine, proxymetacaine, and tetracaine.

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols including P407 and other combinations of polyethylene glycol and polypropylene glycol; aqueous media in the presence of a suspending agent, for example, sodium carboxymethylcellulose, hyaluronic acid, sodium hyaluronate, sodium alginate, poly(vinyl pyrrolidone) and similar compounds, either alone, or with suitable dispensing agents such as lecithin, cyclodextrins, polyoxyethylene stearate and the like. The carrier may also contain adjuvants such as preserving, stabilizing, wetting, emulsifying agents or other related materials.

A therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

Figure 44:
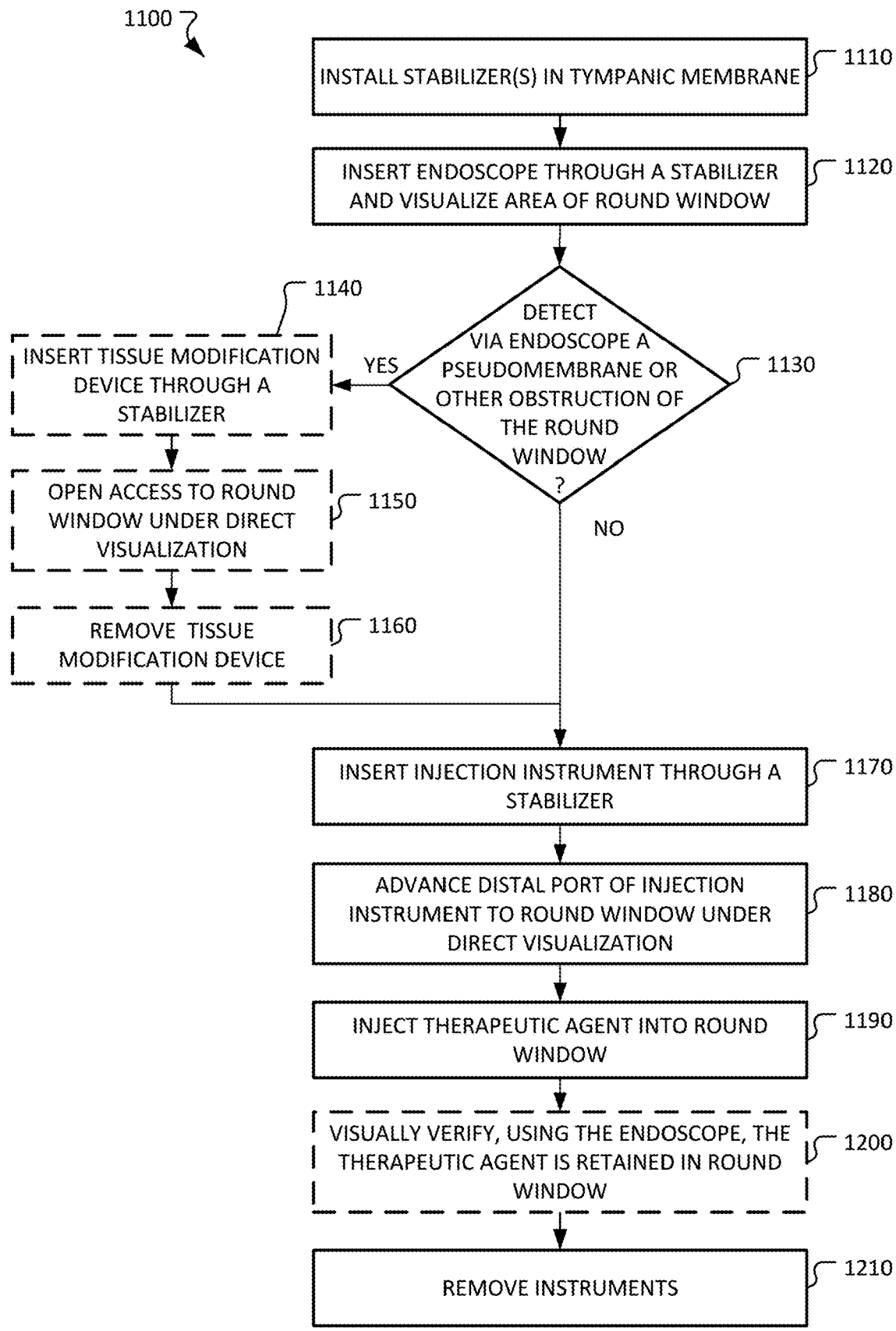
FIG. 44 is a flowchart of an example method for treating hearing loss in accordance with some embodiments.

Referring to FIG. 44, an example method 1100 of treating loss of a patient is depicted in the illustrated flowchart. The method 1100 can be performed by one or more clinicians, and results in the injection of one or more therapeutic agents into a cochlea of the patient. The method 1100 can be consistent with the techniques for treating hearing loss as described above, but is not limited as such.

The method 1100 is a minimally invasive procedure. In some cases, the method 1100 can be performed using a local anesthetic rather than requiring general anesthesia. In particular cases, the method 1100 can be performed using general anesthesia.

In operation 1110, one or more stabilizers are installed in the tympanic membrane (TM) of the patient. In some embodiments, the stabilizer(s) can be the TM port device 200 described above. Such a TM port device 200 can be installed using the TM port insertor 220 in the manner described above, for example. In some cases, a single stabilizer is installed in the TM. In particular cases, a total of two stabilizers are installed in the TM. In other cases, three or more stabilizers are installed in the TM. As described above, the stabilizers can perform as a grommet, a stress relief member to prevent tearing of the TM, a middle ear access port, an instrument insertion tunnel, a working channel, and the like.

In operation 1120, an endoscope is inserted through a stabilizer (while the stabilizer is implanted in the TM). When the endoscope is inserted through the stabilizer (e.g., a lumen defined by the stabilizer), a distal end portion of the endoscope is positioned in the middle ear. The endoscope can include a light source and image capture capability as described above in reference to endoscope 300. Accordingly, images of the middle ear and inner ear can be obtained using the endoscope and visualized by a clinician external to the patient either through the instrument itself, external displays, external heads up displays, 3D displays or similar. The clinician can manipulate the orientation and insertion depth of the endoscope to obtain images of various structures that are visible from within the middle ear. In some embodiments, the endoscope can be steerable or articulated to assist with such manipulation by the clinician.

In operation 1130, the clinician can use the endoscope to visualize potential obstructions to accessing the round window of the cochlea. From the images obtained using the endoscope, the clinician can then determine whether any obstructions are present that need to be alleviated in order to obtain sufficient access to the round window of the cochlea. For example, some patients may have a pseudomembrane covering the round window. In some cases, other tissues or obstructions may exist.

If the clinician determines there are no obstructions to the round window niche or other target locations of the cochlea that need to be alleviated, the method 1100 moves on to operation 1170. However, if the clinician determines that there are obstructions to the round window niche that need to be alleviated, the method 1100 moves on to operation 1140.

At optional operation 1140, the clinician inserts a tissue modification device into a second stabilizer (while the stabilizer is implanted in the TM). Concurrently, the endoscope also remains inserted through the first stabilizer. Accordingly, distal end portions of the tissue modification device and the endoscope are both within the middle ear (e.g., refer to FIGS. 17-19, 21-23, and 25-27). Various types of tissue modification devices can be selectively used by the clinician (e.g., the forceps 400, the aspirating device 500, the spreader devices 600 and 700, and the like).

At optional operation 1150, the clinician uses the inserted tissue modification device to open access to the round window niche of the cochlea. For example, the clinician can tear open and/or remove a portion of the pseudomembrane covering the round window niche if such a pseudomembrane is present. Other types of obstructions can be alleviated in a suitable manner by the clinician. These actions can be performed under direct visualization using the endoscope.

At optional operation 1160, the clinician removes the tissue modification device from the middle ear and from the stabilizer through which the tissue modification device was extending.

At operation 1170, the clinician inserts a therapeutic agent injection instrument through a stabilizer (while the stabilizer is implanted in the TM). Concurrently, the endoscope also remains inserted through the first stabilizer. In some embodiments, the endoscope may be used to "chase" the therapeutic agent injection instrument down the ear canal and provide visualization for inserting the therapeutic agent injection instrument through the stabilizer. So, in some embodiments the therapeutic agent injection instrument may be advanced ahead of the endoscope.

Accordingly, distal end portions of the injection instrument and the endoscope are both within the middle ear (e.g., refer to FIGS. 34-36). Various types of therapeutic agent delivery instruments can be selectively used by the clinician (e.g., the therapeutic agent injection instruments 800 and 900, and the like). Any of the features of the injection instruments 800 and 900 described above can be included in the injection instrument, in any combination. At this point, a source of the therapeutic agent can be coupled to the therapeutic agent injection instrument, or such a source can be coupled to the therapeutic agent injection instrument later (e.g., just prior to the injection thereof).

At operation 1180, the clinician advances the distal port of the therapeutic agent injection instrument into or adjacent to the niche of the round window. To do this, as described above, the clinician can controllably manipulate, steer, deflect, pan, roll, yaw, and control the insertion depth of the injection instrument in order to position the distal port of the therapeutic agent injection instrument into or adjacent to the niche of the round window. These actions can be performed under direct visualization using the endoscope.

At operation 1190, the clinician uses the injection instrument to deliver the therapeutic agent into the round window niche adjacent to the round window membrane or other target location on or adjacent the cochlea. These actions can be performed under direct visualization using the endoscope.

In some cases, two components of the therapeutic agent mix homogenously as a part of the injection step (e.g., as described in reference to FIG. 43). In particular cases, the therapeutic agent is mixed just prior to use and the mixture is delivered from a single reservoir (such as a syringe). In some cases, light energy (e.g., UV light) to accelerate the curing of the therapeutic agent can be applied by the endoscope, or by another instrument, in situ (e.g., as described above in reference to FIG. 37).

At optional operation 1200, the clinician can visually verify, using the endoscope, that the therapeutic formulation is retained in the round window niche of cochlea as desired. As described above, the therapeutic formulation is or soon becomes a gel substance such that the therapeutic formulation is intended to remain in the round window niche adjacent to the round window membrane of the cochlea as mass of the therapeutic agent. This aspect facilitates the controlled release of the active ingredient of the therapeutic formulation over a period of time. Accordingly, in this operation 1200 the clinician can take measures to confirm that the therapeutic agent remains as a mass in the cochlea as desired.

At operation 1210, the clinician can remove the instruments from the patient. The instruments to be removed may include the endoscope, injection instrument, and one or more stabilizers (e.g., TM port devices as described above). In order to facilitate removal of the stabilizer(s), in some embodiments the stabilizers have small physical features, such as tabs, on the proximal end that allow the stabilizers to be removed by readily grasping with forceps. Alternately, a removal tool can be used to pass through the lumen of the stabilizer and then "splay" open upon actuation. The removal tool can then be used to pull out the stabilizer from the TM.

Figure 45:
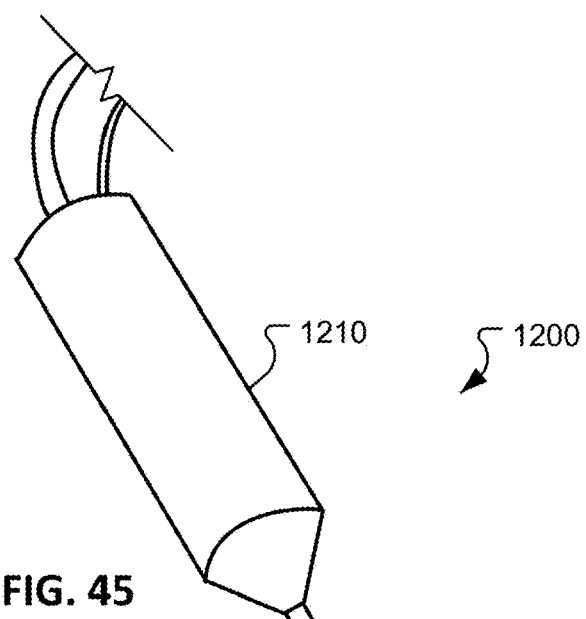
FIG. 45 shows an example otologic instrument with an optional removable sleeve device that defines a working channel coupled to the shaft of the instrument.

FIG. 45 shows an example otologic instrument 1200 that is engaged with an optional removable sleeve device 1300. The sleeve device 1300 includes a primary tube 1310 and one or more secondary tubes that define one or more auxiliary working channels 1320 that can receive an additional instrument, as described further below.

The sleeve device 1300 is removably coupled to the shaft 1220 of the instrument 1200. The sleeve device 1300 can have various configurations (as described further below) and can be slidingly engaged onto, and removed from, the shaft 1220 of the instrument 1200. The sleeve device 1300 can be made of metal (e.g., stainless steel, titanium, aluminum, etc.) or of a plastic material. In some embodiments, the sleeve device 1300 is transparent.

In the depicted embodiment, the otologic instrument 1200 is an endoscope with a handle 1210. However, the sleeve device 1300 can be used with various other types of otologic instruments as described herein, in addition to the depicted endoscope 1200. In one example arrangement using the sleeve device 1300, the instrument 1200 is an endoscope and an injector device can be extended through an auxiliary working channel defined by the sleeve device 1300. In some such embodiments, a distal tip portion of the injector device can have a natural curve such that the distal tip portion of the injector device can be controllably directed to a location that is non-linear with respect to the longitudinal axis of the auxiliary working channel.

The sleeve device 1300 can have various lengths in relation to the length of the shaft 1220. In some embodiments, the sleeve device 1300 will extend through a TM port device when in use. In some embodiments, the distal end of the sleeve device 1300 will be located proximal of the TM port device such that the sleeve device 1300 will not extend through the TM port device when in use.

In some embodiments, the central longitudinal axes of the primary tube 1310 and the one or more secondary tubes that define the one or more auxiliary working channels 1320 extend parallel to each other (e.g., as shown in FIG. 45). Alternatively, in some embodiments the central longitudinal axes of the primary tube 1310 and the one or more secondary tubes that define the one or more auxiliary working channels 1320 extend in a non-parallel relationship (e.g., a non-zero angle is defined between the primary tube 1310 and the one or more secondary tubes that define the one or more auxiliary working channels 1320). For example, in some embodiments an angle defined between the central longitudinal axes of the primary tube 1310 and the one or more secondary tubes that define the one or more auxiliary working channels 1320 is between 0° and 5°, or between 0° and 10°, or between 0° and 20°, or between 0° and 30°, or between 5° and 10°, or between 5° and 15°, or between 10° and 15°, or between 10° and 20°, or between 10° and 30°, without limitation. In some embodiments, the sleeve device 1300 can be adjustable so that a clinician can choose/customize the angle defined between the central longitudinal axes of the primary tube 1310 and the one or more secondary tubes that define the one or more auxiliary working channels 1320. In some embodiments this can be advantageous because it can reduce the effective diameter of the instruments crossing the TM by bringing the instrument that passes through the auxiliary working channel alongside the instrument or endoscope that is the central longitudinal axis and effectively removing any wall thickness between the two channels.

Figure 48:
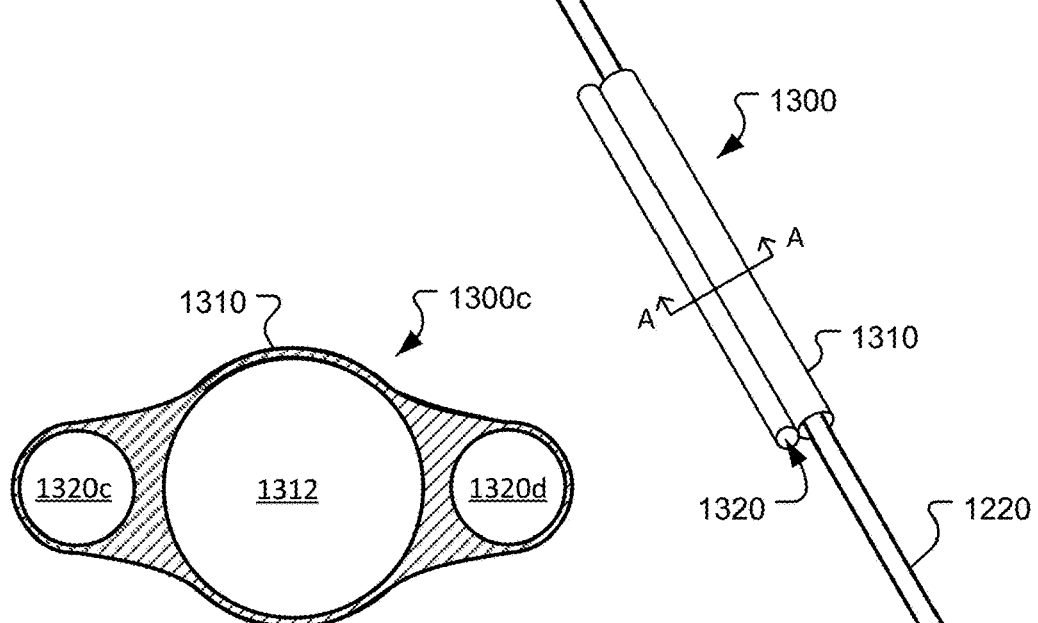
FIG. 48 shows another example transverse cross-sectional view of the removable sleeve device of FIG. 45.
Figure 46:
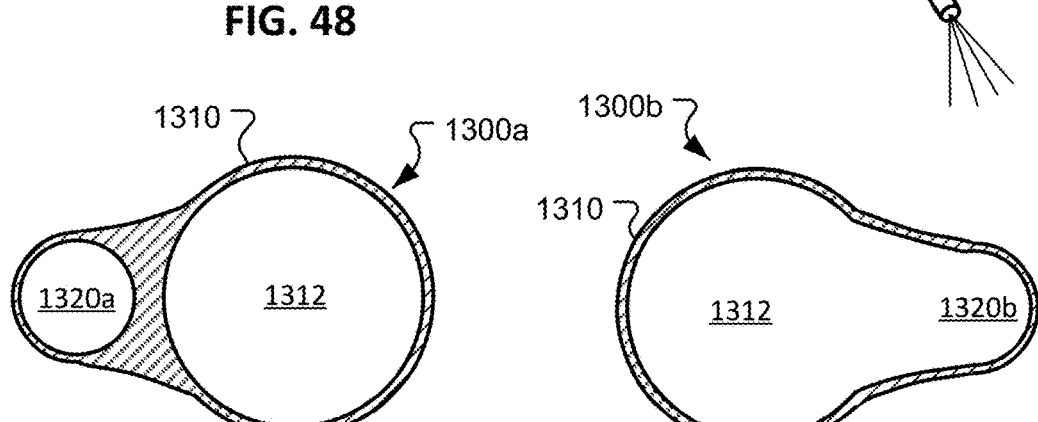
FIG. 46 shows an example transverse cross-sectional view of the removable sleeve device of FIG. 45.
Figure 47:
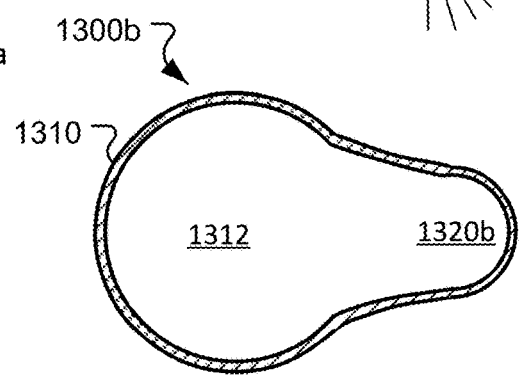
FIG. 47 shows another example transverse cross-sectional view of the removable sleeve device of FIG. 45.

FIGS. 46-48 are non-limiting example transverse cross-sectional views of the sleeve device 1300, taken at section A-A. FIG. 46 depicts a transverse cross-sectional view of a sleeve device 1300*a*. FIG. 47 depicts a transverse cross-sectional view of a sleeve device 1300*b*. FIG. 48 depicts a transverse cross-sectional view of a sleeve device 1300*c*.

Each of the sleeve devices 1300*a-c* includes the primary tube 1310 that defines a lumen 1312. The lumen 1312 is configured to slidingly receive the shaft 1220 of the instrument 1200 (as shown in FIG. 45). While the sleeve devices 1300*a-c* are slidingly coupled to the shaft 1220, the sleeve devices 1300*a-c* can be adjustably affixed at various locations along the length of the shaft 1220. In some embodiments, a mechanism that provides a light compression between sleeve devices 1300*a-c* and the shaft 1220 can be included to adjustably affix the sleeve devices 1300*a-c* at various locations along the length of the shaft 1220. For example, such a mechanism can comprise a collet, an annular elastomeric interface member, a wedge, a clasp, a clamp, and the like, without limitation.

The sleeve devices 1300*a-c* each define one or more auxiliary working channels that can receive and guide an additional instrument(s). For example, sleeve device 1300*a* (FIG. 46) defines a single auxiliary working channel 1320*a*. The sleeve device 1300*b* (FIG. 47) also defines a single auxiliary working channel 1320*b*. The sleeve device 1300*c* (FIG. 48) defines a first auxiliary working channel 1320*c* and a second auxiliary working channel 1320*d*.

The auxiliary working channel 1320*a* of the sleeve device 1300*a* is separated from the lumen 1312 by a material portion of the sleeve device 1300*a* as shown in FIG. 46. In contrast, the auxiliary working channel 1320*b* of the sleeve device 1300*b* is confluent (open, continuous) with the lumen 1312 as shown in FIG. 47. The auxiliary working channels 1320*c* and 1320*d* of the sleeve device 1300*c* are separated from the lumen 1312 as shown in FIG. 48. It should be understood that any arrangement and combinations of arrangements are envisioned and within the scope of this disclosure. The sizes and cross-sectional shapes of the auxiliary working channels 1320*a-b* can be made in any desired manner, without limitation.

Figure 49:
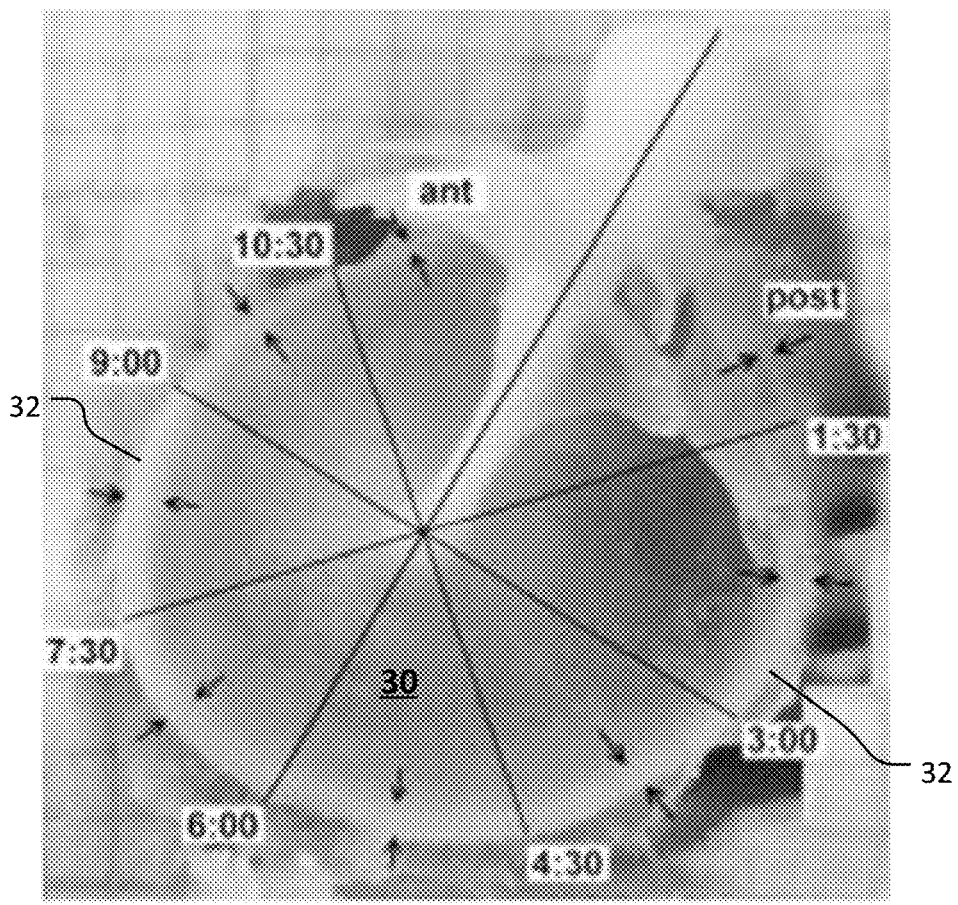
FIG. 49 illustrates a right tympanic membrane with overlaid lines and markings that indicate coordinates of locations around the tympanic annulus surrounding the tympanic membrane.

FIG. 49 illustrates a right TM 30 with overlaid lines and markings that indicate coordinates of locations around the tympanic annulus 32 surrounding the tympanic membrane 30. Locations on the tympanic annulus 32 can be identified using a clock face analogy with the malleus located at 12 o'clock, as shown.

The TM 30 is a thin, cone-shaped membrane that separates the external ear from the middle ear. The tympanic annulus 32 is a thicker fibrocartilaginous ring peripherally surrounding the TM 30. Accordingly, the tympanic annulus 32 provides a strong, stable tissue in which to anchor TM port devices.

Figure 50:
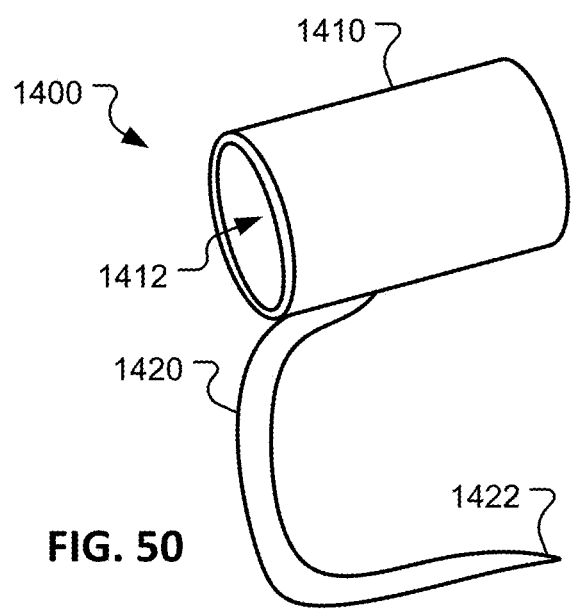
FIG. 50 shows an example tympanic membrane port device that includes an anchor portion.

FIG. 50 shows an example tympanic membrane port device 1400 that includes a laterally extending anchor portion 1420 attached to a cannula 1410. The cannula 1410 defines a port 1412 that serves as a passageway for instruments described herein.

As described further below, the cannula 1410 can be situated (implanted during the procedure and then removed) in the TM 30 (such that instruments can pass through the TM 30 via the port 1412 during the procedure) while the anchor portion 1420 is positioned in the tympanic annulus 32. In this manner, the strong tympanic annulus 32 can serve as a stable foundation to anchor the port device 1400. Accordingly, the anchor portion 1420 transfers stresses to the tympanic annulus 32 such that stresses to the TM 30 itself are minimized when instruments are used in the port 1412.

The anchor portion 1420 has a sharp, pointed tip 1422. The tip 1422 can pierce through the tympanic annulus 32 when the tympanic membrane port device 1400 is implanted in the TM 30 and the tympanic annulus 32. The lateral length of the anchor portion 1420 can be made to any desired length. The length of the anchor portion 1420 will help to define the resulting position of the cannula 1410 in the TM 30.

While the cannula 1410 is depicted as having a cylindrical outer profile, the cannula 1410 is not limited to such an outer shape. For example, in some embodiments the outer profile of the cannula 1410 can be as shown in FIG. 15 and elsewhere herein. In some embodiments, the outer profile of the cannula 1410 can be frustoconical, hourglass shaped, arcuate, and so on. The port 1412 can also have various cross-sectional shapes. In some embodiments, the port 1412 is curved, rather than linear as shown.

Figure 51:
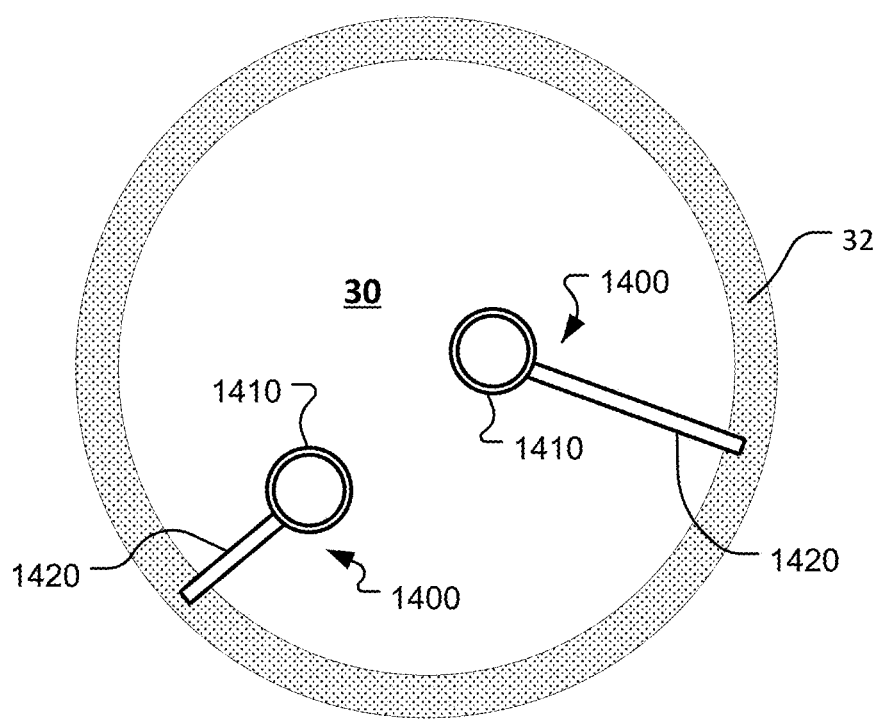
FIG. 51 shows a tympanic membrane and tympanic annulus with two tympanic membrane port devices of FIG. 50.

FIG. 51 shows a tympanic membrane 30 and tympanic annulus 32 with two tympanic membrane port devices 1400 implanted therein. It can be seen that the cannulae 1410 are positioned to provide a passageway through the TM 30, while the anchor portions 1420 extend to, and penetrate through, the tympanic annulus 32. Accordingly, the tympanic annulus 32 provides a strong, stable anchoring for the tympanic membrane port devices 1400.

It can be envisioned that the anchor portions 1420 could be used to attach or pierce other members, such as an elastomeric or hydrogel ring positioned overlaying the tympanic annulus 32. The elastomeric ring could be squeezed down the ear canal and placed at the tympanic membrane such that it expands back to shape at the periphery of the membrane overlaying the tympanic annulus, This removable member could then obviate the need for piercing or attaching directly to the tympanic annulus (and potential pain associated with that step) while still enabling stabilization and anchoring of the ports 1410.

Figure 52:
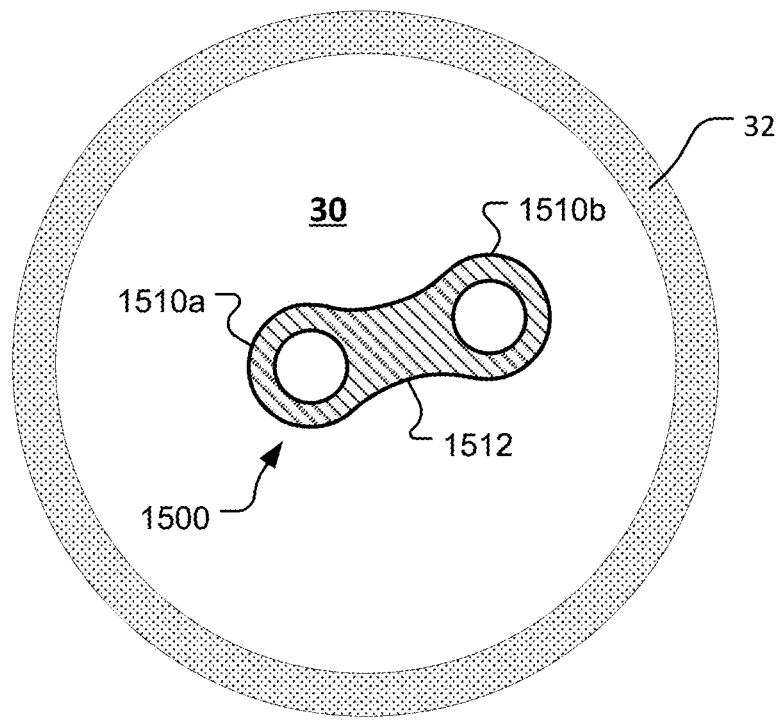
FIG. 52 shows a tympanic membrane and tympanic annulus with an example dual tympanic membrane port device.

FIG. 52 shows a tympanic membrane 30 and tympanic annulus 32 with an implanted example dual tympanic membrane port device 1500. The dual tympanic membrane port device 1500 includes a first tympanic membrane port device 1510*a* and a second tympanic membrane port device 1510*b*. Accordingly, two ports through the TM 30 are provided by the dual tympanic membrane port device 1500.

The tympanic membrane port devices 1510*a* and 1510*b* are connected to each other by a joining member 1512. The joining member 1512 can be any desired length to establish the center-to-center distance between the two tympanic membrane port devices 1510*a* and 1510*b*.

Figure 53:
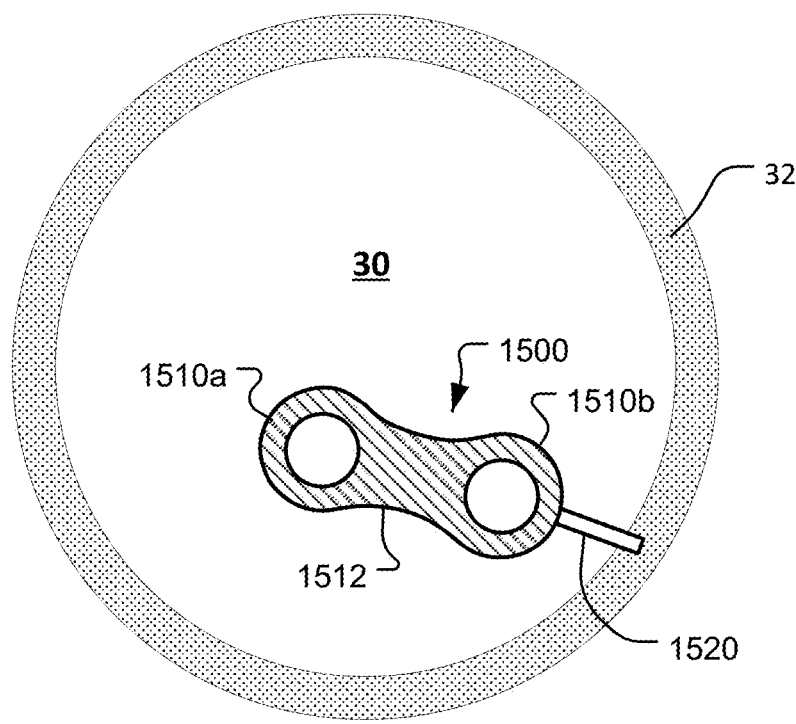
FIG. 53 shows a tympanic membrane and tympanic annulus with another example dual tympanic membrane port device.

FIG. 53 shows a tympanic membrane 30 and tympanic annulus 32 with another implanted example dual tympanic membrane port device 1500. In this example, the tympanic membrane port device 1500 includes an anchor portion 1520. The anchor portion 1520 laterally extends from the tympanic membrane port device 1510*b* and is pierced through the tympanic annulus 32 (e.g., as described above in reference to the anchor portion 1420 of the tympanic membrane port device 1400; FIGS. 50 and 51). It should be understood that the anchor portion 1520 can laterally extend in any desired direction from the dual tympanic membrane port device 1500. While the depicted dual tympanic membrane port device 1500 includes a single anchor portion 1520, in some embodiments two or more of the anchor portions 1520 can be attached to the dual tympanic membrane port device 1500. Accordingly, in some embodiments the dual tympanic membrane port device 1500 can be anchored at two or more locations of the tympanic annulus 32 (in addition to passing through the TM 30 at two locations).

Figure 54:
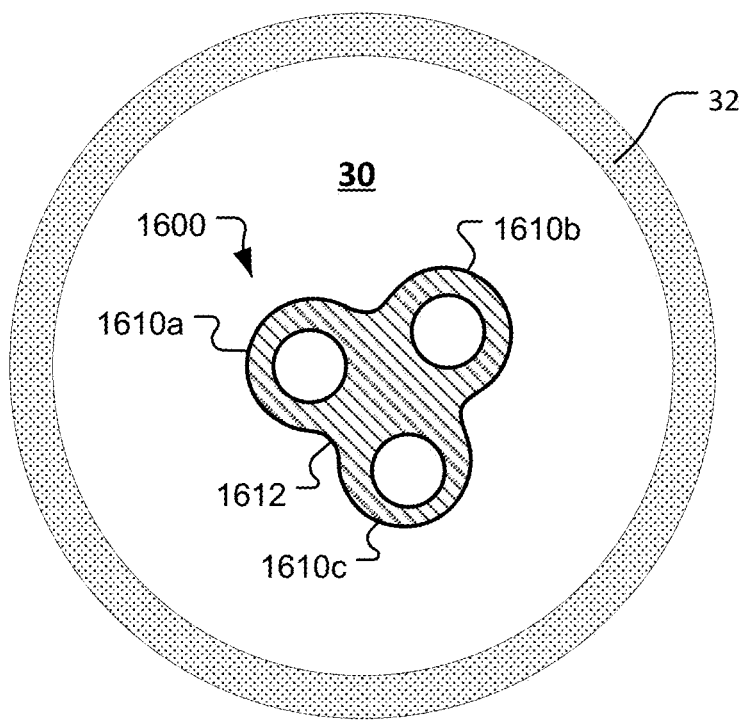
FIG. 54 shows a tympanic membrane and tympanic annulus with an example triple tympanic membrane port device.

FIG. 54 shows a tympanic membrane 30 and tympanic annulus 32 with an example triple tympanic membrane port device 1600. The triple tympanic membrane port device 1600 includes a first tympanic membrane port device 1610*a*, a second tympanic membrane port device 1610*b*, and a third tympanic membrane port device 1610*c*. Each of the tympanic membrane port devices 1610*a-c* defines a port through the TM 30.

The tympanic membrane port devices 1610*a-c* are interconnected via a joining member 1612. The joining member 1612 can be any desired shape and length to establish the center-to-center distances between the three tympanic membrane port devices 1610*a-c*. In some embodiments, one or more anchor portions (e.g., like the anchor portion 1520; FIG. 53) can be attached to the triple tympanic membrane port device 1600 to facilitate anchoring of the triple tympanic membrane port device 1600 in the tympanic annulus 32.

In some cases, the third port device could instead be a lens to allow trans-tympanic membrane viewing of the middle ear through the operating microscope. This would obviate the need for an endoscope and free a surgeon's hand and allow for binocular visualization. This lens could be convex to allow for widefield viewing not otherwise possible with the external microscope alone.

Figure 55:
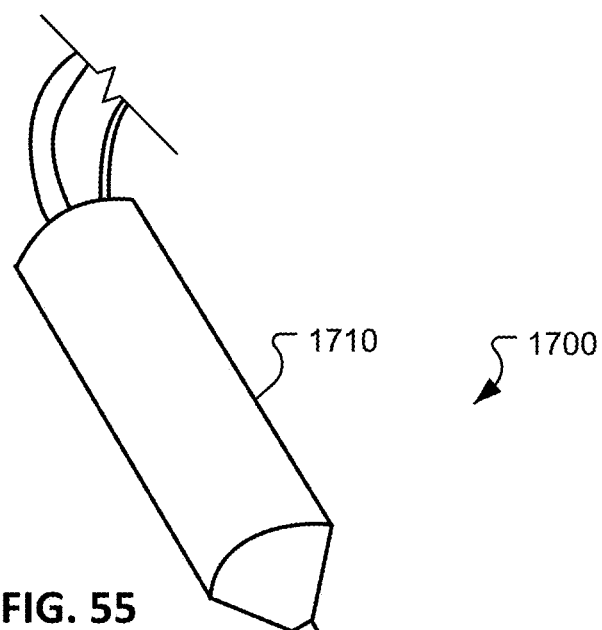
FIG. 55 shows an example endoscope instrument.

FIG. 55 shows an example endoscope instrument 1700. The endoscope instrument 1700 has a field of view that extends from the tip at an angle $\alpha$. The endoscope instrument 1700 can be used, for example, trans-tympanically to visualize middle ear and inner ear structures as described above.

In some cases it would be beneficial to widen the field of view of the endoscope instrument 1700. For example, while the tip of the endoscope instrument 1700 is in the middle ear it would be beneficial to widen the endoscope's field of view because of the small and irregular shape of the middle ear.

Figure 56:
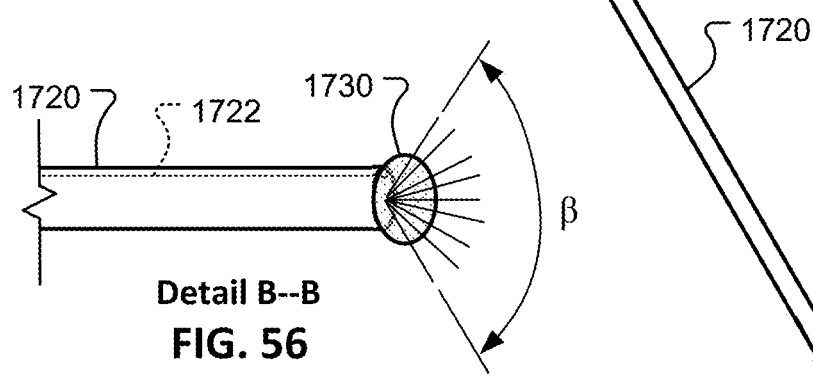
FIG. 56 shows an example tip portion of the endoscope instrument of FIG. 55 with a liquid lens.

FIG. 56 shows that a liquid lens 1730 can be selectively created at the tip of the endoscope instrument 1700 to widen the field of view to an angle $\beta$ (where $\beta > \alpha$). Such a liquid lens 1730 can be selectively created when the tip of the endoscope instrument 1700 is in the middle ear, for example. Refraction at the boundary of the liquid lens and air creates the lens' optical effect.

The shaft 1720 can define a lumen 1722 through which a liquid can be delivered to the tip of the shaft 1720 to temporarily create the liquid lens 1730. The liquid can be, for example, a high refractive liquid with known surface tension to create a precisely-sized drop at end of endoscope instrument 1700. The size of the drop can also be selectively adjusted to make adjustments of the field of view (to adjust the angle $\beta$). The liquid lens 1730 can be shaken or wiped off on a tissue structure to eliminate it, for example.

Figure 57:
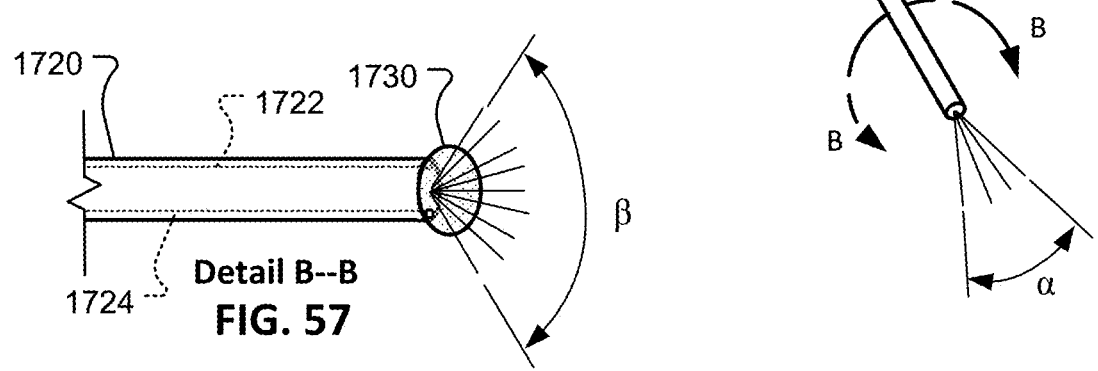
FIG. 57 shows another example tip portion of the endoscope instrument of FIG. 55 with a liquid lens.

FIG. 57 is another example embodiment that includes the lumen 1722 and a second lumen 1724. The second lumen 1724 can be used to aspirate the liquid of the liquid lens 1730 to make the drop size smaller, or to eliminate the liquid lens 1730. As an example benefit, the lens can be renewed to remove any contamination from bleeds or procedures which would interfere with the view.

In some cases, otologic procedures are performed while the space is flooded with a liquid. For example, in some cases otologic procedures are performed while the middle ear and/or outer ear is flooded with a liquid. In such a case, the endoscope instrument 1700 can have an air bubble at the tip of endoscope 1700 in fluid-filled chamber in order to widen the field of view of the endoscope 1700.

In some embodiments, the middle ear can be visualized by an endoscope that captures images through the TM 30. That is, the distal end of the endoscope can reside in the ear canal 20, and images of the middle ear 40 can pass through the TM 30 and be captured by the endoscope residing in the ear canal 20. In some cases, the images can be enhanced when an interface liquid is used between the lens at the tip of the endoscope and the TM 30. For example, fluids such as Healon (sodium hyaluronate), silicone oil, glycerol, or hydroxyproply methylcellulose have been shown to perform well for enhancing the image quality.

In some embodiments, the lens of the endoscope can be configured to enhance its ability to retain the interface liquids. For example, the perimeter can have a rim or lip to help with the retention of the interface liquids. In some embodiments, a supply of the interface liquid can be delivered (continuously or intermittently as controlled by a clinician) to the tip of the endoscope using a lumen of the endoscope.

Referring to FIGS. 58-64, particular embodiments of systems and methods for treating an ear can include an improved set of medical instruments that provide improved visualization during minimally invasive, trans-tympanic access to structures in the middle or inner ear. The devices, systems, and methods described herein can be used to treat and/or prevent a variety of conditions, including but not limited to hearing loss, including hidden hearing loss, noise-induced hearing loss, age-related hearing loss, drug-induced hearing loss (e.g., chemotherapy-induced hearing loss or aminoglycoside-induced hearing loss), sudden sensorineural hearing loss (SNHL), autoimmune inner ear disease, and the like.

While the devices, systems, materials, compounds, compositions, articles, and methods are described herein primarily in the context of treating hearing loss, it should be understood that devices, systems, materials, compounds, compositions, articles, and methods can also be used to treat any other disorder of the middle ear and/or inner ear including, but not limited to, tinnitus, balance disorders including vertigo, Meniere's disease, vestibular neuronitis, vestibular schwannoma, labyrinthitis, otosclerosis, ossicular chain dislocation, cholesteatoma, otitis media, middle ear infections, schwannoma, and tympanic membrane perforations, to provide a few examples.

Figure 58:
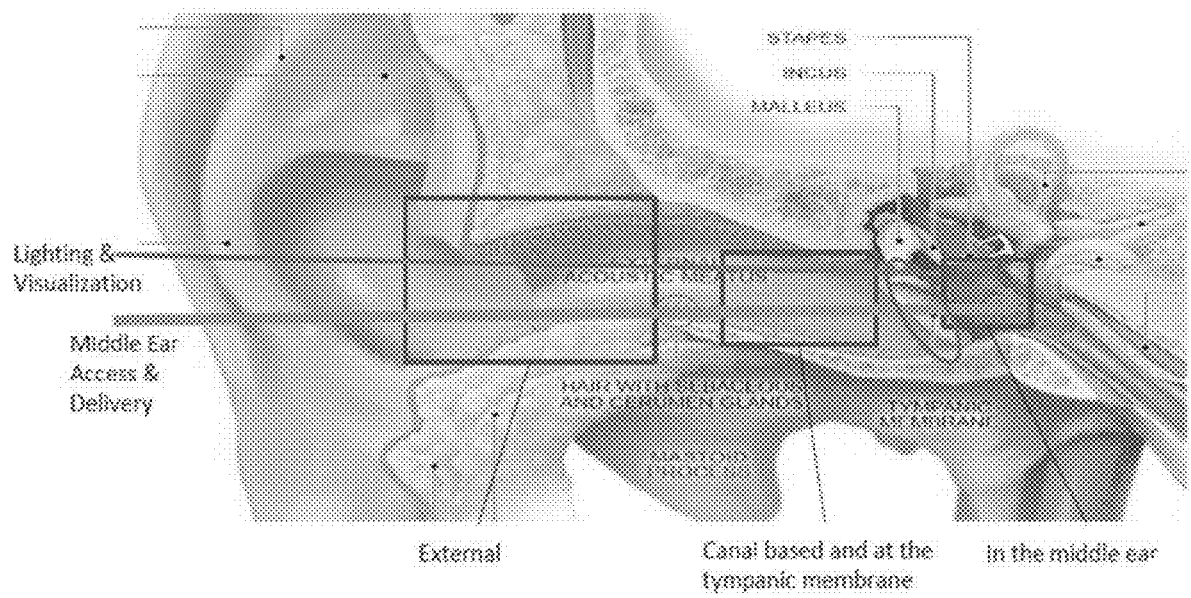
FIG. 58 is a schematic view of a system for facilitating minimally invasive access to the middle ear for purposes of diagnosing middle ear disturbances, planning procedures, and delivering treatment for inner and middle ear disorders.

This disclosure describes treatment methods and devices for treating the patient 10 using a minimally invasive approach. As depicted in FIG. 58, in some embodiments, the access system described herein can be configured to provide treatment, for example, to the cochlea via the patient's outer ear canal using various instruments as described further below. The instruments in such embodiments can be advanced through the tympanic membrane (TM) while one or more temporarily support structures provide added mechanical support to the tympanic membrane. In some cases, distal end portions of the instruments can be advanced into the middle ear and, optionally, toward a targeted anatomical structure (a non-limiting example includes a round window of the cochlea).

As described in more detail below, some instruments of the system can be configured to achieve a targeted delivery of a therapeutic formulation to a targeted site in the ear. In some embodiments, the therapeutic formulation that is delivered via the trans-tympanic instrument to the targeted site can be a semi-solid gel substance. As a gel substance, the delivery of the therapeutic formulation might remain in the targeted site so that the therapeutic formulation can gradually release its active ingredient for an extended period of time such as days, weeks, or even months.

Additional system improvements are described below (and in connection with FIGS. 58-61).

(1) Lighting and Visualization

Referring to FIG. 58, in some embodiments the system includes one or more lighting and visualization instruments, such as fixed "chandelier" lighting (for use with a minimally invasive access system) at or above the tympanic membrane, microcameras, OCT, and a trans-TM microscope viewing (with increased TM transparency, by applying glycerol or saline for example). In some embodiments, the endoscope has a lighting source.

In some embodiments, so-called "chandelier" lighting instruments or sources can be applied or mounted at or adjacent to the tympanic membrane without physically penetrating the membrane while still allowing sufficient light to pass through the tympanic membrane to facilitate visualization of middle ear structures.

In some embodiments, a solution or gel could be applied to the tympanic membrane in order to enhance the translucency of the membrane and thereby enhance the ability of external lighting such as chandelier lighting to pass through the membrane. If the clarity or translucency is sufficiently enhanced, the clinician can see directly through the membrane to visualize middle ear structures without necessitating endoscopes or other visualization instruments being physically inserted into the middle ear space. Glycerol or hypertonic saline are an examples of such a solution or gel that has been shown to enhance optical clarity of collagenous membranes. The gel or solution can be applied on the external surface of the membrane, the inner surface of the membrane through a small diameter instrument, or both.

Optical coherence tomography (OCT) is another visualization method that could be applied to facilitate visualization of the middle ear structures without necessitating perforation or penetration of the tympanic membrane.

An additional visualization modality can be located proximally on the shaft or handle of a primary endoscope or visualization apparatus. Such a visualization apparatus could be advantageous for assisting the clinician in managing the shaft's interaction with the ear canal, and could be displayed on the same viewing monitor or mechanism as the primary endoscope/visualization modality. This option may reduce the need for "back-and-forth" use of microscope and endoscope and provide closer viewing on structures of interest.

In some embodiments, the stabilizer devices described herein can include a camera device attached thereto. In some embodiments, the TM port devices described herein can include a light source, or can be trans-missive to light. In some embodiments, dyes or other agents can be used to improve contrast or to highlight one or more specific target areas. In some embodiments, dual or multi-wavelength lighting or visualization can be used to enhance visualization.

One of the largest challenges for even otologist's current use of endoscopes in approaches through tympanic membrane flaps or trans-mastoid approaches is the loss of binocularity typical to microscopes, and the associated difficulty with depth perception for instruments. As such, it can be considered that the use of depth markers on the shafts of access instruments would facilitate the use and adoption of access instruments.

(2) Tympanic Membrane Reinforcement

In some embodiments the system described herein can include one or more reinforcement structures for the TM, such as gels, tapes, bandages applied prior to TM perforation to prevent tearing and/or after TM perforation to repair/promote healing. The one or more reinforcement structures can be directly applied to the TM or in close proximity. Optionally, the one or more reinforcement structures can be combined or integrated with access cannulas or canal-based fixation.

For example, the reinforcement structure can include a liquid or gel formulation can be deposited on the surface of the tympanic membrane that then gels or polymerizes in a localized area (approx. 0.2-5 mm$^2$) as a way to enhance penetration or adhesion for access at the same area. Such a reinforcement gel can mechanically support the membrane as a way to reduce the likelihood of tearing of the tympanic membrane during perforation or insertion of visualization or access instruments, and during subsequent handling of tools that could apply lateral forces (in plane with the tympanic membrane). Visualization or access instruments could require long handles and shafts to navigate the ear canal and external ear, and those long shafts or handles could create the potential to act as long lever arms that could allow the clinician to unintentionally apply forces sufficient to tear the tympanic membrane while pursuing visualization or access or other therapeutic intervention in the middle or inner ear. Thermogelling poloxamers are an example of gels that have been shown to be compatible with the tympanic membrane. Alternatively, a more mechanically robust crosslinked PEG-based gel could be used. Examples could include materials used in wound closure such as DuraSeal, CoSeal, and Adherus.

Optionally, such a localized gel could be removed immediately post-procedure by mechanical peeling or by using agents designed/chosen to break up the gel. Alternatively, the reinforcement gel could be left in place post-procedure as a way to reinforce the membrane post-op and thereby promote healing. The gel may have self-sealing properties that would enhance the ability of the sides of a tympanic membrane perforation to re-connect and thereby promote healing. In some options, the gel can further include one or more anesthetic agents such as lidocaine to either reduce pain during the procedure or post-op. Additionally, the gel can include supplemental agents such as antibiotics or steroidal agents (such as dexamethasone) in it that improve healing at the tympanic membrane without requiring systemic or frequent local administration.

In another example, the reinforcement structure can include a tape material applied to the tympanic membrane as a way to facilitate perforation or access through the tympanic membrane while controlling localized tear forces or otherwise reducing the likelihood of tearing of the tympanic membrane. The reinforcement tape can be applied to promote healing post-op or post-access. Examples of reinforcing tape materials can include porous silk biomaterials (lamellar porous films and electrospun nanofibers), polymeric foams, polymeric hydrogels, polymeric alginates, and polymeric hydrocolloids. In some cases, an array of microneedles, micro-features, or the like can be used on the tape structure to enhance attachment of the tape to the tympanic membrane.

In some embodiments, the reinforcement structure can include a cauterizing agent to transiently and locally alter the tympanic membrane material. In such circumstances, the agent may be configured to allow the localized area (approx. 0.2-5 mm$^2$) to be altered as a way to enhance penetration or adhesion for access at the same area. In one example, the cauterizing agent can include phenol to provide such a cauterizing effect on the tympanic membrane.

Figure 59:
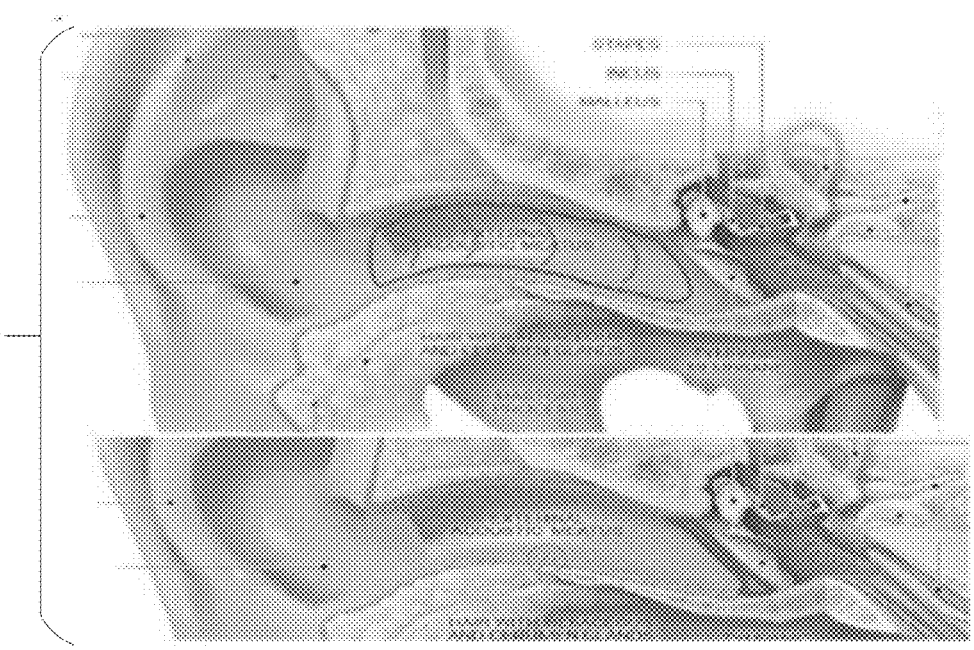
FIG. 59 shows side and front views of a tympanic membrane with one or more membrane support structures adjacent the tympanic membrane for use with the system of FIG. 58, in accordance with some embodiments.

(3) Canal-Based and TM-Adjacent Fixation (in the Outer Ear);

Referring to FIG. 59, in some embodiments the system includes one or more fixation structures positionable in the ear canal for providing support for access instruments during trans-tympanic access procedures. Such fixation structure can include an expandable "balloon" wall, a telescoping "finger trap"/stent structure, a ring configured to be anchored adjacent to the TM and equipped with a mesh or transparent web material for supporting instruments passing through the ring, and an improved speculum with instrument fixation rings near the TM.

For example, the localized reinforcement formulations or agents discussed above (such as the reinforcement gel) can be utilized across the whole length of the tympanic membrane as a way to fix a perforation or access site in place with respect to the ear canal walls and edges of the tympanic membrane. Such fixation or stabilization that spans the tympanic membrane has the potential advantage of greatly reducing lateral forces at an access site, which is especially advantageous mid-procedure while the clinician is manipulating instruments or visualization tools. In particular implementations, the gel is substantially translucent in order to allow direct visualization of the tympanic membrane.

Optionally, such a fixation or stabilization can be used in lieu of, or in any combination with, localized reinforcement such as gels or cannulas or grommets. It can also be considered that the stabilization or fixation does not need to cover the whole tympanic membrane and can cover an "X" shape, a line across, or other shape variations as ways to fix an access site in place.

In some embodiments, a mesh can similarly be used as a stabilization or fixation. Such a mesh can be placed adjacent to the tympanic membrane. Access or perforation of the tympanic membrane can be undertaken through holes in the mesh, while the access site can be prevented from moving laterally by strands of the mesh. Such a mesh can be combined with gel or other reinforcement or adhesion methods. Such a mesh could be constructed from polymers such as polypropylene, nylon, or others; elastomers such as polyurethane or silicone, or from fabrics. Optionally, the mesh may be substantially translucent in order to allow direct visualization of the tympanic membrane.

In further embodiments, an expandable balloon wall with central members can be considered for similarly providing fixation of an access site in place. Such a balloon can be in ring shape (similar to an inner tube of a tire) with stiffened members across the surface of its luminal area. A mesh could also be suspended across the luminal area. It can be considered that the "ring" of the balloon could be comprised of a series of smaller balloons, compliant or non-compliant, such that the luminal area can avoid being occluded at higher pressures.

In particular embodiments, an improved speculum with fixation fixtures at its distal end can be used in the ear canal in order to provide fixation or stabilization of the distal end of the speculum adjacent to the tympanic membrane.

In another embodiment, a support device having a "cupcake wrapper" structure (e.g., optionally including a series of pleats or folds in a tapered cylinder) can be inserted into the ear canal to provide fixation or stabilization relative to the ear canal. The pleats and folds would allow the device to conform or fit a range of ear canal sizes and shapes. It could have a mesh, gel, membrane or other material across the distal end that secures the fixation of the access site. Such an embodiment provides an additional potential advantage of protecting the ear canal wall to prevent accidental bumping or damage. Some patients are highly sensitive to bumping of the ear canal wall and flinch or otherwise interfere with a procedure.

In another embodiment, a tube of flexible, or elastomeric, or gel, or soft, or deformable, material can line the ear canal wall to protect the ear canal wall from bumping or damage while undertaking visualization or access. It can be considered that such a tube could be combined with a stabilization or fixation mesh, or ring, balloon or any of the other fixation methods discussed.

It can be appreciated that fixation or stabilization methods adjacent to the tympanic membrane can also be used in combination or as mounting methods for visualization or lighting.

FIGS. 72 and 73 show an example non-penetrating port device 2200 that can be placed adjacent to the TM 30. The non-penetrating port device 2200 defines one or more ports 2210 (one port 2210 is included in this example) through which instruments of any type (including endoscopes) described herein can be passed.

In some embodiments, the one or more ports 2210 include orientation features, such a slot or keyway that can be used for the orientation of instruments that pass through the one or more ports 2210. For example, in some embodiments the instrument (e.g., an endoscope, without limitation) used with a particular port 2210 can have an outer profile that matches the inner profile of the particular port 2210 (e.g., a key in a keyway). In that manner, the orientation of instruments that pass through the one or more ports 2210 can be established and maintained.

The non-penetrating port device 2200 includes two or more legs or features 2220 (in this example there are three of the legs 2220). The legs extend to feet 2222. In some embodiments, the feet 2222 can be releasably attached to the TM 30. In particular embodiments, the feet 2222 can be releasably attached to the tympanic annulus 32 surrounding the tympanic membrane 30. This can be advantageous for adding stability to the port(s) 2210. It can also be advantageous for easily establishing a distance of location for the port(s) 2210 relative to the tympanic annulus.

In some embodiments the feet 2222 are releasably attached to the TM 30 or tympanic annulus 32 using an adhesive 2224. Alternatively, in some embodiments the non-penetrating port device 2200 can be attached to the shaft of an instrument (e.g., an endoscope, without limitation) and the feet 2222 made to gently abut the TM 30 or tympanic annulus 32. In that fashion, the non-penetrating port device 2200 can be used as a depth-limiting and stabilization device.

In some embodiments, the two or more legs 2220 are arranged symmetrically. Alternatively, in some embodiments the two or more legs 2220 are arranged asymmetrically, as in the depicted embodiment. In some embodiments, the two or more legs 2220 include portions that make the two or more legs 2220 flexible. In some cases, such flexibility of the two or more legs 2220 can help to prevent excessive pressure from being exerted on the TM 30.

Figure 74:
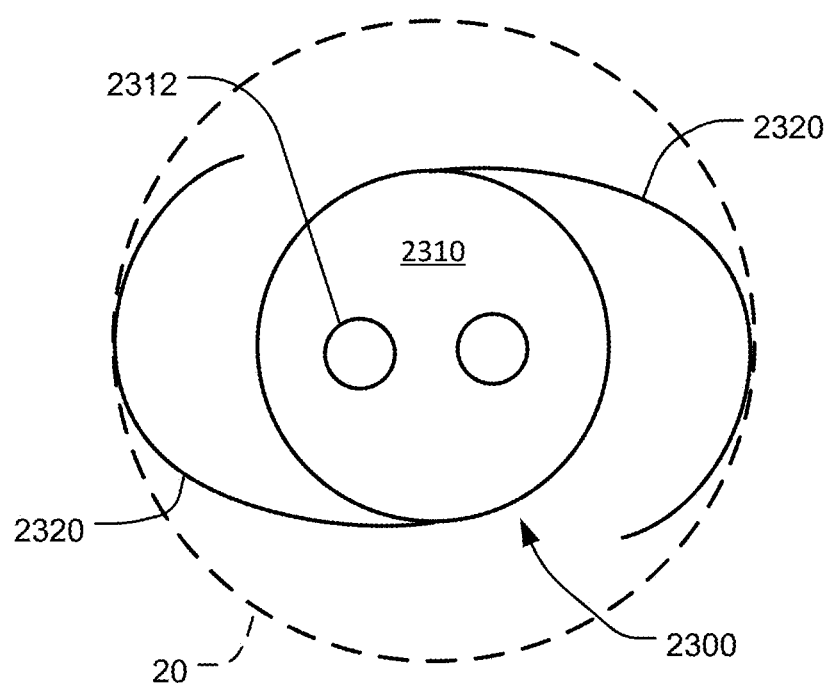
FIG. 74 shows another example stabilization device.

FIG. 74 shows another non-penetrating port device 2300 that can be placed in the outer ear canal 20 and/or adjacent to the TM 30. The non-penetrating port device 2300 has a port member 2310 that defines one or more ports 2312 (there are two ports 2312 in this example). The non-penetrating port device 2300 also has two or more radially expandable arms 2320 (there are two arms 2320 in this example) attached to the port member 2310. The arms 2320 can be the same length or differing lengths such that the port device 2300 or the throughways can be located off-center or in a specified position if so desired, which can be advantageous for establishing access in the posterior inferior region of the tympanic annulus for example. It can be envisioned that a variety of arm shapes, legs, or spring-like features could be used to maintain the port position. It can also be envisioned that the arms or legs could have foot-like features to either at their respective distal tips or along the length to help secure the assembly in position or help distribute outward force across a larger area.

It can be understood that having ports that are adjacent to the TM 30, but potentially non-contacting with the TM 30, can be advantageous for promoting stability of any instruments passing through incisions or holes in the TM 30 while minimizing contact with the rest of the delicate TM 30. Such ports also can be advantageous due to utilizing the stable ear canal structure to maintain position.

During delivery of the non-penetrating port device 2300 into the ear canal 20, the radially expandable arms 2320 are radially retracted near the port member 2310. After the desired positioning within the ear canal 20 is attained, the radially expandable arms 2320 can then be allowed to expand radially outward to abut against the wall of the ear canal 20. In that manner, the non-penetrating port device 2300 is temporarily fixed in place within the ear canal 20.

Figure 75:
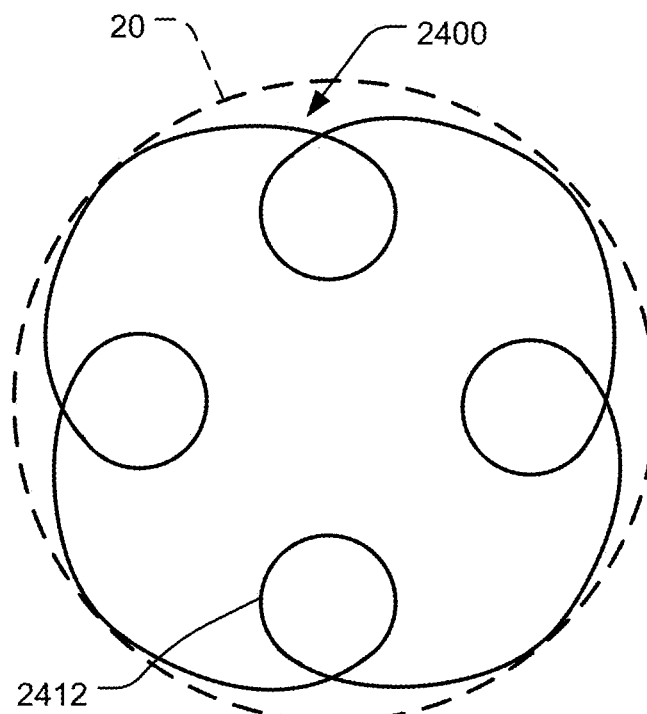
FIG. 75 shows another example stabilization device.

FIG. 75 shows another non-penetrating port device 2400 that can be placed in the outer ear canal 20 and/or adjacent to the TM 30. The non-penetrating port device 2400 is a wire that is looped to define one or more ports 2412 (there are four ports 2412 in this example). Alternatively, the spring-like wire could be slidably attached (in four places for the depicted port device 2400) to a port similar to that shown in FIG. 74, and the spring-like features could serve in place of the arms to secure the port against the canal wall.

During delivery of the non-penetrating port device 2400 into the ear canal 20, the non-penetrating port device 2400 is radially contracted. After the desired positioning within the ear canal 20 is attained, the non-penetrating port device 2400 can then be allowed to expand radially outward to abut against the wall of the ear canal 20, and to form the one or more ports 2412. In that manner, the non-penetrating port device 2400 is temporarily fixed in place within the ear canal 20.

(4) External Fixation

Figure 60:
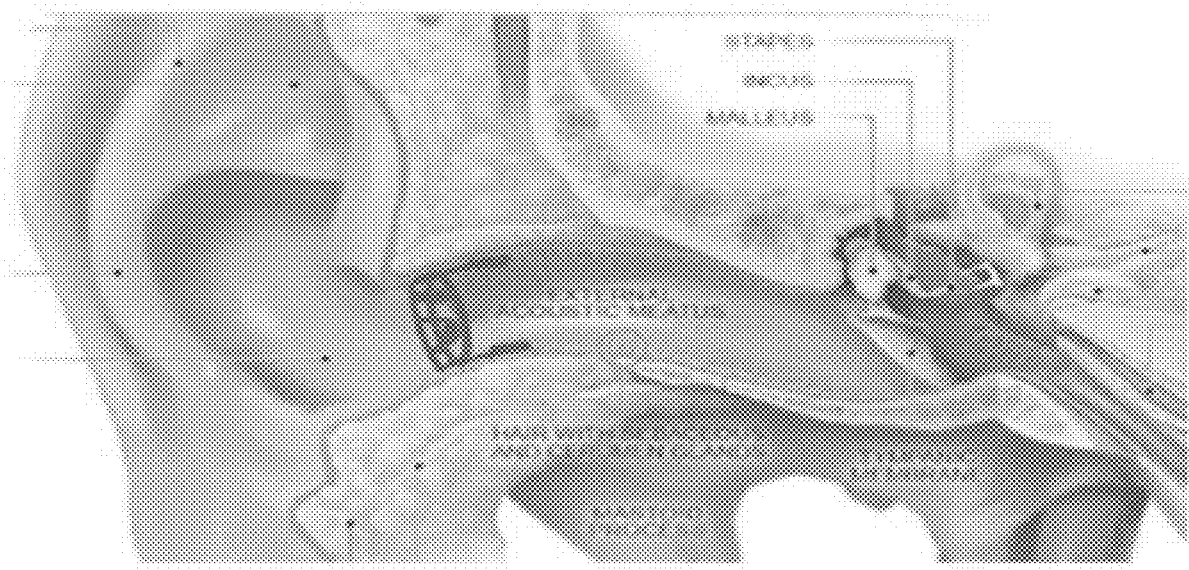
FIG. 60 shows a side view of a tympanic membrane with one or more external support structures for use with the system of FIG. 58, in accordance with some embodiments.

Referring to FIG. 60, in some embodiments the system includes external fixation structures positionable external to the ear canal for providing support for access instruments during trans-tympanic access procedures. For example, and improved otoscope with fixation supports located at ear canal aperture can be used to provide additional support and/or stabilization for the access instruments.

In some embodiments, control of an instrument or endoscope's impact on the access site's lateral movement or position on the tympanic membrane could be controlled through controlling the instrument or endoscope's handle's or shaft's motion at the external ear via a stabilization or fixation apparatus or device. Such a device could be mounted at the ear canal adjacent to the external ear or on the external ear itself. The device may optionally be transparent to minimize interference with a microscope or naked-eye visualization to the ear canal. Alternatively, the device can be equipped with its own camera embedded at its distal end to provide visualization of the ear canal.

Such an apparatus could control the degrees of freedom and magnitude of motion of the shafts of access or visualization instruments. In some implementations, notches, slots, or tighten-able gimbals can be used to limit the motion of the shafts of instruments. In some procedures, the device can be equipped with a lock to fix the position of the endoscope or other viewing apparatus after the desired viewing angle has been achieved. Such a configuration can free one of the clinician's hands and allow two-handed operation of instruments intended for therapeutic delivery, suction, pseudomembrane removal, or other tissue manipulation in the middle ear. This can be particularly advantageous for situations where clinicians are used to having both hands available for manipulation of instruments and have hand preference for specific tools regardless of which ear is being worked on.

In some embodiments, stimuli-responsive polymers can be integrated into the localized reinforcement or external reinforcement as a way to provide "early warning" of higher forces that could cause tears or disruption of the tympanic membrane.

It can be considered that such a fixation apparatus could aid in registration of the position of the handle of access or visualization instruments, and thereby aid in registration of insertion or access points in the tympanic membrane. This can be advantageous for ensuring subsequent access procedures either consistently use the access points from prior procedures, or avoid the access points from prior procedures. Some procedures to the middle ear (including regular delivery of therapeutic agents) that are contemplated herein may include repeated access through the tympanic membrane on a weekly-, monthly-, quarterly-, semiannually-, or annual basis. As such, the solutions described herein can reduce the likelihood of permanent scarring of the tympanic membrane, which might otherwise impact repeated access through the membrane.

Similarly, the system can be used to advantageously visualize and then mark the tympanic membrane as a way to highlight desired access point(s) for subsequent insertion of the access instrument(s) through the membrane.

(5) Middle-Ear Fixation

Figure 61:
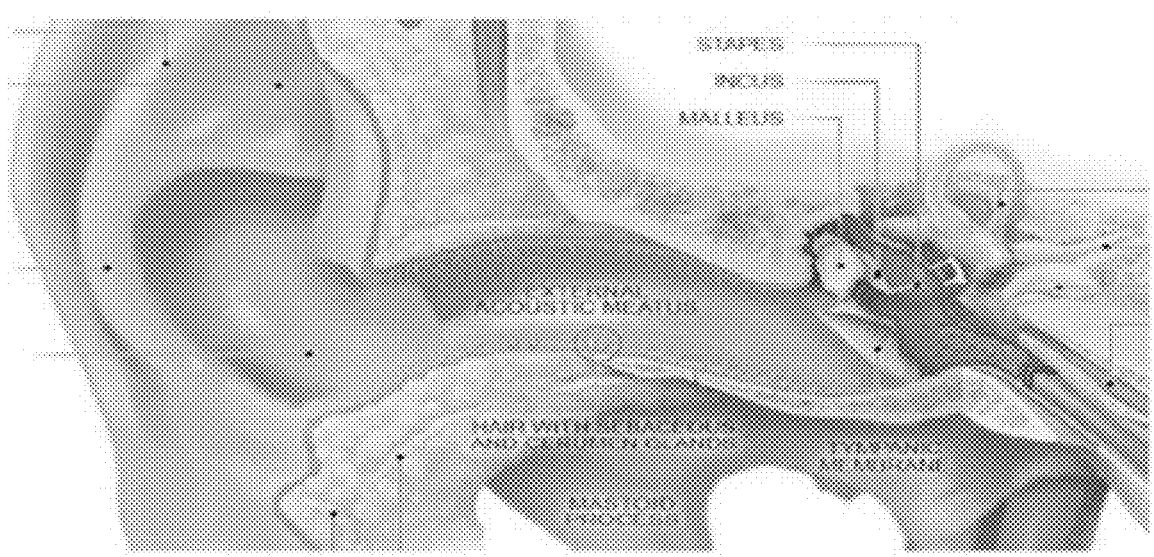
FIG. 61 shows a side view of a tympanic membrane subjected to middle ear inflation in accordance with some embodiments of the system of FIG. 58.

In some embodiments, the system includes one or more middle-ear fixation elements for providing support for access instruments during trans-tympanic access procedures. For example, the one or more middle-ear fixation elements can include an inflation material deposited in the middle ear to reinforce the tympanic membrane as depicted in FIG. 61.

For example, the middle ear can be temporarily filled with a translucent gel or polymer (such as gelled poloxamers or PEG), where the gel fills the middle ear and serves as the support for the shafts of access and/or visualization instruments. In this case the tympanic membrane itself serves as part of a sealing mechanism to hold the gel in place. The eustachian tube or ear canal would serve as the other exit from the middle ear, and could serve as the natural gradual removal mechanism for the gel or temporary polymer.

Optionally, the gel can be photo-curable, and a light source on the end of the endoscope could be used to selectively cure a thin-walled channel through the gel as the endoscope is slowly retracted away from the desired delivery spot (e.g., the round window membrane), thereby creating a channel through the gel that could be used to deliver a therapeutic formulation to the delivery spot (such as round window membrane). The formulation could then be photo-cured in place at the desired location. The channel and bulk of the gel would then degrade and be carried away through the eustachian tube.

Additionally or alternatively, an apparatus at the ear canal exit to the external ear could be used to provide sealing or containment of a translucent gel or temporary polymer (such as gelled poloxamers or PEG), where the gel fills the ear canal and serves as the support for the shafts of access and/or visualization instruments. Depending on the orientation of the patient and their ear canal, the gel could be placed in the ear canal and not require sealing or containment to stay in place.

In some embodiments, the use of a fluid or gel in the middle ear for "underwater surgery" can serve to tamponade bleeding, improve TM visualization, and/or provide support for instruments, to name a few advantages. In some embodiments, the outer ear canal can also be filled (or partially filed) with a fluid or gel. In some embodiments, pathways can be created in cured gel that can serve as channels or lumens for the delivery of substances with therapeutic agents.

Figure 62:
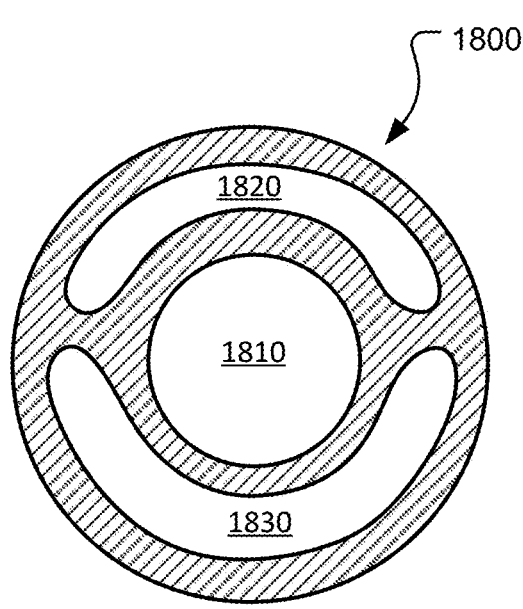
FIGS. 62 and 63 show cross-sectional views of example endoscope shafts.

Referring to FIG. 62, a cross-sectional view of an example endoscope shaft 1800 is shown. In this example, the outer profile of the endoscope shaft 1800 is circular in cross-section.

The endoscope shaft 1800 defines a concentric centrally-located working channel 1810. The instruments described in this disclosure can be slidably advanced within the working channel 1810. While the cross-sectional shape of the depicted working channel 1810 is circular, in some embodiments other shapes can be defined by the working channel 1810 such as, but not limited to, ovular, elliptical, polygonal, and the like, without limitation. In some embodiments, the endoscope shaft 1800 can define two or more of the working channels 1810.

The endoscope shaft 1800 also includes lighting 1820 (e.g., fiber optic elements, LED(s), and/or combinations thereof) and fiber optics for image capturing 1830. As shown, in some embodiments these can be arranged in arcuate patterns (in cross-section). Other geometric arrangements are also envisioned such as, but not limited to, circular, ovular, linear, polygonal, and the like, without limitation.

Figure 63:
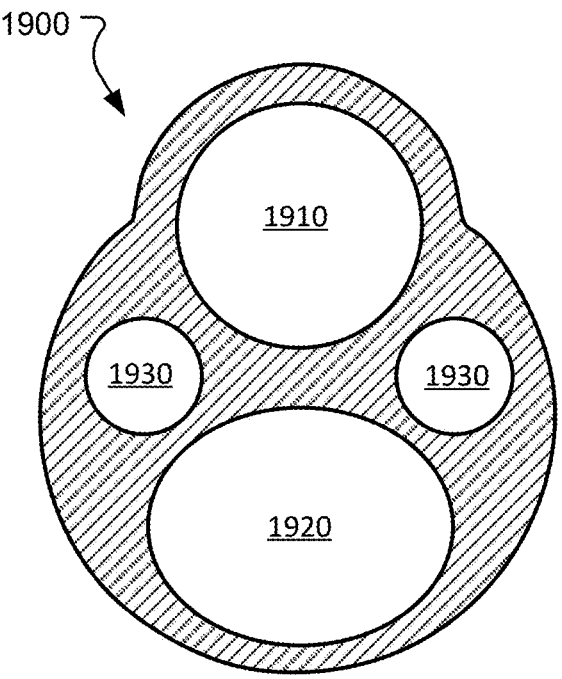

Referring to FIG. 63, a cross-sectional view of another example endoscope shaft 1900 is shown. In this example, the outer profile of the endoscope shaft 1900 is oblong in cross-section.

The endoscope shaft 1900 defines a working channel 1910 that is offset from the geometric center of the endoscope shaft 1900. While the cross-sectional shape of the depicted working channel 1910 is circular, in some embodiments other shapes can be defined by the working channel 1910 such as, but not limited to, ovular, elliptical, polygonal, and the like, without limitation. In some embodiments, the endoscope shaft 1900 can define two or more of the working channels 1910.

The endoscope shaft 1900 also includes a lighting element 1220 (e.g., one or more fiber optic element(s), one or more LED(s), and/or combinations thereof) and image capturing elements 1930 (e.g., cameras, fiber optics, and combinations thereof). As shown, in some embodiments there are two of the image capturing elements 1930. Alternatively, in some embodiments there is a single image capturing element 1930 and two of the lighting elements 1920.

Figure 64:
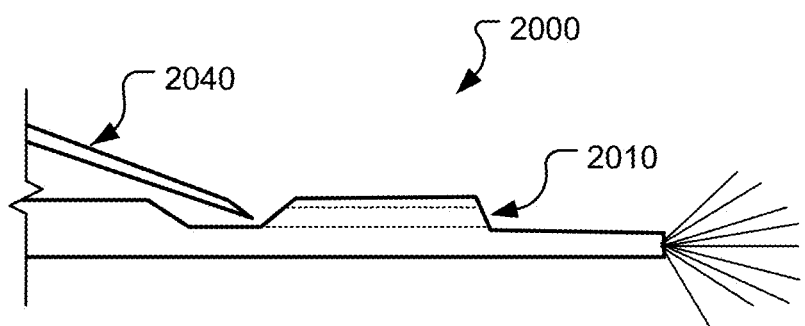
FIG. 64 shows a distal end portion of an example endoscope shaft.

Referring also to FIG. 64, a distal end portion of an endoscope shaft 2000 is depicted. The endoscope shaft 2000 defines a working channel 2010 that, in this example, will slidably receive an example instrument 2040. This illustration makes it plain that the entrance to the working channel 2010 and the exit from the working channel 2010 can be anywhere along the shaft 2000. For example, in the depicted arrangement the working channel 2010 extends for just a short distance along the distal end portion of the endoscope shaft 2000. Accordingly, any of the working channels described herein can be configured with an entrance and exit anywhere along the shaft of the endoscope.

Figure 65:
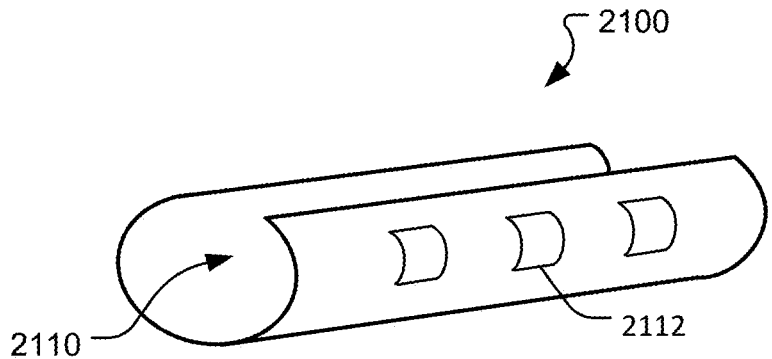
FIG. 65 shows an example working channel of an endoscope.

FIG. 65 illustrates a portion of another type of shaft 2100 that defines a working channel 2110. In this example, the working channel 2110 is C-shaped in cross-section. That is, an open portion of the working channel 2110 extends longitudinally along the shaft 2100. Said another way, the working channel 2110 in this example is an open-topped channel. Additionally, in some embodiments one or more fenestrations 2112 (which are optional) are included as openings to the working channel 2110. The openness of the working channel 2110 can be advantageous for sterilization of the long, small working channel 2110. That is, sterilization gasses and/or steam can pass into and out of the long, small working channel 2110 to a greater extent because of its openness.

Figure 66:
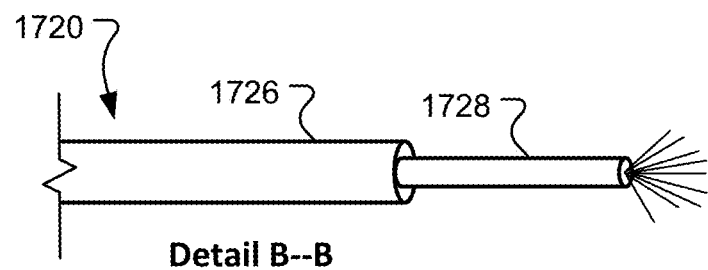
FIGS. 66-68 show a distal end portion of another example endoscope.

FIG. 66 illustrates another example distal tip portion of the shaft 1720 of the endoscope instrument 1700 shown in FIG. 55. In this example, the shaft 1720 includes a proximal shaft portion 1726 and a distal shaft portion 1728. The distal shaft portion 1728 extends distally from the distal end of the proximal shaft portion 1726. In some embodiments, the central longitudinal axes of the proximal shaft portion 1726 and the distal shaft portion 1728 are collinear. In some embodiments, the central longitudinal axes of the proximal shaft portion 1726 and the distal shaft portion 1728 are parallel but offset from each other. In some embodiments, the central longitudinal axes of the proximal shaft portion 1726 and the distal shaft portion 1728 are skew lines, or are intersecting lines which are not parallel.

The distal shaft portion 1728 is smaller in cross-sectional size than the proximal shaft portion 1726. For example, in some embodiments the size ratio of the outer dimensions of the distal shaft portion 1728 compared to the proximal shaft portion 1726 is between 0.1:1 and 0.8:1, or between 0.2:1 and 0.7:1, or between 0.3:1 and 0.6:1, or between 0.4:1 and 0.5:1, without limitation.

While the depicted embodiment shows an abrupt transition in outer size between the proximal shaft portion 1726 and the distal shaft portion 1728, in some embodiments a gradual transition such as a taper is used.

In some embodiments, the longitudinal length of the distal shaft portion 1728 is between 4 mm and 20 mm, or between 6 mm and 18 mm, or between 8 mm and 14 mm, or between 10 mm and 12 mm, or between 6 mm and 14 mm, or between 8 mm and 12 mm, without limitation.

The depicted distal tip portion of the shaft 1720 that includes the smaller distal shaft portion 1728 can be advantageous for at least some of the treatment procedures described herein. For example, in some cases just the smaller distal shaft portion 1728 is passed through the TM. That is, in some cases, the transition between the proximal shaft portion 1726 and the distal shaft portion 1728 can be positioned to be adjacent to the TM, and only the smaller distal shaft portion 1728 passes through the TM (e.g., using a TM port device, via a puncture/incision in the TM, or through an area where the TM has been opened using any other technique). Accordingly, in some embodiments a smaller opening through or around the TM can be made (in comparison to conventional endoscopes that are typically unidimensional along the shaft). In some embodiments, atraumatic bumper elements can be included at the transition between the proximal shaft portion 1726 and the distal shaft portion 1728 so that, if the TM is contacted by the transition, the TM is protected from being damaged.

Moreover, in some cases the transition between the proximal shaft portion 1726 and the distal shaft portion 1728 can be advantageously used to limit or control the insertion depth of the endoscope shaft 1720 into the middle ear. Such an arrangement (where the proximal shaft portion is larger than the distal shaft portion) can also be used for other types of instruments described herein, without limitation.

In some cases, having the diametric tapers or non-uniform shaft outer diameters of the proximal shaft portion 1726 and the distal shaft portion 1728 allows for greater stiffness at same time as easier manufacturing. As an example, the smaller diameter distal portion can be more delicate, especially over longer lengths. Having larger diameter proximal can reduce the portion of the assembly prone to damage. In some embodiments, the distal shaft portion 1728 can be made with more flexibility (less rigidity) to reduce the lateral forces that may be exerted to the TM by the distal shaft portion 1728 (and to reduce the potential for tearing or otherwise damaging the TM). The less rigidity could also be achieved by using different material to sheath the distal shaft portion 1728 for more flexibility.

While in the depicted embodiment the light emitted from the shaft 1720 is projecting from the distal end of the distal shaft portion 1728, in some embodiments the light can be alternatively or additionally project from the distal end of the proximal shaft portion 1726 (e.g., at the transition between the proximal shaft portion 1726 and the distal shaft portion 1728). That is, in some cases light emitted from the shaft 1720 is projecting from the distal end of the proximal shaft portion 1726 which is in the ear canal (or external to the TM). In such as case, the light can be transmitted through the TM and into the middle ear.

In some embodiments, the proximal shaft portion 1726 can contain a working channel, e.g., similar to that shown in FIG. 64.

Figure 77:
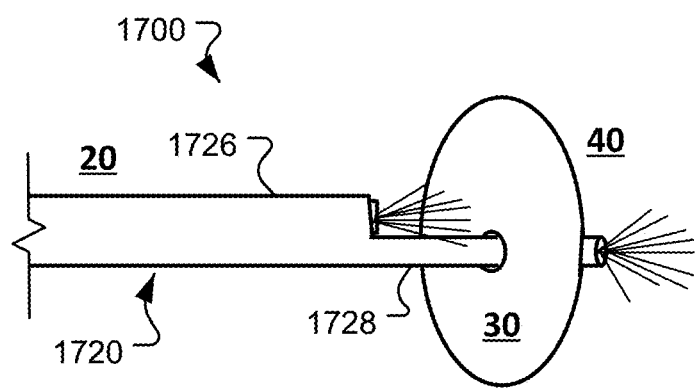

While in the depicted embodiment the images viewed by the endoscope are captured at the distal end of the distal shaft portion 1728, in some embodiments the images viewed by the endoscope are captured at the distal end of the proximal shaft portion 1726 (e.g., at the transition between the proximal shaft portion 1726 and the distal shaft portion 1728 as shown in FIG. 77). In some embodiments, two images are viewed by the endoscope, such as from both at the distal end of the distal shaft portion 1728 and the distal end of the proximal shaft portion 1726.

Figure 67:
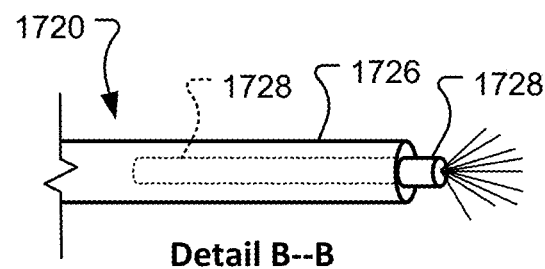

Referring also to FIG. 67, in some embodiments the distal shaft portion 1728 is retractable and extendable from the distal end of the proximal shaft portion 1726. For example, in FIG. 65 the distal shaft portion 1728 is retracted relative to the distal end of the proximal shaft portion 1726, and in FIG. 66 the distal shaft portion 1728 is extended relative to the distal end of the proximal shaft portion 1726. In such an embodiment, the clinician operator of the endoscope can controllably extend the distal shaft portion 1728 from the distal end of the proximal shaft portion 1726 to any desired length within a range from about 0 mm to about 20 mm, or more. In some embodiments, markers can be included on the endoscope to visually indicate the distance that the distal shaft portion 1728 is extending from the distal end of the proximal shaft portion 1726.

Figure 68:
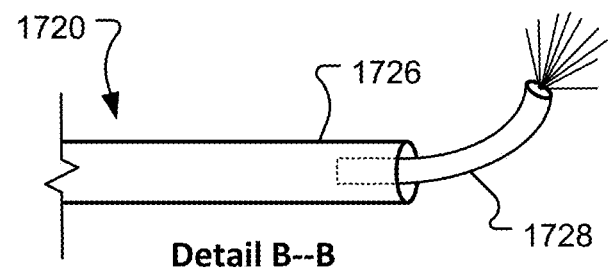

Referring also to FIG. 68, in some embodiments the distal shaft portion 1728 is retractable and extendable from the distal end of the proximal shaft portion 1726, and the distal shaft portion 1728 is or can be curved. In some embodiments, the distal shaft portion 1728 is naturally curved so that the curve is exhibited as/when the distal shaft portion 1728 extends from the distal end of the proximal shaft portion 1726. In some embodiments, the distal shaft portion 1728 is also rotatable relative to the proximal shaft portion 1726. Accordingly, by controllably rotating and/or extending the distal shaft portion 1728 relative to the proximal shaft portion 1726, the clinician can effectively position the distal tip of the distal shaft portion 1728 in a wide variety of positions and orientations.

In some embodiments, the distal shaft portion 1728 is controllably deflectable or steerable (e.g., using internal control wires, using one or more internal shaft(s), etc.). In such a case, the distal shaft portion 1728 can be either linear (FIG. 66) or curved (e.g., FIG. 68), as desired by a clinician operator of the endoscope. In such an embodiment, the distal shaft portion 1728 can be retractable and extendable from the distal end of the proximal shaft portion 1726, or the distal shaft portion 1728 can be fixed relative to the distal end of the proximal shaft portion 1726.

In some embodiments, the endoscopes described herein (e.g., the endoscope instrument 1700 of FIGS. 55-57, and FIGS. 66-68) can include indicators on the handle and/or shaft that helps the clinician user to mentally envision the orientation of the distal shaft portion 1728. Such markings can be useful for helping the clinician user to better understand the orientations of the images that are captured by the endoscope and displayed on a screen. Put simply, the markings can be useful for helping the clinician user to know which way is up, etc. Such markings can be purely visual, can be tactile (e.g., one or more raised or indented areas on the handle), and combinations thereof. A tactile marking (e.g., a ridge, a bump, etc.) on the handle of the endoscope can be used to rotate the distal shaft portion 1728 in some embodiments. In some embodiments, markings can also be displayed on the screen(s) that is/are used for viewing the images captured by the endoscope to assist in denoting on-screen orientation.

In particular embodiments, one or more gyroscope devices can be incorporated into the endoscopes described herein. Such gyroscope devices can also be used to indicate the orientation of the endoscope shafts and images (e.g., which way is up), or in combination with image processing to always show the on-screen image "up" relative to gravity.

Figure 69:
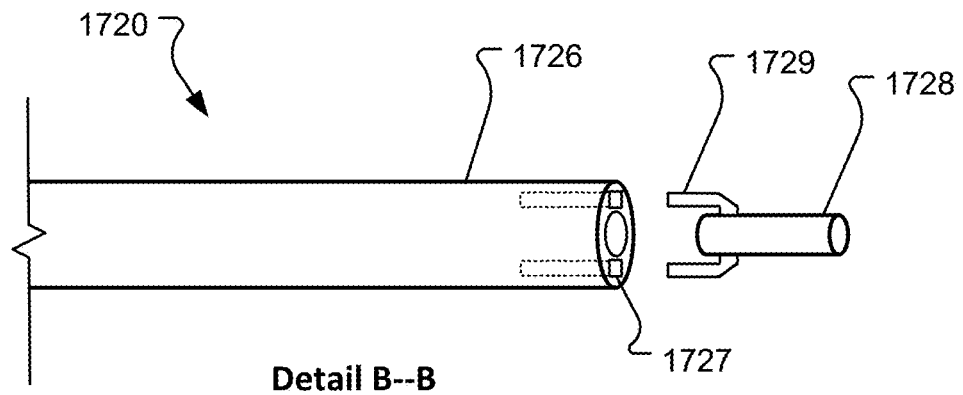
FIGS. 69 and 70 show a distal end portion of another example endoscope.
Figure 70:
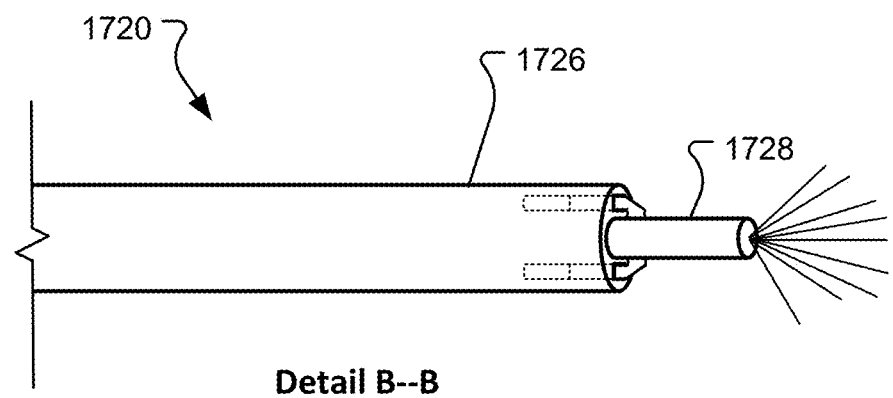

Referring also to FIGS. 69 and 70, in some embodiments the distal shaft portion 1728 can be detachable from the distal end of the proximal shaft portion 1726. Various types of mechanisms for releasably coupling the distal shaft portion 1728 to the distal end of the proximal shaft portion 1726 can be used. For example, in the depicted embodiment the distal shaft portion 1728 includes projections 1729 that engage in corresponding recesses 1727 defined by the distal end of the proximal shaft portion 1726. Accordingly, the distal shaft portion 1728 can, in some embodiments, snap into engagement with the proximal shaft portion 1726. Other types of mechanisms for releasably coupling the distal shaft portion 1728 to the distal end of the proximal shaft portion 1726 can be used such as, but not limited to, threaded connections, collet connections, bayonet connections, and the like, without limitation.

In some embodiments, the detachable distal shaft portion 1728 is a single-use, disposable item. Alternatively, in some embodiments the detachable distal shaft portion 1728 is a multi-use, sterilize-able item.

In some embodiments, as depicted, a proximal end portion of the detachable distal shaft portion 1728 is received within a receptacle defined by the distal end of the proximal shaft portion 1726. In some such embodiments, the proximal shaft portion 1726 can include a lens that receives images captured by the detachable distal shaft portion 1728.

Referring to FIG. 71, additional endoscope features are also envisioned within the scope of this disclosure. In the depicted embodiment, the distal shaft portion 1728 includes one or more fiber optic elements, glass, or other high optical-transmittance elements that transmit images to a lens 1740 within the proximal shaft portion 1726. The lens 1740, in turn, transmits the images to an adjacent CCD camera 1750 located within the proximal shaft portion 1726. The CCD camera 1750 can be larger in size than if it was located in the distal shaft portion 1728. The CCD camera 1750 can be operatively connected to an image processor 1760 that can be located in the proximal shaft portion 1726, or in another more proximal portion of the endoscope.

The depicted arrangement can have a number of advantages. For example, the relatively short lengths of the one or more fiber optic elements in the distal shaft portion 1728 that feed images to the lens 1740 allows a smaller distal shaft portion 1728 with little image resolution loss along its length. This also corresponds to lower manufacturing costs since it is more expensive to have long fibers for a given level of signal quality. Said another way, the depicted arrangement allows for a smaller distal shaft portion 1728 to get same resolution as a larger diameter endoscope since signal loss is typically overcome by having more fibers. Further, having the processing of the digital images at the image processor 1760 be relatively close to the CCD camera 1750 again reduces signal loss.

Figure 76:
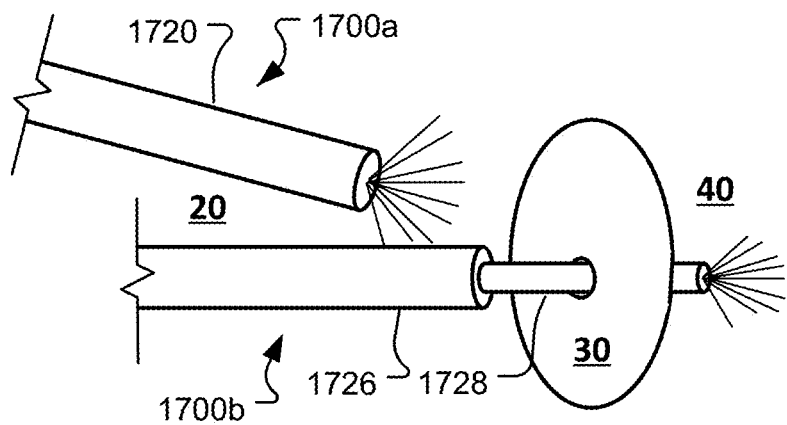
FIGS. 76 and 77 show example arrangements for concurrently obtaining two endoscope images.

Referring to FIG. 76, in some cases the procedures described herein can be performed using two endoscopes. For example, as depicted, a first endoscope 1700a can be positioned in the ear canal 20 with a view of the TM 30, and a second endoscope 1700b can extend through the TM into the middle ear 40. The first endoscope 1700a can be used to visualize the second endoscope 1700b (and/or other instruments) as it is being advanced through the TM 30. In some embodiments, the first endoscope 1700a can be the light source for the second endoscope 1700b. One or both of the endoscopes 1700a-b can be stabilized by any of the stabilization devices described herein.

In some embodiments, the first endoscope 1700a can have binocular vision. In particular embodiments, the second endoscope 1700b can have binocular vision. In some cases, both of the endoscopes 1700a-b can be advanced through the TM 30 into the middle ear 40.

Referring to FIG. 77, in some embodiments a single shaft 1720 of an endoscope 1700 can include two locations where images are captured. For example, in the depicted embodiment a first image is captured at the transition between the proximal shaft portion 1726 and the smaller distal shaft portion 1728. This provides a view of the TM 30 from the ear canal 20. A second image is captured at the distal end of the distal shaft portion 1728. This provides a view of the middle ear 40. In some embodiments, a single light source can be mounted at the transition between the proximal shaft portion 1726 and the smaller distal shaft portion 1728. The single shaft 1720 can be stabilized by any of the stabilization devices described herein.

When two images are captured, such as exemplified by FIGS. 76 and 77, the two images can be displayed on a single screen, or on two screens. When the two images are displayed on a single screen, the images can be adjusted/configured by a clinician user. For example, the images can be sized and positioned on the screen as preferred by the clinician user. The screen and/or endoscopes can also include orientation markers as described above. It can be envisioned that the simultaneous visualization at varying depths would be advantageous for use with other middle ear procedures such as but not limited to cholesteatoma removal, myringotomy, stapes reconstruction, or others.

Figure 78:
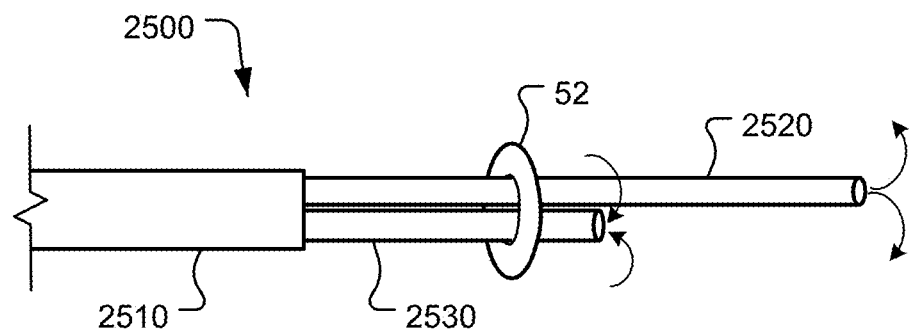
FIGS. 78 and 79 show an example device for delivering a substance and for aspiration.
Figure 79:
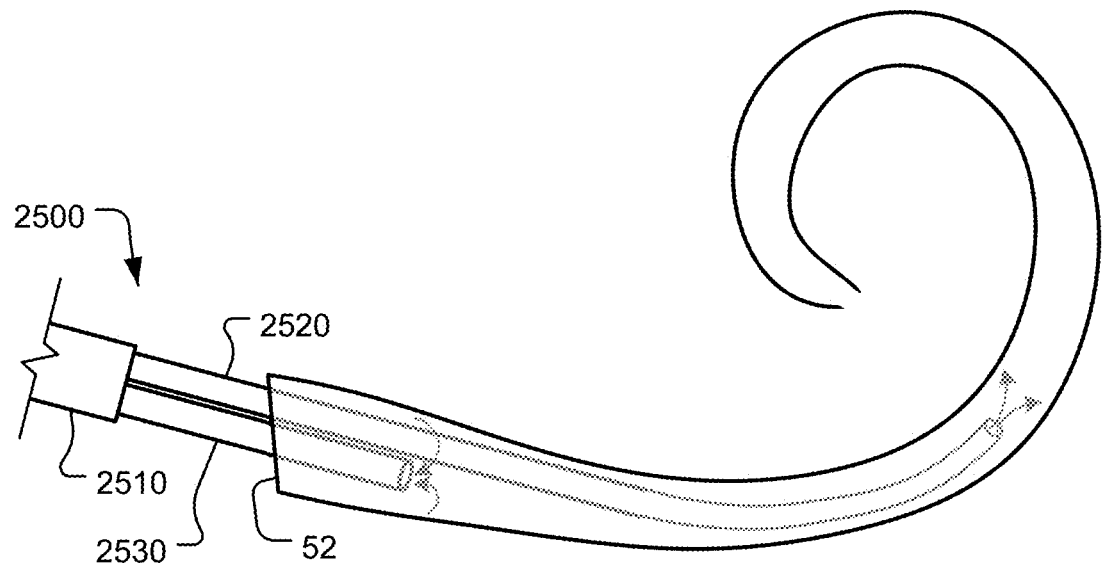

FIGS. 78 and 79 illustrate an example substance delivery and aspiration device 2500 (or simply "device 2500"). The device 2500 includes a main shaft 2510. The device 2500 also includes a substance delivery catheter 2520 and an aspiration catheter 2530. The substance delivery catheter 2520 and the aspiration catheter 2530 extend distally from the main shaft 2510.

In some embodiments, the substance delivery catheter 2520 and the aspiration catheter 2530 are extendable and retractable (individually or jointly) in relation to the main shaft 2510. The substance delivery catheter 2520 and the aspiration catheter 2530 can be flexible and atraumatically conformable to the tissues of the ear (including the middle and inner ear).

The device 2500 has various uses. In the depicted example, the device 2500 is being used to deliver a substance (e.g., with one or more therapeutic agents) to the inner ear (via the round window 52) and to aspirate fluids therefrom. In some embodiments, the delivery and aspiration are performed entirely or at least partially simultaneously. Alternatively, in some embodiments the delivery and aspiration are performed at differing times. Such devices can be for temporary use or for long-term use.

While the devices, systems, materials, compounds, compositions, articles, and methods described herein described in the context of treating hearing loss, it should be understood that the devices, systems, materials, compounds, compositions, articles, and methods may be used to treat any disorder of the middle ear and/or inner ear including, but not limited to, tinnitus, balance disorders including vertigo, Meniere's Disease, vestibular neuronitis, vestibular schwannoma, labyrinthitis, otosclerosis, ossicular chain dislocation, cholesteatoma, otitis media, middle ear infections, and tympanic membrane perforations, to provide a few examples.

Although the round window membrane is one target site for therapeutic agent delivery or access, the systems and methods described herein can also be used for precise delivery of therapeutic agents to other target sites, such as the oval window or other parts of the middle ear cavity, and for providing access to other features or regions of the middle ear. For example, the systems and methods described herein can be used for minimally invasive surgical reconstruction of the ossicular chain, for removal of cholesteatoma, for diagnostic assessment, and other procedures. Any and all such techniques for using the systems and methods described herein are included within the scope of this disclosure.

The devices, systems, materials, compounds, compositions, articles, and methods described herein may be understood by reference to the above detailed description of specific aspects of the disclosed subject matter. It is to be understood, however, that the aspects described above are not limited to specific devices, systems, methods, or specific agents, as such may vary. It is also to be understood that the terminology used herein is for the purpose of describing particular aspects only and is not intended to be limiting.

A number of embodiments have been described. Nevertheless, it will be understood that various modifications may be made without departing from the claim scope here. Accordingly, other embodiments are within the scope of the following claims.

What is claimed is:

1. A system for delivering a therapeutic formulation adjacent to a cochlea of a patient, the system comprising:
    first and second tympanic membrane port devices configured to be removably implanted in spaced apart positions in a tympanic membrane of the patient, the first tympanic membrane port device defining a first lumen and the second tympanic membrane port device defining a second lumen;
    an endoscope slidable through the first lumen of the first tympanic membrane port device while the first tympanic membrane port is implanted in the tympanic membrane such that a distal end portion of the endoscope is positionable in a middle ear to visualize a round window niche of the cochlea; and
    an injector instrument slidable through the second lumen of the second tympanic membrane port device while the second tympanic membrane port device is implanted in the tympanic membrane such that a curved distal tip portion of the injector instrument is advanceable to the round window niche, the injector instrument configured to deliver the therapeutic formulation to the round window niche while the distal end portion of the endoscope in the middle ear is spaced apart from the injector instrument to provide visualization of the injector instrument.

2. The system of claim 1, further comprising a tympanic membrane port insertor configured to removably implant the first and second tympanic membrane port devices in the tympanic membrane.

3. The system of claim 2, wherein the tympanic membrane port insertor comprises:
    an elongate delivery sheath;
    a pusher catheter; and
    a trocar needle.

4. The system of claim 3, wherein the pusher catheter is slidably disposed within a lumen defined by the delivery sheath, and wherein the trocar needle is slidably disposed within a lumen defined by the pusher catheter.

5. The system of claim 3, wherein an outer diameter of the trocar needle is less than an inner diameter of the first and second lumens of the first and second tympanic membrane port devices, and wherein an outer diameter of the pusher catheter is greater than the inner diameter of the first and second lumens of the first and second tympanic membrane port devices.

6. The system of claim 1, wherein the curved distal tip portion of the injector instrument includes a single curve.

7. The system of claim 1, wherein the curved distal tip portion of the injector instrument includes a first curved portion and a second curved portion.

8. The system of claim 7, wherein the first and second curved portions are in a same plane and curve in opposing directions.

9. The system of claim 1, further comprising a membrane modification instrument slidable through the second lumen of the second tympanic membrane port device while the second tympanic membrane port device is implanted in the tympanic membrane such that a distal tip portion of the membrane modification instrument is advanceable to the round window niche, the membrane modification instrument configured for tearing a pseudomembrane at the round window niche while the distal end portion of the endoscope in the middle ear is spaced apart from the membrane modification instrument and provides visualization of the membrane modification instrument.

10. A system for delivering an otic treatment fluid adjacent to a cochlea of a patient, the system comprising:
    an ear injection device including a proximal end and a flexible distal tip portion, the flexible distal tip portion being adjustable from a longitudinally straight shape during advancement through a tympanic membrane of the patient to a curved shape to orient a distal delivery port of the distal tip portion at a round window niche adjacent to the cochlea; and an otic treatment fluid source in fluid communication with the ear injection device so that the distal delivery port of the distal tip portion is configured to deliver the otic treatment fluid into the round window niche while the flexible distal tip portion is arranged in the curved shape;

an endoscope; and a first tympanic membrane port device configured to be removably implanted in the tympanic membrane of the patient, wherein the first membrane port device defines a first lumen, and wherein the ear injection device is configured to pass through the first lumen;

a second tympanic membrane port device configured to be removably implanted in the tympanic membrane of the patient in a laterally spaced apart position relative to the first tympanic membrane port device, wherein the second membrane port device defines a second lumen, and wherein the endoscope is configured to pass through the second lumen.

11. The system of claim 10, wherein the ear injection device also includes a sheath, and wherein the distal tip portion is within a lumen of the sheath during the advancement through the tympanic membrane.

12. The system of claim 11, wherein the distal tip portion has shape memory to seek the curved shape when the distal tip portion is extended distally from a distal end of the sheath.

13. The system of claim 10, wherein the distal tip portion is selectively adjustable to the curved shape by manipulating one or more control members slidably coupled within lumens defined by the distal tip portion.

* * * * *